United States Patent
Barbour et al.

(10) Patent No.: US 11,179,073 B2
(45) Date of Patent: Nov. 23, 2021

(54) METHOD FOR UNCOVERING DEEPLY HIDDEN ENZYME-LIKE BEHAVIORS FROM PHYSIOLOGICAL TIME-SERIES MEASURES FOR DISEASE DETECTION, MONITORING AND OTHER APPLICATIONS

(71) Applicants: Photon Migration Technologies Corp., Glen Head, NY (US); SLB Inspirations Ltd., Glen Head, NY (US)

(72) Inventors: Randall L. Barbour, Glen Head, NY (US); San-Lian S. Barbour, Glen Head, NY (US); Harry L. Graber, New York, NY (US)

(73) Assignees: Photon Migration Technologies Corp., Glen Head, NY (US); SLB Inspirations Ltd., Glen Head, NY (US)

( * ) Notice: Subject to any disclaimer, the term of this patent is extended or adjusted under 35 U.S.C. 154(b) by 0 days.

(21) Appl. No.: 17/224,602

(22) Filed: Apr. 7, 2021

(65) Prior Publication Data
US 2021/0321915 A1    Oct. 21, 2021

Related U.S. Application Data

(60) Provisional application No. 63/007,086, filed on Apr. 8, 2020.

(51) Int. Cl.
  *A61B 5/145*    (2006.01)
  *A61B 5/00*     (2006.01)
(52) U.S. Cl.
  CPC ........ *A61B 5/14542* (2013.01); *A61B 5/0095* (2013.01); *A61B 5/4064* (2013.01); *A61B 5/4312* (2013.01); *A61B 5/441* (2013.01); *A61B 5/7246* (2013.01)
(58) Field of Classification Search
  CPC ... A61B 5/145; A61B 5/14542; A61B 5/1455; A61B 5/0095; A61B 5/4064; A61B 5/4312; A61B 5/441; A61B 5/7246; A61B 5/7271
  See application file for complete search history.

(56) References Cited

U.S. PATENT DOCUMENTS

| | | | |
|---|---|---|---|
| 6,516,209 B2 | 2/2003 | Cheng et al. | |
| 6,937,884 B1 | 8/2005 | Barbour | |
| 8,406,838 B2 | 3/2013 | Kato | |
| 9,265,441 B2* | 2/2016 | Pereira | A61B 5/7267 |
| 9,700,248 B2 | 7/2017 | Ozaki et al. | |
| 9,730,649 B1 | 8/2017 | Jepsen | |
| 10,105,090 B2 | 10/2018 | Barbour et al. | |
| 10,503,967 B2* | 12/2019 | Sarrafzadeh | G06K 9/00348 |
| 10,842,444 B2* | 11/2020 | Hoeng | A61B 5/7246 |
| 2005/0080323 A1 | 4/2005 | Kato | |
| 2013/0109950 A1 | 5/2013 | Herzog et al. | |

(Continued)

OTHER PUBLICATIONS

A. de Paula, Econometrics of Network Models, in Advances in Economics and Econometrics, pp. 268-323, (2017).

(Continued)

*Primary Examiner* — Eric F Winakur
(74) *Attorney, Agent, or Firm* — Wilson Sonsini Goodrich & Rosati

(57) ABSTRACT

A method of determining structured behavior from network adjacency matrices is described. A method of detecting physiological signals from a subject is described.

19 Claims, 15 Drawing Sheets

(56) References Cited

U.S. PATENT DOCUMENTS

| | | |
|---|---|---|
| 2013/0144140 A1 | 6/2013 | Frederick et al. |
| 2015/0119665 A1 | 4/2015 | Barbour et al. |

OTHER PUBLICATIONS

Ahmad et al., Theory, Instrumentation, and Applications of EPR Oximetry, NIH Public Access Author Manuscript, Chem. Rev.May 12, 2010; 110(5): 3212-3236: doi:10.1021/cr900396q.

Al Abdi et al., Optomechanical imaging system for breast cancer detection, Optical Society of America, vol. 28, No. 12, Dec. 2011, J. Opt. Soc. Am. A.

Albert et al., Error and attack tolerance of complex networks, Nature, vol. 406, Jul. 27, 2000, www.nature.com.

Amalakanti et al. Pulse Oximetry Overestimates Oxygen Saturation in COPD, Respiratory Care, 61, 423-427 (2016).

Arlot et al., A survey of cross-validation procedures for model selection, Statistics Surveys, vol. 4(2010) 40-79, SSN: 1935-7516, DOI:10.1214/09-SS054.

Balarndin et al., (2017) Imaging Brain Function with Functional Near-Infrared Spectroscopy in Unconstrained Environments, Front. Hum.Neurosci. 11:258. doi: 10:3389/fnhum.2017.00258.

Barabási et al., Emergence of Scaling in Random Networks, http://www.sciencemag,org; Science, vol. 286, Oct. 15, 1999.

Barbour et al., Functional Imaging of Autoregulation (no date).

Barbour RL, et al. Hemoglobin state-flux: A finite-state model representation of the hemoglobin signal for evaluation of the resting state and the influence of disease. PLoS One. Jun. 8, 2018;13(6):e0198210. doi: 10.1371/journal.pone.0198210. PMID: 29883456; PMCID: PMC5993307.

Barquero et al., (2014) Neuroimaging of Reading Intervention: A Systematic Review and Activation Likelihood Estimate Meta-Analysis. PLoS ONE9(1): e83668. doi:10.1371/journal.pone.0083668.

Bélanger et al., Real-time diffuse optical tomography based on structured illumination, Journal of Biomedical Optics 15(1), 016006(Jan./Feb. 2010).

Breitkreutz et al., Molecular signaling network complexity is correlated with cancer patient survivability, PNAS, 109, 9209-9212, (2012).

Busch et al., Toward Noninvasive Characterization of Breast Cancer and Cancer Metabolism with Diffuse Optics, pet. the clinics. com,PET Clin 8 (2013) 345-365, http://dx.doi.org/10.1016/j.cpet.2013.04.004.

Calderoni et al., (2016) Rehabilitative Interventions and Brain Plasticity in Autism Spectrum Disorders: Focus on MRI-Based Studies. Front. Neurosci. 10:139. Doi: 10.3389/fnins.2016.00139.

Charles E. Metz, Basic Principles of ROC Analysis, Seminars in Nuclear Medicine, vol. VIII, No. 4 Oct. 1978.

Curtin et al., Evaluation of evoked responses to pulse-matched high frequency and intermittent theta burst transcranial magnetic stimulation using simultaneous functional nearinfrared spectroscopy, Neurophoton.4(4), 041405 (2017), doi: 10.1117/1.NPh.4.4.041405.

David Weininger, Smiles, a Chemical Language and Information System, J. Chemical Information and Computer Sciences 28, 31-36 (1988).

D.D. Thomas, Breathing new life into nitric oxide signaling: A brief review of the interplay between oxygen and nitric oxide, Redox Biol., 5, 225-233 (2015).

D.J.Kominsky et al., Metabolic Shifts in Immunity and Inflammation, J. Immunol. 184, 4062-4068 (2010).

E.A. Rietman et al., Personalized anticancer therapy selection using molecular landscape topology and thermodynamics, Onco target 8,18735-18745 (2017).

E.A. Rietman et al., Thermodynamic measures of cancer: Gibbs free energy and entropy of protein-protein interactions, J. Biol Phys.

Eliza Strickland, Why Mary Lou Jepsen Left Facebook: To Transform Health Care and Invent Consumer Telepathy-IEEE Spectrum,https://spectrum.IEEE.org/the-human-os/biomedical/imaging/why-mary-lou-jepsen-left-facebook-to-transform-healthcare-and-invent-consumer-telepathy.

Fitch et al., Artificial grammar learning meets formal language theory: an overview, Phil. Trans. R. Soc. B (2012) 367, 1933-1955 doi:10.1098/rstb.2012-0103.

G. Oster, Network Thermodynamics, Nature 234, 393-399, (1971).

G.F. Oster, Tellegen's Theorem and Thermodynamic Inequalities, J. Theor. Biol, 32, 219-241 (1971).

Gheorghe et al., A formal language-based approach on biology, Comparative and Functional Genomics, Comp Funct Genom 2004; 5: 91-94.Published online in Wiley Inter Science (http://www.interscience.wiley.com). DOI:10.1002/cfg.364.

Graber et al., Enhanced resting-state dynamics of the hemoglobin signal as a novel biomarker for detection of breast cancer, Medical Physics, 42, 6406 (2015); doi: 10.1118/1.4932220.

Graber et al., Imaging of Spatiotemporal Coincident States by DC Optical Tomography, IEEE Transactions on Medical Imaging, vol. 21,No. 8, Aug. 2002.

Hengen et al., Neuronal Firing Rate Homeostasis is Inhibited by Sleep and Promoted by Wake, 2016, Cell 165, 180-191, Mar. 24, 2016 ©2016Elsevier Inc., http://dx.doi.0rg/10.1016/j.cell.2016.01.046.

H.J. Forman, Redox-signaling: an evolution from free radicals to aging, Free Radic BiolMed., 97, 398-407 (2016).

Hong et al., Reduction of Delay in Detecting Initial Dips from Functional Near-Infrared Spectroscopy Signals Using Vector-Based Phase Analysis, International Journal of Neural Systems, vol. 26, No. 3 (2016)1650012 (16 pages), © World Scientific Publishing Company, DOI: 10.1142/S012906571650012X.

Hu et al. Diet, lifestyle, and the risk of type 2 diabetes mellitus in women. N Engl J Med. Sep. 13, 2001;345(11):790-7.

Ikebata et al., Bayesian molecular design with a chemical language model, J Comput Aided Mol Des (2017) 31:379-391, DOI10.1007/s10822-016-008-z.

J. Lei, et al., Assessing the Healing of Venous Leg Ulcers Using a Noncontact Near-Infrared Optical Imaging Approach, Adv Wound Care, 7, 134-143, (2018).

Jain et al., Artificial Neural Networks: A Tutorial, IEEE Computer, Mar. 1996.

Jayachandran et al., Critical Review of Noninvasive Optical Technologies for Wound Imaging, Advances in Wound Care, vol. 5,No. 8, DOI: 10.1089/wound.2015.0678.

Jäger et al., Formal language theory: refining the Chomsky hierarchy, Phil. Trans. R. Soc.B. (2012) 367, 1956-1970doi:10.1098/rstb.2012.0077.

K.G. Moulakakis et al. "Hyperperfusion syndrome after carotid revascularization", J. Vascular Surg., 49, 1060-1068 (2009).

Komjáthy et al., Lecture Notes for Markov Chains: Mixing Times, Hitting Times, and Cover Times, in Saint Petersburg Summer School, 2012.

Kuphaldt, DC Network Analysis, Chapter 10 in Lessons in Electrical Circuits, vol. I—DC, 5th Ed. Open Book Project(2006).

Lancashire et al., An introduction to artificial neural networks in bioformatics-application to complex microarray and mass spectometrydatasets in cancer studies, Briefings in Bioformatics, vol. 10 No. 3. 315-329,Advance Access publication Mar. 23, 2009.

Lawrence R. Rabiner, A Tutorial on Hidden Markov Models and Selected Applications in Speech Recognition, Proceedings of the IEEE, vol. 77, No. 2, Feb. 1989.

Lindquist et al., Modeling the hemodynamic response function in fMRI: Efficiency, bias and mismodeling, NeuroImage45, S187-S198 (2009).

Mario Beauregard, PhD., Functional neuroimaging studies of the effects psychotherapy, http://www.dialogues-cns.org,Dialogues in Clinical Neuroscience—vol. 16, No. 1, 2014.

Mazhar et al., Structured illumination enhancesresolution and contrast in thick tissue fluorescence imaging, Journal of Biomedical Optics, 010506-1, Jan./Feb. 2010, Vo. 15(1).

Mehmood et al., Exploration of prominent frequency wave in EEG signals from brain sensors network, Int. J.Distributed Sensor Networks 2015, Article ID 386057 (2015).

(56) References Cited

OTHER PUBLICATIONS

M.J. Stampfer et al., "Primary prevention of coronary heart disease in women through diet and lifestyle" N Engl J Med, 343, 16-22 (2000).
Omar et al., A survey of information entropy metrics for complex networks, Entropy 22,doi:10.3390/e22121417 (2020).
Open Science Framework: Resting-State Simultaneous Dual-Breast Imaging. OSF Resting-State Simultaneous Dual-Breast Imaging.
Pavlopoulos et al., Using graph theory to analyze biological networks, Bio Data Mining 2011, 4:10.
PCT Application No. PCT/US2017/056643—International Search Report and Written Opinion dated Dec. 14, 2017.
Pei et al., Influence of systematic errors in reference states on image quality and on stability of derived information for DC optical imaging, Applied Optics 40, 5755-5769 (2001).
Pereda et al., Gap junction-mediated electrical transmission: Regulatory mechanisms and plasticity, Elsevier, Biochimica et Biophysica Acta, journal homepage: http://www.elsevier.com/locate/bbamem,Biochimica et Biophysica Acta 1828 (2013) 134-146.
Piper et al., A wearable multi-channel fNIRS system for brain imaging in freely moving subjects, Elsevier, Neuroimage, journal homepage: http://www.elsevier.com/locate/ynimg,Neuroimage 85 (2014) 64-71.
R. Kazemi, Entropy of weighted graphs with the degree-based topological indices as weights, Math. Comput. Chem. 76, 69-80 (2016).
R. Kwasinski et al., Tissue Oxygenation Changes to Assess Healing in Venous Leg Ulcers Using Near-Infrared Optical Imaging, Adv Wound Care, 8, 565-597, (2019).
R.B. Buxton, The physics of functional magnetic resonance imaging (fMRI), Reports on Progress in Physics 76, 096601 (2013).
Rohart et al., mixOmics: An R package for 'omics feature selection and multiple data integration, PLoS Computational Biology 13: e1005752 (2017).
Saliba et al., Functional near-infrared spectroscopy for neuroimaging in cochlear implant recipients, Elsevier, Hearing Research, journal homepage: http://www.elsevier.com/locate/heares,Hearing Research 338(2016)64-75.
Sarti et al., Cytochrome c oxidase and nitric oxide inaction: Molecular mechanisms and pathophysiological implications, Elsevier,Biochimica et Biophysica Acta, journal homepage: www.elsevier.com/locate/bbabio,Biochimica et Biophysica Acta 1817 (2012) 610-619.
Schilling et al., The underlying pathway structure of biochemical reaction networks, Proc. Natl. Acad. Sci. USA. Vol. 95, pp. 4193-4198, Apr. 1998, Biochemistry, Engineering.
Schilling et al., Theory for the Systemic Definition of Metabolic Pathways and their use in Interpreting Metabolic Function from a Pathway-Oriented Perspective, J. theor. Biol. (2000) 203, 229-248, doi: 10.10006/jtbi.2000.1073.
Schmitz et al., Design and implementation of dynamic near-infrared optical tomographic imaging instrumentation for simultaneous dual-breast measurements, Applied Optics, vol. 44, No. 11, Apr. 10, 2005.
Schuh et al., Imaging Blood Vessel Morphology in Skin: Dynamic Optical Coherence Tomography as a Novel Potential Diagnostic Tool in Dermatology, Dermatol Ther (Heidelb) (2017) 7:187-202, DOI10.1007/s13555-017-0175-4.
Segal, Integration and Modulation of Intercellular SignalingUnderlying Blood Flow Control, J. Vasc. Res., 52, 136-157 (2015).
Sergio Fantini, Dynamic model for the tissue concentration and oxygen saturation of hemoglobin in relation to blood volume flow velocity, and oxygen consumption: Implications for functional neuroimaging and coherent hemodynamics spectroscopy (CHS), Elsevier, Neuroimage, journal homepage: http://www.elsevier.com/locate/ynimg, Neuroimage 85 (2014) 202-221.
Sheppard, Analysis of a Single Time Series, Enders (2004), Hamilton (1994).
Shinji Umeyama, An Eigen decomposition Approach to Weighted Graph Matching Problems, IEEE Transactions on Pattern Analysis and Machine Intelligence, vol. 10, No. 5, Sep. 1988.
Sitaram et al., Closed-loop brain training: the science of neurofeedback, Nature Reviews, Neuroscience, Feb. 2017, vol. 18.
S.M. Goias et al., Gibbs free energy of protein-protein interactions correlates with ATP production in cancer cells, J. Biol. Phys., 45, 423-430 (2019).
Somvanshi et al., A conceptual review on systems biology in health and diseases: from biological networks to modern therapeutics, Syst Synth Biol (2014) 8:99-116, DOI 10.1007/S11693-013-9125-3.
S.S. Segal, Regulation of Blood Flow in the Microcirculation, Microcirc. 12, 33-45, 2005.
Stephan et al., Bayesian model selection for group studies, Elsevier, Neuroimage, journal homepage: http://www.elsevier.com/locate/ynimg,Neuroimage 46 (2009) 1004-1017.
Steppan et al., Cerebral and tissue oximetry, Best Practice Res. Clin. Anaesthes. 28, 429-439 (2014).
Taroni et al., (2015) Breast Tissue Composition and its Dependence on Demographic Risk Factors for Breast Cancer: Non-Invasive Assessment by Time Domain Diffuse Optical Spectroscopy. PLoS ONE 10(6): e0128941. doi: 10.1371/journal.pone.0128941.
Taroni et al., Non-invasive optical estimate of tissue composition to differentiate malignant from benign breast lesions: A pilot study, www.nature.com/scientificreports,7.40683, DOI: 10.1038/srep40683.
Tony R. Kuphaldt, Lessons in Electric Circuits, vol. I-DC, Fifth Edition, last update Oct. 18, 2006.
Tromberg et al., Predicting Responses to Neoadjuvant Chemotherapy in Breast Cancer: ACRIN 6691 Trial of Diffuse Optical Spectroscopic Imaging, downloaded from cancerrres.aacrajournals.org on May 12, 2017. Published Online First Aug. 15, 2016; DOI: 10.1158/0008-5472. CAN-16-0346.
Vaquero et al., Positron Emission Tomography: Current Challenges and Opportunities for Technological Advances in Clinical and Preclinical Imaging Systems, Annu. Rev. Biomed. Eng. 2015. 17:385-414.
Wang et al., Electrochemical Sensors for Clinic Analysis, State Key Laboratory of Industrial Control Technology, Institute of Advanced Process Control, Zhejiang University, Hangzhou 310027, P.R. China, Sensors2008, 8, 2043-2081, ISSN 1424-8220, ©2008 by MDPI, www.mdpi.org/sensors.
Wang et al., "Photoacoustic Tomography," Chapter 12 in L.-V. Wang and H. Wu, Biomedical Optics: Principles and Imaging (Wiley-Interscience, 2007), pp. 283-317).
Wang et al., Photoacoustic Tomography: In Vivo Imaging from Organelles to Organs, Mar. 23, 2012, Vil. 335, Science, http://www.sciencemag.org.
Wylie et al., Using co-variations in the Hb signal to detect visual activation: A near infrared spectroscopic imaging study, Elsevier,Neuroimage, journal homepage: http://www.elsevier.com/locate/ynimg, Neuroimage 47(2009) 473-481.
Y. Yamada et al., Time-Domain Near-Infrared Spectroscopy and Imaging: A Review, Appl. Sci., 9, 1127, (2019).
Yoshihara et al., Oxygen imaging of living cells and tissues using luminescent molecular probes, Elsevier, Journal of Biochemistry and Photobiology C: Photochemistry Reviews 30 (2017) 71-95, journal homepage: http://www.elsevier.com/jphotochemrev.
Yoshino et al., Vector-based phase classification of initial dips during word listening using near infrared spectroscopy, Neuro Report 2012, 23:947-951, vol. 23, No. 16.
Yuen et al., Intrinsic frequencies of the resting-state fMRI signal: The frequency dependence of functional connectivity and the effect of mode mixing, Frontiers Neurosci. 13,900 (2019).
Z. Ahmed, Practicing precision medicine with intelligently integrated clinical and multi-omics data analysis, Human Genetics, 14:35 (2020).
Zhan et al., A Window into the Brain: Advances in Psychiatric fMRI, Hindawi Publishing Corporation, BioMed Research International, vol. 2015, Article ID 542467, 12 pages, http://dx.doi.org/10.1155/2015/542467.

* cited by examiner

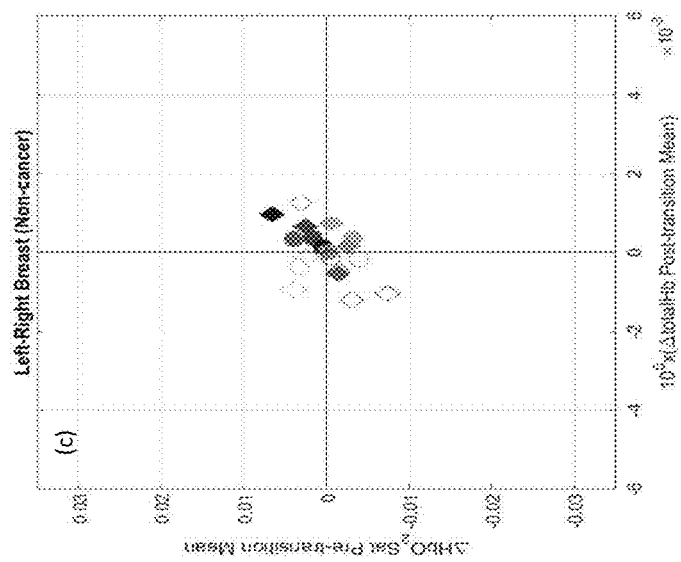
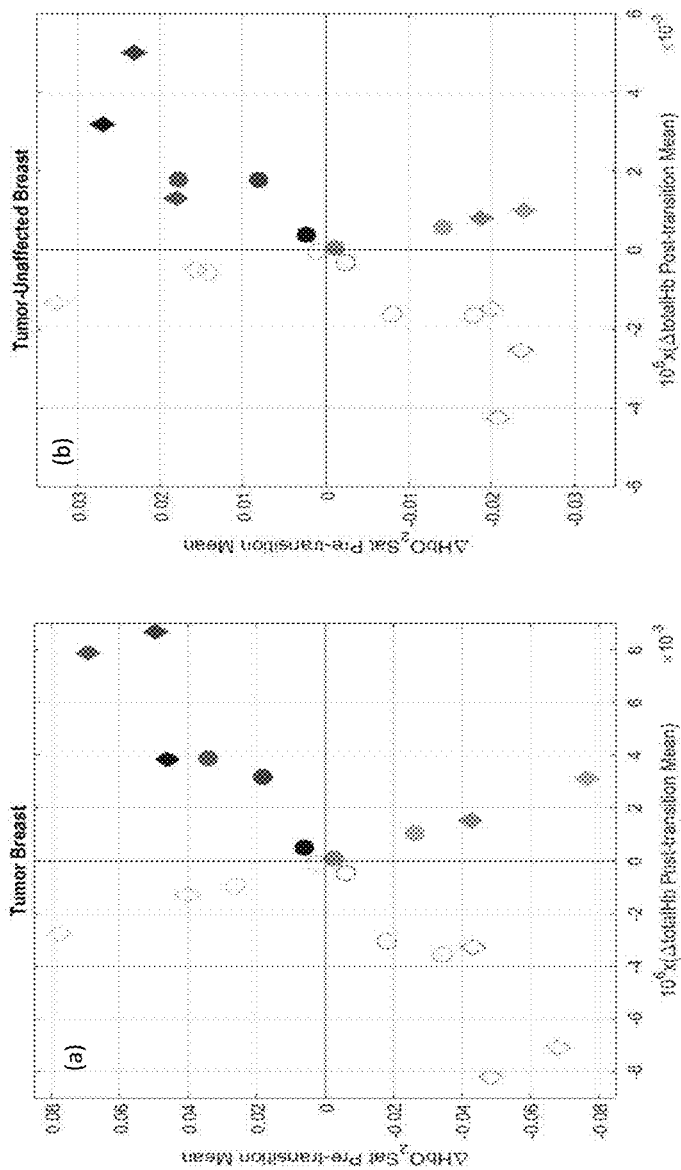
FIG. 7A  FIG. 7B  FIG. 7C

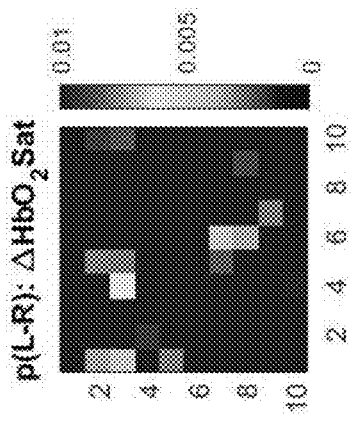
FIG. 8D
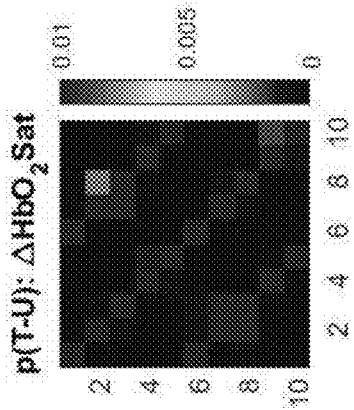
FIG. 8C
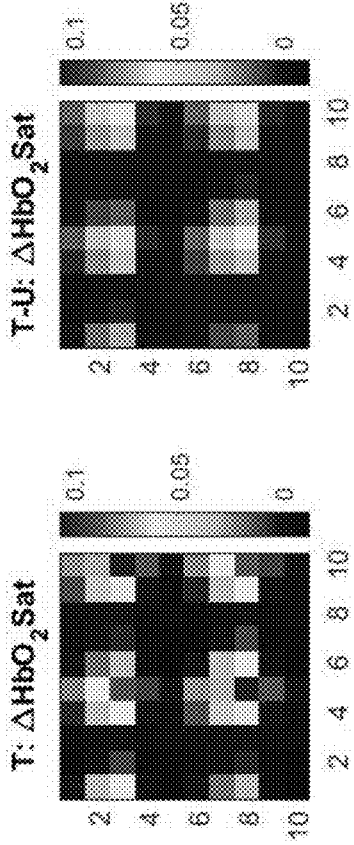
FIG. 8B
FIG. 8A
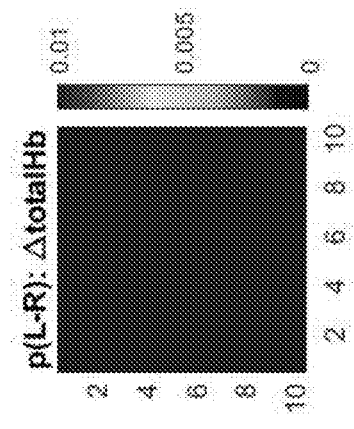
FIG. 8H
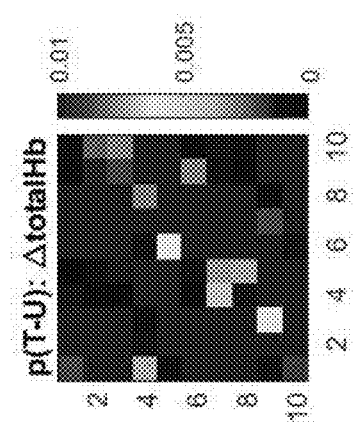
FIG. 8G
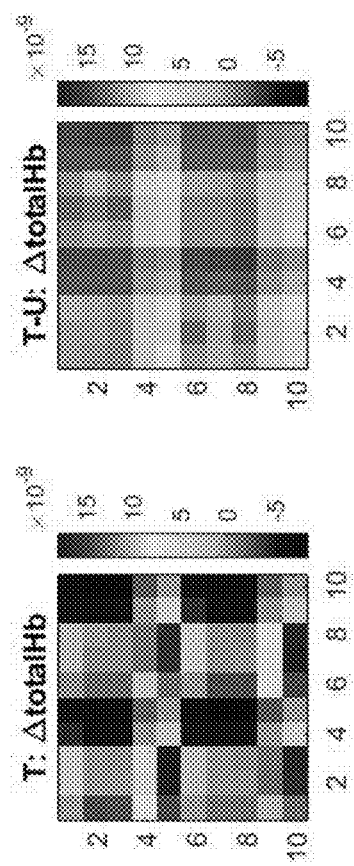
FIG. 8F
FIG. 8E

METHOD FOR UNCOVERING DEEPLY HIDDEN ENZYME-LIKE BEHAVIORS FROM PHYSIOLOGICAL TIME-SERIES MEASURES FOR DISEASE DETECTION, MONITORING AND OTHER APPLICATIONS

CROSS REFERENCE

This application claims the benefit of U.S. Provisional Application No. 63/007,086, filed Apr. 8, 2020, which is incorporated herein by reference in its entirety.

BACKGROUND

Homeostatic influences on resting-state behaviors reflect actions of a prevailing epigenetic landscape that impose adjustments to short-term behaviors about the longer time-scale behaviors indicative of the steady-state, for which the said hidden features can be defined from the applied network description. Thus, capabilities of evaluating tissue function affected by oxygen homeostasis and chronic disease that can be favorably applied while advancing the goals of personalized medicine, could be useful in determining hidden, structured behavior.

INCORPORATION BY REFERENCE

Each patent, publication, and non-patent literature cited in the application is hereby incorporated by reference in its entirety as if each was incorporated by reference individually.

SUMMARY OF THE INVENTION

The present invention outlines a methodological approach wherein organized higher-order behaviors, which are reflective of complex time-dependent self-organizing systems but commonly are hidden by low-order representations, can be identified from examination of two or more co-dependent behaviors whose coefficients reflect time-average values obtained from a network description of said system wherein such coefficients constitute measures of different features of a time-series measure. Extension to biological applications follows from the understanding that homeostatic influences on resting-state behaviors reflect actions of a prevailing epigenetic landscape that impose adjustments to short-term behaviors about the longer time-scale behaviors indicative of the steady-state, for which the said hidden features can be defined from the applied network description.

Because the applied methodology supports adjustment to descriptions of network properties, it is anticipated that a wealth of previously hidden organized behaviors can be defined that reflect the actions of homeostatic influences that themselves are dependent on the said landscape. Also, adding to such information is associated network-dependent adjacency matrices that are shown to have a high degree of independence. Whereas the preferred embodiment speaks to capabilities from a representative tissue under the influence of a representative chronic disease using a selected sensing approach, it is expressly recognized that the derived methodology is applicable to any tissue type and can be extended to any class of physiological time-dependent measure having exogeneous or endogenous origins (e.g., bioelectric, hemodynamic, acoustic, thermographic, impedance).

DESCRIPTION OF RELATED ART

Representing more than simply the absence of disease, maintenance of a healthy lifestyle requires attention to a host of factors that include remaining active, avoiding circumstances that generate physiological stress, and having a balanced diet. This understanding is supported by the evidence that >90% of diabetes mellitus [1] and >80% of coronary disease [2] cases can be prevented through adjustment of lifestyle choices such as moderate-to-vigorous physical activity, healthy diet, moderate alcohol consumption, maintaining a normal body mass index (BMI), and avoiding tobacco. Either through insufficient attention to these factors, having a genetic predisposition to disease, or exposure to infectious agents, our everyday lifestyle is filled with circumstances that make attention to such details challenging.

Among the myriad of biological processes affected by both a healthy lifestyle and disease are factors impacting physiological homeostasis. Serving as a self-regulating process, homeostasis is often achieved through multiple interacting mechanisms having a hierarchical structure. For instance, at least three mechanisms are known to affect the process of oxygen homeostasis operating on different spatial and temporal time scales. Having systemic action and generating nearly immediate feedback modulation is the homeostatic regulatory system that comprises $pO_2$ and $pCO_2$ as regulated variables, the brain stem as the control center, the respiratory and diaphragm muscles as effectors, and central and chemoreceptors as sensors. Acting through autonomic mechanisms, efferent sympathetic signaling coupled to the same system serves to adjust the tone of resistance vessels, thereby adjusting blood pressure in concert with local feedback mechanisms that leverage release of vasodilatory autacoids (e.g., nitric oxide and prostacyclin), thus enabling local tissue autoregulatory control of oxygen/nutrient delivery [3]. While details of this coupled behavior vary with tissue type, the effect is to achieve a functional hyperemia upon increased metabolic demand. Also exerting coordinated systemic and local tissue effects, but on a longer time scale, are the pleiotropic actions of hypoxia inducible factors (HIFs) that act to modulate tissue oxygen supply-demand balance through adjustment of hundreds of transcriptional elements.

Among metazoan organisms, it is further understood that strongly affecting homeostasis is the reliance on a host of reductive mechanisms involving the utilization of molecular oxygen, which serve to drive ATP formation, the innate immune response, and the generation of reactive oxygen species (ROS) and reactive nitrogen species (RNS). In turn, ROS and RNS exert control over signaling cascades in ways that can effect hormetic responses, i.e., the same compound will either repress or augment disease processes, depending on its concentration-dynamic impact. Furthermore, because oxygen is not stored by tissue, any factor impeding its adequate delivery or utilization by tissue can produce immediate concerns.

Given the criticality of oxygen delivery to tissue, a plethora of strategies have been established, in various medical subfields that integrate oximetry measures within a host of other standard-of-care procedures. Said procedures often provide for immediate guidance for necessary corrective actions in the form of delivering supplemental oxygen, attending to concerns regarding adequacy of total hemoglobin (Hb) blood content (which, if insufficient, warrants a blood transfusion), adequacy of cardiac output, or procedures directed to correcting acute blockages of blood flow, among others.

Whereas these procedures are well understood and supported by robust technologies, the focus of the interventions overwhelmingly speak to elements of oxygen homeostasis in acute-care situations. Currently not available, in any generalizable form, are capabilities of evaluating tissue function affected by oxygen homeostasis and chronic disease that can be favorably applied while advancing the goals of personalized medicine. This includes noninvasive longitudinal monitoring, capabilities for evaluating essentially any tissue type, measures performed in favorable environmental settings and access to key classes of information (e.g., network behaviors) while also extending the utility of other forms of time-dependent physiological measures.

In the following, the principal elements that frame the potential strategies capable of addressing this need are reviewed.

Factors Affecting Oxygen Delivery to Tissue:

Disruption of oxygen homeostasis can lead to serious and life-threatening conditions, such as occurs during a heart attack or stroke. Similarly, acute trauma, causing either blood loss or crushing injury, can produce severe disruptions in oxygen availability that can also be life threatening. These understandings extend to a host of disease states and other manipulations in response to specific maneuvers or actions of drugs that may adversely affect oxygen delivery.

For instance, in many forms of cancer, the phenotype of enhanced angiogenesis is commonly seen. However, the vessels that are formed do not have a normal architecture; Instead, they typically are distended, tortuous and leaky, leading to increased interstitial pressures. The combined effect is that, despite the presence of abnormally high vascular densities, oxygen availability is often insufficient, leading to hypoxia. Also, commonly seen in cancer is a sustained inflammatory response. For instance, Graber et al. [4] showed convincing evidence that this feature can be detected using near infrared spectroscopy (NIRS), serves as a biomarker for the presence of cancer, and can be identified under resting-state conditions.

Similar outcomes are seen in other forms of chronic disease, although for different reasons. For instance, vasculo-occlusive disease, such as occurs in late-stage diabetes, reduces oxygen availability as a consequence of occlusion of small vessels, and impedes vascular endothelial cell function, thereby reducing the effectiveness of feedback mechanisms. The net effect is a generalized state of hypoxia in affected tissues, with reduced organ function.

Acting as a stressor, the state of hypoxia can trigger compensatory mechanisms that themselves can lead to added morbidity. Commonly seen is an inflammatory response. While acute inflammatory responses, for example to fight off a local infection, are normal and resolve without lasting effects, chronic inflammation can trigger other disorders. Among these are the secondary influences associated with autoimmune diseases, such as occurs in multiple sclerosis. Sustained inflammation can adversely affect the delivery of pharmaceutical agents to tissue, making them less effective due to increased diffusion lengths. It can also lead to hypoxic conditions as a consequence of increased interstitial pressures. This has important implications for the effectiveness of radiotherapy treatments.

Beyond concerns arising from disease, a variety of clinical interventions can affect oxygen delivery in ways that either lead to added morbidity, or impair the ability of the applied intervention to have the intended effect. For instance, a rare but serious complication of carotid revascularization following carotid endarterectomy or carotid stent placement is hyperperfusion syndrome. Believed to result from either baroreceptor reflex failure or impairment to microvascular autoregulation, excessive reperfusion leads to severe headache, seizures, and in some cases, intracranial hemorrhage [5]. Also of general concern are the occult initial effects that can lead to compartment syndrome following injury to soft tissues. When present and untreated, the ensuing tissue ischemia caused by excessive interstitial pressures can rapidly lead to non-viability of a limb requiring amputation or, in some instances, renal failure and death.

Yet another commonly encountered concern is the unintended side effects of drugs. Depending on the drug, the concern presented can be excessive toxicity (e.g., chemotherapy treatments) resulting from induced metabolic imbalances that affect liver, kidney or lung function, unexpected changes in blood pressure, or psychiatric effects, among others. In many instances, a secondary consequence of these influences is disturbances in oxygen delivery or in its utilization by key organs. In others, the aim of the drug can be to modify oxygen utilization, such as occurs with Meldonium, a banned drug used to enhance athletic performance, whose action is thought to favor carbohydrate metabolism over the more oxygen-consuming metabolism of fat.

Appreciating the importance that changes in oxygen delivery have on tissue function also plays a key role in optimizing the performance of neural implants and guiding diagnosis of various neuropsychiatric disorders. A common strategy is to acquire measures of the hemodynamic response that accompanies neuroactivation. Being strongly coupled through the action of astrocytes, activation of neurons in response to, for example, sensory inputs, motor activation or cognition, leads to a local functional hyperemia. When measured using functional magnetic resonance techniques (fMRI), this signal, known as the Blood Oxygen Level Dependent (BOLD) response, has been used to characterize the spatiotemporal responses of the brain to a wide range of stimuli. While such measures have been applied to assess psychiatric disorders [6], and various treatment interventions [7-9], they are generally considered unsuitable for evaluation of neural implants. Instead, expected event-related changes in oxygen utilization following, for example, cochlear implantation, can be evaluated by noninvasive optical methods such as NIRS [10].

Still other applications being developed from measures sensitive to changes in oxygen utilization by the brain are those based on biofeedback or response to neuromodulation [11]. One form of neuromodulation is the changes produced to the short- and long-term synaptic profiles of the brain in response to applied pulsed magnetic fields. This strategy, known as transcranial magnetic stimulation (TMS), is used in the clinical management of depression and other psychiatric diseases, in recognition that these disorders are causally affected by aberrant synaptic profiles. However, while such treatments can be effective, there is a need for more individualized treatment protocols, an aim potentially achievable by adoption of the methods described herein.

To minimize uncertainties of treatment, measures of the TMS-induced hemodynamic response to neuro-activation seen during treatment sessions, or shortly afterwards, have been proposed as a guide to treatment protocols under the hypothesis that the effectiveness of these treatments varies with the amplitude of this induced response [12]. Another form of neuromodulation that can potentially benefit from individual guidance to applied protocols is treatments involving electrical stimulation of the brain, such as can be achieved by transcranial direct-current stimulation (tDCS). As in the TMS case, real-time access to induced responses allows for implementing biofeedback-dependent protocols for investigating the effects being produced by the applied treatments.

In summary, the critical interdependence of tissue function and oxygen homeostasis predisposes tissues of various types toward multiple forms of sensitivity to disease, and to respond to a wide range of manipulations, some of which may serve to guide treatment or to improve the performance of assistive devices. This understanding motivates specific sensing approaches that can be directed toward the key factors that determine oxygen homeostasis.

Technologies and their Uses for Evaluating Factors Affecting Oxygen Delivery to Tissue:

Recognition that various forms of integrated physiological behaviors are linked to oxygen homeostasis has prompted the development of a range of sensing capabilities and methods intended to explore features of interest. Among these are the methods of positron emission tomography (PET) [13], electron paramagnetic resonance (EPR) oximetry [14], electrochemical electrode methods [15], the MR-BOLD technique, and a variety of optical methods, including oximetry-based techniques (pulse oximetry and tissue oximetry) that may include additional signal transduction, as occurs in luminescence [16] or in the photoacoustic effect [17]. Separate from these are techniques sensitive to blood flow. While the latter measures often are useful in themselves, they do not directly determine oxygen availability or its utilization. Also, while the former techniques can aid in the interpretation of measures that assess tissue oxygen levels or features of the Hb signal, their use can be affected by technology-dependent added attenuation of acoustic signals by bone (notably, the cranium), limited sensitivity to the microvascular bed, or the added cost associated with the requirement for complex sensing resources (e.g., Diffuse Correlation Spectroscopy).

Among these methods, the MR-BOLD technique and various forms of optical sensing have shown the greatest promise. However, significantly limiting the former are its high costs, unsuitability for examining vulnerable populations (e.g., infants, individuals with embedded metal, subjects who are claustrophobic), and sensitivity to only a limited portion of the information that identifies the principal phenomenology of tissue oxygen utilization. Being sensitive to only variations in deoxyhemoglobin, it can be unclear whether changes in the BOLD signal are due to changes in blood volume or blood oxygenation. In contrast, optical-based oximetry methods, which include various implementations of near-infrared sensing, allow for detection of the full complement of the Hb signal that includes both its oxygenated (oxyHb) and deoxygenated (deoxyHb) forms and other commonly computed quantities; total Hb, Hb oxygen saturation ($HbO_2Sat$) and Hb-tissue oxygen exchange ($HbO_2Exc$).

The method of pulse oximetry has the longest history of clinical experience. Diffuse transmission measurements are acquired from small appendages, from which measures of $HbO_2Sat$ are reported. Typically employed are sources that emit two wavelengths of light on either side of the 805 nm isosbestic point in the Hb spectrum. Conversion of light intensity to measures of the relative change in Hb levels is achieved using a modified Beer-Lambert equation that includes a differential pathlength factor to account for pathlength increases caused by scattering. Alternatively, this conversion can be accomplished by computing solutions to an inverse problem based on operators derived from the radiative transport equation or from suitable approximations.

While pulse oximetry measures are typically accomplished using CW-NIRS techniques, equivalent measures can be obtained using frequency-domain illumination-detection methods sensitive to expected time delays of light propagation in tissue caused by scattering, or by ultrafast methods that trace the time-dependent intensity profile [18]. The presence of other intrinsic factors in tissue that influence light attenuation in the NIR spectral region can motivate use of additional wavelengths of light. Such factors include, but are not limited to, absorption by water, lipid, melanin and mitochondrial cytochrome c-oxidase, and the scattering of light by tissue.

Similar to the pulse oximetry method are measures obtained from similar sensors but applied to bulk tissues for measuring relative tissue oxygenation. An example here is the INVOS monitor by Coviden, which samples back-reflected light.

In principle, roughly equivalent measures can be achieved from strategies that detect the fate of light absorption by tissue, resulting in its conversion to heat, thereby generating a propagating pressure wave that can be observed using acoustic sensing methods. Known as the photoacoustic effect, this technique supports similar types of optical inspection of tissues, while offering the advantages of deeper signal penetration and improved resolution of recovered images. Also capable of assessing the different forms of hemoglobin are recently described holographic methods that discriminate features of diffused light [19]. Likewise, the methods of the present invention could be used for analysis of time-series data recorded in dynamic optical coherence tomography applications (OCT), provided that this technique is modified to illuminate the target tissue with two or more wavelengths of light instead of the commonly employed single-wavelength approach [20]. Further, when acquired as a time-series, methods of the present invention also could be applied to analyze data recorded by structured illumination measurements (aka, spatial frequency domain) [21], which has been shown to have promising utility for assessing the severity of burns [22].

Also considered by the NIRS technique, but involving use of arrays of optical sensors, are measures intended to explore the phenomenon of neurovascular coupling and the connectivity properties of the brain. These measures have captured growing attention by the experimental psychology community, in part because they can operate in unconstrained environments [23,24].

Measures of the time-evolving Hb response of the brain to behavioral tasks, or of coordinated behaviors that arise from its connectome properties, can be accomplished using an array of optical sources and detectors that are configured in some defined alternating pattern and are placed in direct contact with body tissues. Typically, sensing hardware is introduced into a conforming fabric cap that is mechanically supported by added stabilizers or by use of more rigid support structures. Back-reflection measures are acquired with detectors placed at a distance of approximately 3-4 cm from a source, and, recognizing that the maximum penetration depth of light emerging from tissue varies with distance from a source, additional short-distance measures intended to isolate contributions from more superficial tissues (e.g., scalp) also can be considered.

Related measures are those that use arrays of NIRS sensors on bulk tissues such as the breast and other peripheral tissues. In these cases, the sensing arrays may comprise a low-profile pad containing light emitters (e.g., LEDs, laser diodes or vertical cavity lasers) and receivers [e.g., silicon photodiodes (SiPD), avalanche photodiodes (APD), photomultipler tubes (PMT), silicon photomultipler, (SiPM), single photon avalanche photodiode (SPAD [18]). Owing to its relatively low heme content, full transmission and intermediate illumination-detection arrangements are feasible for breast tissue. Indeed, as shown by Al abdi et al., capture of full tomographic 3D image time series measures is achievable [25].

To record a time series measurement, sensing arrays can be operated by employing schemes that range from full source-multiplexing, in which each source location is illuminated sequentially, to full frequency encoding, which allows for simultaneous detection of light from multiple sources for each detector position. The driving electronics for these arrays can be housed locally in the form of a compact wireless amplifier, or employ a tether that transmits and receives electrical and timing signals from a desktop amplifier. Also feasible are non-contact measures wherein the target tissue is illuminated by a collimated source or with broad-area structured-illumination methods [26]. Non-contact optical sensors can include discrete sensors (e.g., SiPD, APD, PMT, SiPM, SPAD) or area arrays (e.g., charge-coupled device (CCD)).

A principal focus of breast studies with NIRS has been for early detection of breast cancer [27] as a confirmatory diagnostic method [28], and to assess the effectiveness of neoadjuvant therapies [29]. Experience has shown that while the optical method is sensitive to larger tumors, detection of small tumors is notably more challenging. In an effort to overcome this, and recognizing that tumors are often more stiff than surrounding tissue, one strategy considered has been to employ the Valsalva maneuver [30] or applied force (Al abdi et al., [25]), with the expectation that the response from affected tissue will differ in some discernible way from that of healthy tissue.

In summary, techniques are available that are sensitive either directly to tissue oxygen levels or to surrogate measures that include properties of Hb and blood flow measures. Among the optical techniques, available are varying illumination and detection methods and strategies for signal transduction that endow added signal penetration or sensitivity. Having the most favorable flexibility, cost, and form-factor features are CW NIRS measures, whose devices can be applied either to small appendages or to bulk tissues using sensing arrays.

Complementing such capabilities in ways that can discern the impact that chronic disease has on oxygen homeostasis is the adoption of data analysis strategies and experimental techniques that support disambiguation of signal features. Analysis Methods and Experimental Techniques Applied to Evaluate Features Linked to Oxygen Delivery to Tissue:

Independent of the sensing techniques used to explore the Hb signal are various analysis methods employed to isolate features of interest. Motivating a particular strategy is the expectation that selected features are recoverable with sufficient fidelity to allow for their useful detection, often with the goal of monitoring how values may change in response to treatment or whether measured values exceed expected limits. However, in many instances, target features of interest can be obscured by artifact or by the presence of other signals that overlap with these features, but do not originate from the tissue of interest. The origin of these overlapping signals can be traced to contributions from spatial features of tissue, or from intrinsic dynamic behaviors that overlap with the target feature.

An example of the former is the use of near-distance detector measures that preferentially sample light confined to the superficial elements of tissue, thereby allowing for regression of these signals from those sampled by detectors positioned at longer distances, which unavoidably, include contributions from near-surface and deeper-lying tissues. Roughly equivalent outcomes can be achieved in cases where high-density sensor arrangements are applied and the acquired measures are processed using tomographic reconstruction methods. The advantage of tomography is the improved ability to resolve features that have been spatially convolved.

In situations where signal convolution is due to overlapping temporal behaviors, target features may be resolvable if background signals exhibit different frequency structure, or if the temporal profile of background signals is substantially uncorrelated with or independent of target behaviors. Recognizing that neither of these conditions may be evident in instances where the aim is to detect neuroactivation in response to stimuli, attention to details of the experimental protocol has shown that effective strategies can be found. Because the timing of stimuli can be made mainly independent of roughly periodic intrinsic vascular signals, use of simple event averaging serves to suppress these contributions. Further, because the details of the protocol are known, its timing can be used to synchronize response measures to applied regression methods. A common strategy is the method known as statistical parametric mapping (SPM), which employs the general linear model to determine whether goodness of fits of a defined function (usually a form of a gamma variate function) to the measured response exceeds statistical expectations.

Yet other methods have the aim to appreciate whether intrinsic temporal features may be correlated, but are spatially distinct. Simply applied are computations of time correlation, which reveal the correlation value as a function of the time lag. Recognizing that the propagation of neural signals produces a network of signaling whose features are spatially distinct and often directed, other methods can be applied that are sensitive to this property. Notable is the method of Granger Causality, which can reveal these features in instances that are directly observable, and the method of Dynamic Causal Modeling, which can additionally recognize these in cases where some network features are hidden.

Another experimental technique used to investigate properties of the Hb signal in tissue is perturbation methods. When employed, their aim is to extract some measure(s) of system response that serves to differentiate behaviors attributable to different subject groups or types or details of applied perturbation. The form of the perturbation can vary significantly and includes exploring the response to actions of drugs, to various stimuli or to physical maneuvers such as inflation of a pressure cuff and respiratory challenges, among others. This class of maneuvers can be applied over a wide range of tissue types. For instance, because diabetes affects the vascular endothelium, hyperemia in response to cuff inflation (reactive hyperemia) is often attenuated. Also considered have been respiratory maneuvers that lead to transient engorgement of the venous tree (e.g., Valsalva maneuver), which upon release can generate disease-sensitive temporal profiles [30]. In the case of behavioral studies intended to explore brain function, perturbation methods frequently involve measuring responses to specific stimuli.

A particular advantage of this approach is the expectation that often it is not necessary to have prior knowledge of the details governing system behavior; instead, it is sufficient to consider only the response. In many instances the expected response is some change in signal amplitude tied to the applied perturbation, which often can be easily discerned. In other situations, where the effect seen is either not acute or is more subtle, detection can be more challenging. Useful strategies here include the above-mentioned methods for resolving overlapping temporal behaviors, especially those that may be uncorrelated or independent.

In practice, the hypothesis that observable responses can aid in classifying and quantifying features that may support, for example, disease detection or discrimination, can be complicated should the response itself depend on other factors such as the presence of common subclinical factors such as arterial vascular disease. Yet another concern is that, while offering flexibility, the details of discerning which amplitude, duration and type should be applied to isolate useful features can require systematic exploration and refinement of methods, which can require significant computational support. Still another confound is the influence of expected variability in subject compliance should the protocol require this, or in the details of how a target tissue (e.g., breast, arm, leg), may respond owing to inter-subject variability in boundary conditions resulting from varying tissue dimensions.

While perturbation methods can be useful, experience shows that there are many circumstances where they are not easily employed, or are contraindicated, or are simply infeasible. Examples include hospitalized patients who may be immobilized or unconscious, and patients whose participation in a specific maneuver is deemed unsafe (e.g., subjects with severe heart disease), among others. The form of these restrictions does not necessarily depend on invoking perturbations that may require extreme exertions or are potentially hazardous. For instance, obviously challenging are protocols that require responses from someone who is unconscious. Nevertheless, there are circumstances in which the state of consciousness can be ambiguous. This is the case in subjects who are minimally conscious due to the effects of various diseases.

Separate from perturbation methods are methods sensitive to the fractional saturation of oxygen binding to Hb, or to functional dependencies that arise from the coupling between tissue oxygen demand and its vascular supply. The former is represented by the method of pulse oximetry which is achieved from measures of the amplitude of the arterial pulse relative to the DC signal amplitude. While useful, its performance can be notably degraded in instances of poor peripheral perfusion or severe pulmonary disease [31]. Also common are estimates of the relative changes in tissue oxygen saturation which, when subtracted from the pulse oximetry value, offers a measure of the relative oxygen supply-demand balance in tissue. In practice, this measure can exhibit a high degree of variance, likely stemming from the variable contributions of the vascular bed at a given tissue site and level of perfusion. Indeed, systematic studies comparing the performance of such measures acquired by different instruments from commercial vendors has revealed variations as high as +/−10%, leading to the conclusion that only individual trend monitoring is feasible [32].

One approach to gaining added understanding of how best to balance experimental strategies with uncertainties arising from incomplete knowledge of disease effects is to invoke use of physiological models [33]. As considered by Fantini [33], available are models that relate easily measurable properties of the Hb signal to intrinsic vascular-compartment-specific features and other quantities expected to impact tissue oxygen utilization. While evidence of consistency between the measured quantities and selected input values to the model was shown (forward modeling), far more challenging is the reverse situation where the goal is to estimate the intrinsic, non-observable quantities from time-varying measures of the Hb signal (inverse modeling). One concern regards the expected robustness of such solutions, given limited availability of model parameters for an arbitrary tissue and understanding of how these depend on the presence of disease. Another is the inherent limitations arising from the obvious mismatch in dimensionality (several orders of magnitude) between the scale on which the computed quantities are considered (microvascular bed) and the scale on which the measurements are actually made (typically cm-scale resolution).

Whereas the composite of approaches listed to explore the Hb signal have proven useful in some contexts, mainly absent are strategies that can be applied when the considered methods are either deemed infeasible, or have other limitations as noted, especially with regard to measures involving peripheral tissues. Also recognized is an overall limited ability to quantify factors that modulate elements of oxygen supply-demand balance in ways that recognize improved states of health or particular features of disease such as the impact of sustained inflammation. Whereas evidence of strategies sensitive to elements of these processes are considered herein, clear from these findings is that there is much more complexity tied to the dynamics of the Hb signal than is being captured by currently deployed oximetry techniques.

In summary, although a number of key features-of-interest regarding properties of the Hb signal are accessible (e.g., strategies to isolate spatially or temporally convolved signals, arterial oxygen saturation, trend monitoring of relative oxygen supply-demand balance, measures sensitive to neuroconnectivity, vascular compartment-specific features, etc.) and can be supplemented by adoption of perturbation methods, unresolved are instances wherein the latter are infeasible or where the validity of modeling strategies depends on quantities not easily identified. Also limiting is access to quantitative descriptions sensitive to other key features tied to oxygen homeostasis, as outlined below, such as the influence of sustained inflammation, expected disturbances in ROS-RNS metabolism, among other factors that are known to contribute to the impact of chronic diseases.

Network-Dependent Features of Cellular Phenotypes Common to Chronic Disease:

Closely tied to states of health and disease is the impact of network behaviors. Simply stated, true networks reflect behaviors that are in some way causally or otherwise linked. While the strengths of these linkages can vary, disturbances in one part of the network can produce disturbances in other areas. One form of such influences is feedback mechanisms that modulate biological functions on cellular, tissue, whole-organ or system-wide levels [34,35]. Another is structural elements that can comprise the peripheral nervous system, the vascular tree, and elements of brain anatomy.

Biological networks also exhibit distinct temporal behaviors that operate on different time scales. Rhythmic behaviors include rapid synaptic transmission events [36] and even more rapid electrical signaling mechanisms [37], as well as other behaviors that range from the cardiac and respiratory rhythms to circadian and hormonal (menstrual) cycles.

Being confined to the vascular space, network influences that affect the vascular tree can be expected to also influence behaviors of the Hb signal. For instance, well appreciated is that accompanying vasodilation is an increase in totalHb levels together with an influx of more highly oxygenated blood from arterial sources. Related to this is the coordinated coupling between local and more distant vascular responses that accompanies reactive hyperemia in skeletal muscle, and is mediated by intercellular communication between endothelial, vascular smooth muscle and myoendothelial coupling [38]. While recognized, the common practice of exploring elements of the Hb signal separately overlooks the principal phenomenology of network behaviors, which, as noted, can be expected to cause multiple elements of the network to co-vary. Also understood is that the factors responsible for promoting causative interactions within a network are often not simple linear sums of behaviors that might be discerned from its individual components.

Another feature closely tied to the time-varying behaviors of networks is their sensitivity to non-linear influences. This can have the effect of driving system behaviors from one preferred state to another. Discrete representations of this behavior can be adopted by collapsing details of the time domain [39]. By doing so, the effect is to represent what otherwise can be complex system behaviors as, instead, a system of discrete states that undergo transitions from one state to another in accordance with an assignable set of probabilities. Putting aside for the moment the details of how such states should be best defined and at what level of granularity, what is achieved by this representation is an explicit description of a network of interconnected states from which, as will be shown, a wide range of coefficients can be determined. Whereas elements of the vascular tree do form a structural network, the properties we consider do not directly follow from this. Instead, the network this invention considers is a functional one that arises from feedback mechanisms whose actions can be spatially and temporally distributed in tissue, but which share a common dependence on particular features of the Hb signal.

On a cellular level, attention to network behavior is drawn to actions driven by the various signaling cascades that allow for adaptation in the face of a diversity of signals representative of the complex ecology of these environments. Signaling by biochemical species, comprising proteins, lipids, metabolites, ions or gases, can initiate or have intermediary roles in cellular communication.

The need for intermediaries often arises because of diffusional barriers presented by the cell membrane. To overcome this and achieve actions with precision, signaling pathways often are initiated through binding of ligands (first messengers) to membrane-bound receptor proteins (e.g., G-protein coupled receptors (GPCR), signal transducers) that either directly lead to a response, such as the opening of ion channels as observed when gamma-amino butyric acid (GABA) binds to its receptor in neurons leading to influx of chloride ions, or initiate a set of intracellular protein-protein interactions such as orchestrated by G protein-coupled receptor kinases (GRKs; primary effectors) that ultimately can lead to the mentioned ecologically sensitive responses that are common to the actions of growth factors.

Common to many signal transduction pathways can be reliance on low molecular weight second messenger molecules, such as cAMP, that can reversibly bind to target proteins with high specificity, producing intended responses that can be greatly amplified. However, separate from this is another class of second messengers comprising reactive gaseous signaling molecules that effect actions which, while having reduced target precision, exert a degree of fine tuning and other actions that are unique. Key elements include nitric oxide (NO), hydrogen sulfide ($H_2S$) and carbon monoxide (CO) as well as their interactions with $O_2$ and resulting derivatives including superoxide ($O_2$.) hydroxyl radical (OH.), peroxinitrite ($ONOO^-$), nitrogen dioxide ($NO_2$), and dinitrogen trioxide ($N_2O_3$), among others.

This class of second messengers have chemical properties that allow for precise tuning of signal transduction pathways in ways that add a degree of flexibility of intended outcomes that have the effect of added efficiency. Driving this response is the mentioned duality of effects (hormesis), beneficial or harmful, of which the latter is responsible for actions of oxidative stress (OS). Underscoring these are specific biophysical properties and limited chemical reactivity. For instance, owing to their small size and solubility in lipid membranes, these species are able to participate in the mentioned reactions without having to rely on specific transporters. Also, while reactive, their activity is limited to metal centers, protein reactive thiol groups, and other radicals. Intrinsic chemical properties that allow this arise from unpaired electrons in a valence shell orbital that does not satisfy the main group octet rule.

This limited reactivity provides for targeted modulation of signaling cascades, mainly through oxidation of protein thiol groups involving hydroperoxides and redox-couples that serve to alter protein structures and subsequent signaling-dependent protein-protein interactions. Also available are adduct chemistries involving electrophiles that lead to S-nitrosylation (S—NO), tyrosylation (C—NO) glutathiolsylation, or other forms of protein post-translational modification. These reactions are reversible, allowing for adjustments in signaling activities depending on environmental demands. The net result of these reactions is the capacity to rapidly adjust the chemical tone of cells similar to how a rheostat operates [40].

There are many examples wherein behaviors dependent on ROS/RNS signaling can be expected to modify the tissue oxygen supply-demand balance. Examples include mechanisms responsible for scavenging NO, which can affect vascular tone, and the natural competition between NO and $O_2$ for binding to various cellular oxygenase enzymes. Other factors involve reactions tied to the immune response. For instance, closely associated with the NF-κB induction of a proinflammatory response, e.g., as a consequence of acute viral infection, is upregulation of NADPH oxidase activity along with proinflammatory cytokine production resulting in recruitment of phagocytic cells. Strongly linked to this is the phenomenon of "respiratory bursts" that can serve to generate ROS by non-mitochondrial mechanisms. The magnitude of this response can be notable. Seen are rates of oxygen consumption increased by 50-fold relative to background levels [41]. This behavior is relevant in instances where the immune response to a viral infection triggers the sometimes-disastrous cytokine storm. Closely tied to such effects is a reprogramming of cellular metabolism in myeloid-derived cells in response to inflammation-induced hypoxia, together with a marked upregulation of non-mitochondrial cellular oxygenase activity.

Also affecting oxygen supply-demand balance is the known coupling that occurs between the vasculature and its surrounding tissue. Having pleotropic actions, nitric oxide (NO), a form of reactive nitrogen species, plays a prominent modulatory role in this coupling. Being generated by endothelial nitric oxide synthase (eNOS), this reactive molecule exerts a paracrine effect on surrounding vascular smooth muscle cells by activating soluble guanylyl cyclase activity leading to vasodilation. Insults to vascular endothelial cells, such as occurs by drivers of cardiovascular disease (e.g., diabetes), can lead to disruption of this feedback effect causing hypertension among other effects.

As with the other forms of ROS-RNS species, enzymatic production of NO requires molecular oxygen. Having similar electronic structure and biophysical properties (e.g., both are highly diffusible gases), these two low molecular weight species exert feedback control on each other in several ways. For instance, the lifetime of NO, and hence its diffusible distance, is strongly attenuated by molecular oxygen [42]. One considered mechanism is that elevated $O_2$ levels can foster increased production of superoxide, which is a potent scavenger of NO, forming peroxynitrite. Added modulation of NO levels can be achieved by the scavenging actions exerted by oxyhemoglobin leading to formation of methemoglobin, which, when formed, is unable to transport $O_2$.

While these actions can be achieved though non-enzymatic mechanisms, enzyme-mediated processes serve to interconvert ROS-RNS species amongst themselves or to transform them to species that are notably less reactive. A principal mechanism for the latter, which also has a primary role in modulating signaling cascades, is the varied set of redox mechanisms that operate under the influence of Nrf2, the master antioxidant controller, and operate on hydroperoxides while involving actions from antioxidant mechanisms (e.g., glutathione peroxidase (GPx)—glutathione (GSH) couple, or perioxiredoxin (Prdx)—thioredoxin (Trx) couple). Also having impact is the cross-reactivity between NO and $O_2$, in particular as it relates to activities by various cellular oxygenases. Of note here is the ability of NO to inhibit mitochondrial cytochrome c-oxidase activity, thereby affecting ATP generation by oxidative phosphorylation and leading to effective backflow in electron transport with added production of superoxide.

Imbalance between the production of ROS-RNS and the antioxidant defense mechanisms is considered a principal mechanism for the generation of cellular OS. This is the process whereby ROS-RNS species can chemically oxidize susceptible cellular targets, principally involving nucleic acids, protein thiol-groups, and lipids, leading to cumulative cellular damage that serves to drive a multitude of disease processes as well as aging. While considered a key factor in the development of chronic disease, more acute disturbances are known to occur in acute viral syndromes and in early development following premature birth. The form of this disturbance affects a host of cellular processes, including cell survival, cell proliferation, and inflammation (among other factors), and, because of mitochondrial involvement, it can be expected to disturb homeostatic processes linked to oxygen consumption and cellular energy production. The latter is known to modulate mechanisms linked to adjustments in vascular supply.

In summary, the oxygen supply-demand balance seen in the steady state represents orchestrated behaviors that occur on system-wide and local levels, through adjustment in vascular tone as well as through cellular-based mechanisms that modulate activity of a host of cellular oxygenase activities. The latter can be notably impacted by actions of the innate immune response to acute or chronic disease that have the effect of strongly modulating ROS-RNS metabolism along with diversion of oxygen utilization from mitochondrial to non-mitochondrial sources.

As outlined, whereas the current art does allow for adoption of specific technologies, analysis methods and experimental techniques that can appreciate particular elements of the interplay between oxygen homeostasis and chronic disease, none of those considered meet the criterion of enabling a generalizable strategy that supports key practical elements of health evaluation; i.e., noninvasive longitudinal monitoring, evaluation of essentially any tissue type, measures performed in favorable environmental settings, access to network measures, extension to multiple forms of time-series measures.

Opportunity to Advance Goal of Achieving Personalized Medicine:

New concepts and methodological strategies are being developed to achieve the aim of adopting a proactive rather than reactive approach to medicine. One form is the concept of "P4 medicine" [43]. Comprising four elements—predictive, preventive, personalized and participatory medicine—this approach advances wellness as a key factor impacting dynamic systems-level behaviors whose aberrations typify chronic disease. Key methodological resources strongly supportive of this aim are the expanding capabilities of panomic technologies (genomic, transcriptomic, epigenomic, proteomic, metabolomic and microbiomic) combined with other available measures that foster the capacity for deep phenotyping [44].

Personalized medicine offers the attractive prospect of tailored interventions guided by recognizing patterns in the panomic profile that are either characteristic of a specific disease or indicative of favorable or unfavorable early treatment responses. While conceptually appealing, this approach assumes that the information contained in such profiles, which themselves are incomplete, discrete and often sensitive to sampling biases, offers the level of guidance that is sought.

While other available information is considered when attempting to generate tailored approaches (e.g., common physiological measures such as blood oxygen saturation, cardiac dynamics, blood pressure, family history, etc.,) the P4 approach as currently practiced can be viewed as a "book-ended" strategy, wherein at one end a wealth of molecular markers are identified, while at the other extreme systemic and other holistic understandings are considered.

Currently not considered are measures applied to intact tissues, even though during the early stage of disease evidence of its presence is most likely locally confined. Among the methods available for investigating intact tissues, attention is drawn to non-invasive measures. Available here are structural imaging methods, measures of impedance, and dynamic measures sensitive to bioelectric and hemodynamic phenomena.

Because early disease does not produce notable structural malformations, consideration of noninvasive measures necessarily is directed to the functional techniques. While experience shows that the sensitivity of such methods also can be limited in the early stages of disease, taking a broader view, even if more sensitive techniques could be adopted, as currently practiced the granularity of the information generated is decidedly limited. For instance, while measures such as heart rate, heart rate variability, and blood oxygen saturation are informative, this degree of granularity pales in comparison to the often thousands of measures or more available from the panomic techniques.

One strategy that has proven effective in extending the information value of functional measures is to apply an array of sensors from which a wide range of topological features can be defined. Often considered here are the methods sensitive to either bioelectric or hemodynamic phenomena. The former includes the techniques of electroencephalography (EEG) and magnetoencephalography (MEG), while examples of the latter are functional magnetic resonance imaging (fMRI) and functional near infrared spectroscopy (fNIRS). While such measures have served to extend the utility of these methods, thus far they have mainly been applied to investigations of the brain. With regard to the goals of P4 medicine, the ability to gain added insight from measures of intact tissue would be notably challenged without extending measures to include other tissue types as well. While this is technically feasible, the functional organization of peripheral tissues is decidedly limited compared to the richly directed and anatomically specialized behaviors of the brain. Thus, it would seem, on first glance, that the goals of advancing the aims of P4 medicine by inclusion of non-invasive, tissue directed measures is out-of-reach for most tissue types.

Partial Solution to the Problem of Extending Network Measures to Other Tissue Classes:

Our group has recently described a general methodology that enables the description of network behaviors from measures of the Hb signal in the resting state [45]. The thrust of this technique, which is applicable to any tissue type, has been to recognize that by transforming a continuous time-series measure to a set of discretized states, a set of adjacency matrices becomes accessible that describe the nodal and edge properties of the defined network, and that canonical measures of topological features can be derived from these. However, unlike the single-state representation common to investigations of the brain, whose network metrics are typically limited to coefficients reflecting edge behaviors, our technique produces two principal classes of information: transition-state behaviors and Hb-component behaviors, reflecting properties of both nodal and edge information. Other key features identified in this first report [45] was evidence of what appears as substantial independence among the different feature spaces, and evidence that these can serve as useful biomarkers that are sensitive to a representative chronic disease (breast cancer). Returning to the goal of advancing P4 medicine by inclusion of non-invasive, tissue-directed measures from any tissue class, this technique, with its demonstrated ability to yield a set of mainly independent, rich feature biomarkers that are disease sensitive, would seem to hold potential to overcome at least some of the noted concerns.

As an aid to advancing a more basic understanding as to how such behaviors can be discovered, we recognize that because the behavior governing steady-state processes is invariably an expression of a host of factors (i.e., the prevailing epigenetic landscape), the pattern of disease-sensitive behaviors observed in the individual adjacency matrices is undoubtedly a low-order representation of higher-dimensional influences. A simplified approach to gaining added understanding of factors affecting steady-state system dynamics is to explore co-dependent behaviors, in the expectation that at least some pairings may reveal composites that are more easily interpreted.

Also recognized, though not explicitly explored here, is that while evidence of highly structured co-dependent behaviors can be identified in specific instances, they are observed for only one of many potential definitions of state properties. Leveraging understandings gained from the principles of tomography, such determinations can be similarly recognized as constituting only one, or at most a limited view, of system behaviors. Because experience shows that multi-view tomographic measures support discovery of otherwise hidden (convolved) features, it is our belief that additional understandings of the drivers of steady-state behaviors can be similarly gained through adjustments to the applied state definitions.

Advancing this understanding, which was not considered in the Barbour 2018 patent [45], and is part of the originality of the present one, is the recognition that simplified biological interpretations can be ascribed to various adjacency matrix classes. For instance, the elements of a State-probability matrix can plausibly be interpreted as being proportional to "concentrations" of some driver of overall network behavior, while transition-flux values for the Hb components can be taken as representative of some composite of enzyme behavior. Extending this reasoning leads to a plausible expectation that co-dependencies among the different coefficient spaces may reveal trends that reflect the influence of the putative hidden (i.e., not directly observed) biological drivers. To the extent that the analogies to "substrate concentration" and "enzyme activity" are valid, one may expect to find indications of saturable responses (i.e., hyperbolic functional forms) in the co-dependences between some pairs of network features, and evidence for this is described herein.

Similarly, because multiple network features are disease sensitive, this suggests a connection to known disease-associated changes in the gene expression-epigenetic profile, and leads to the expectation that the associated enzyme-dependent steady-state molecular concentrations will be similarly affected. Basic thermodynamics of chemical reactions tells us that such steady-state adjustments reflect changes in chemical potentials, and this leads to a recognition that measures arising from application of the laws of thermodynamics should be possible. Thermodynamics has been applied to networks for other systems [46, 47], with a key feature being the understanding that network behaviors must obey the 1st law of thermodynamics, leading to invocation of Tellegen's theorem (i.e., an important generalization of Kirchhoff's voltage and current laws [46, 47]), which holds that the sum of products of voltage and current, over an entire network, must be zero.

A part of the originality of the present patent is the demonstration of pairings of network features that satisfy Tellegen's theorem, and subsequent consideration of thermodynamic features. Review of prior art reveals many examples of thermodynamic-property computations for entities linked in a network. Most frequently explored are various measures of entropy, while extension to other thermodynamic quantities (e.g., Gibbs free energy, enthalpy, temperature), is notably less common, largely because measures of biological behaviors frequently do not contain the requisite information regarding properties of network nodes (as opposed to edges). Consequently, features that require only knowledge of network-edge properties are typically considered (e.g., entropy [48]) for analysis of time-dependent functional brain measures via EEG-MEG and, fMRI, and also in many prior applications of fNIRS. In contrast, because the applied methodology herein does allow for node descriptions, this can provide access to the expanded set of thermodynamic measures of which examples of computations of Gibbs free energy are provided herein.

We further recognize that the methods outlined in the following sections should be applicable to any form of time-dependent physiological behavior, having either an exogeneous (e.g., fNIRS, photoacoustic, dynamic acoustic, fMRI), or endogenous source (e.g., dynamic thermography, ECG, EEG, ECoG, MEG measures). For instance, it is straightforward to apply state definitions to the known time-varying frequency structure of these measures. Using the methods described herein, directly accessible are measures of the probability of transition between any pair of frequency components, as well as the associated pre- and post-transition state-dependent dwell times. Because the amplitude of any individual frequency band is easily determined, also available are measures equivalent to those considered here, including the pre- and post-transition time-averaged amplitude of a given component, as well as equivalent measures of component flux and mass. As outlined subsequently, this provides the opportunity to define system measurement configurations and analysis strategies that are appropriate for a wide range of applications that leverage the goals of precision medicine.

An important practical motivation for the invention described herein is the need for clinical and research tools suitable for cases where perturbation methods are not feasible. An alternative is measures of the resting state, or at least under conditions that closely approximate a resting state. A clear advantage of this approach is that it is often the easiest to implement, is well suited for vulnerable populations, and is the most adaptable to different clinical and experimental environments (as evidenced by the many forms of continuous monitoring that are employed in hospital settings, such as ECG, pulse oximetry, and respiratory measures). A further practical advantage of the resting-state approach is that it provides the best approximation to the steady-state or quasi-steady-state conditions that are assumed to hold, in the theory that underlies the thermodynamic concepts (e.g., Tellegen's theorem) and parameters (e.g., entropy, Gibbs free energy) described earlier in this section.

We note as well, that conditions suitable for the suggested measures can likely be expanded beyond a strict resting state. For example, while preferred measures involve subjects in a seated or supine position and substantially at rest, it would seem feasible to impose low-amplitude dynamic postural-change maneuvers (e.g., table tilts) as stimuli to autonomic responses. Also feasible should be higher-amplitude static repositioning maneuvers, protocols involving slow-speed walking on a treadmill, inflation of blood-pressure cuffs about the lower extremities (with target measures on the head or upper torso), inspiration of different respiratory-gas mixtures administration of pharmaceuticals while at rest, or participation in neurocognitive studies while quietly seated.

Described as a first representation are methods and alternatives that cast co-varying features of the time-dependent Hb signal as a functional network from measures that substantially comprise a resting state. Explored more fully in the preferred embodiment are clinical findings from CW NIRS array measures that examine a representative disease process (breast cancer) and document access to dense feature spaces that have many degrees of freedom with promising diagnostic potential, even when limited to univariate statistical indices. Also identified is that, whereas such understandings likely reflect low-order representations of high-dimensional influences arising from the network of cellular and system-level processes affected by chronic disease, explicitly outlined are strategies that recognize highly structured forms of co-varying network behaviors that are strongly suggestive of enzyme-like behaviors. Thus, although measures are acquired on a macroscopic level, information derived suggests sensitivity to a composite of microscopic influences that are likely reflective of the prevailing epigenetic landscape. Further identified by the described methods are quantitative descriptions consistent with basic network thermodynamic understandings that have been recognized in other fields, but here are applied as a first instance to time-series biological measures. Notably, these approaches, in addition to expanding access to novel aspects of derived feature spaces, give evidence of independent validation (see section 8.h. under Preferred Embodiment), offering high confidence in the fidelity of the described methods.

In one aspect, the invention is a non-invasive method of detecting anomalous tissue in a patient reflective of the influences of a host of chronic diseases known to affect oxygen homeostasis. At least two Hb signal components of Hb levels are non-invasively measured in at least one segment of tissue of the patient over time. First time-varying changes of at least a first of the Hb signal components are measured with respect to at least second time-varying changes of a second of the Hb signal components. A co-varying coordinate system of the plurality of time-varying changes is generated. Any anomalous tissue in the measured segment of tissue is detected from a signature of the measured segment of tissue in the co-varying coordinate system which differs from a signature of non-anomalous tissue in the co-varying coordinate system.

Preferably, transitions of the Hb signal components from at least one Hb state to another Hb state are detected. Transition coefficients are determined. Values of the transitions are mapped. Patterns are discerned in the values indicative of the presence or absence of anomalous tissue. Preferably, five Hb signal components are discerned: oxyHb, deoxyHb, totalHb (totalHb=deoxyHb +oxyHb), Hb oxygen saturation (HbO$_2$Sat=(oxyHb/totalHb)*100), and tissue-hemoglobin oxygen exchange (HbO$_2$Exc=deoxyHb–oxyHb).

Optionally, the tissue is measured optically. Optionally, the tissue is illuminated with light, and at least one of diffusely transmitted or back-reflected light is measured. In another aspect of this invention, the invention is a non-invasive method of detecting breast cancer in a patient. At least two Hb signal components of Hb levels are non-invasively measured in at least one breast of the patient over time. First time varying changes of at least a first of the Hb signal components are measured with respect to at least second time-varying changes of a second of the Hb signal components. A co-varying coordinate system of the plurality of time varying changes is generated. Any cancerous tissue in the measured breast is detected from a signature of the measured breast in the co-varying coordinate system which differs from a signature of non-cancerous tissue in the co-varying coordinate system.

Preferably, transitions of the Hb signal components from at least one Hb state to another Hb state are detected. Transition coefficients are determined. Values of the transition coefficients are mapped. Patterns are discerned in the values indicative of the presence or absence of anomalous tissue. Preferably, five Hb signal components are discerned: oxyHb, deoxyHb, totalHb (totalHb=deoxyHb +oxyHb), Hb oxygen saturation (HbO$_2$Sat=(oxyHb/totalHb)*100), and tissue-hemoglobin oxygen exchange (HbO$_2$Exc=deoxyHb–oxyHb).

Optionally, a breast is measured optically. Optionally, the segment of breast tissue is illuminated with light, and at least one of diffusely transmitted or back-reflected light from the segment of tissue is/are measured. The segment of breast tissue to be detected includes at least one of cancerous tissue or anomalous tissue reflective of the presence of chronic disease.

In another aspect of the invention, anomalous tissue is detected by other forms of time-dependent physiological measures acquired from sources having exogeneous or endogenous origins (e.g., bioelectric signal). Applied is a network description derived from assignment of State definitions to recognizable features contained in such time-varying signals as defined herein. In one form, such assignments can be made by isolating specified frequency bands of interest. This yields a time-series of assigned states comprising features having identifiable amplitudes. Representation of these in the form of the various adjacency matrices follows from computation of corresponding time-averaged coefficients. The potential for identifying features hidden by low-order representations of these can be achieved using the methods outlined herein. Further, regardless of the applied sensing approach, the methods described herein are applicable to any tissue type and can be applied using measures acquired from at least one sensor.

BRIEF DESCRIPTION OF THE DRAWINGS

FIG. 3(a), transition probabilities (computed using Eq. (5), units are percent); FIG. 3(b), pre-transition dwell times (computed using Eq. (6), units are time steps); FIG. 3(c), ΔHbO$_2$Sat pre-transition mean values (computed using Eq. (9), units are percent per transition); and FIG. 3(d), ΔtotalHb pre-transition mean values (computed using Eq. (9), units are moles per liter (M) per transition), for the tumor-bearing breast of subjects with unilateral breast cancer (N=18), all in accordance with the invention.

FIG. 5(a) tumor-bearing breast of subjects with unilateral breast cancer, FIG. 5(b) unaffected breast of subjects with unilateral breast cancer (N=18), and FIG. 5(c) left breast of subjects who do not have breast cancer (N=45), all in accordance with the invention. Regions labeled with '+' (where the ratio is <1) have the sign-reversing transition probability in the numerator; regions labeled with '−' (where the ratio is >1) have the sign-preserving transition probability in the numerator.

FIG. 6(a) is a plot of ΔHbO$_2$Sat pre-transition mean values (units, %) vs. ΔtotalHb post-transition mean values (units, M), and FIG. 6(b), ΔtotalHb flux values vs. ΔtotalHb pre-transition mean values (units, M), for the tumor-bearing breast of subjects with unilateral breast cancer, all in accordance with the invention. See legend of FIG. 4 for symbol definitions. Arrows in FIG. 6(b) indicate clusters of hyperbolas having long (blue color) and short (red color) spans whose computed vertices and foci are plotted in FIGS. 7(d)-(f). See legend of FIG. 4 for symbol definitions. The functional form for each hyperbolic curve is $y = ax + b \pm \sqrt{cx^2 + dx + e}$ (c>0), where 'x' can denote the quantity plotted on either coordinate axis, and 'y' is the quantity plotted on the other axis. The $y = ax + b + \sqrt{cx^2 + dx + e}$ form generates a curve that is concave up (e.g., red curve in FIG. 6(a)), while $y = ax + b - \sqrt{cx^2 + dx + e}$ produces a concave-down curve (e.g., cyan curve in FIG. 6(a)).

FIGS. 7(a)-7(f) are plots of the computed vertices (circles) and foci (diamonds) of the hyperbolas fitted to the sets of curves plotted in FIG. 6, all in accordance with the invention. FIG. 7(a) and FIG. 7(d) are plots of vertex and focus coordinates for hyperbolas fitted to groupings of points in FIG. 6(a), and FIG. 6(b), respectively, for the tumor-bearing breast of subjects with unilateral breast cancer. FIGS. 7(b) and 7(e) are plots of differences between vertex and focus coordinates for hyperbolas fitted to groupings of points in FIGS. 6(a) and 6(b) and corresponding values for the unaffected breast of subjects with unilateral breast cancer, respectively. FIG. 7(c) and FIG. 7(f) are similar difference plots as in FIGS. 7(b) and 7(e), except that involve differences between the left (L) and right (R) breasts for subjects without breast cancer. See legend of FIG. 4 for symbol definitions. Note, points plotted in quadrants I and III, and II and IV of FIGS. 7(d)-7(f), correspond to the arrows identified for the long and short spans, respectively, for hyperbolas identified by arrows in FIG. 6(b). Also shown are computed regression lines in each quadrant, demonstrating differences in extrapolated intercepts between quadrants II and IV compared to I and III.

FIGS. 8(a)-8(h) are computed adjacency matrices of Gibbs free energies (ΔG) for individual transition types, all in accordance with the invention. FIGS. 8(a)-8(d): results for ΔHbO$_2$Sat ΔG (units, %); FIGS. 8(e)-8(h): results for ΔtotalHb ΔG (units, M). FIG. 8(a),(e): group-mean ΔG values for the tumor-bearing (T) breast of women with breast cancer; FIG. 8(b),(f): difference between group-mean ΔG values for the T breast and for the contralateral unaffected breast (U); FIG. 8(c),(g): p-values for unequal-variance, unpaired t-tests on differences between ΔG(T) and ΔG(U); FIGS. 8(d),(h): same computation as in FIG. 8(c),(g) except applied to corresponding difference between L and R breast groups, respectively, of control subjects.

FIG. 10(a) identifies the transition type for each plotted point by its shape and color (see legend of FIG. 4 for symbol definitions), and FIG. 10(b) identifies the transition Class for each plotted point by its color. Computed best fit hyperbolas employed the same functional form listed in legend of FIG. 6.

FIG. 12(a) is a plot of linear combinations of ΔG(ΔHbO$_2$Sat) and ΔG(ΔoxyHb) vs. pre-transition State volume fraction, for the T (red data points), U (blue), L (magenta) and R (cyan) breast groups, in accordance with the invention. Pre-transition States are encoded by the data-point shapes, as described in the legend to FIG. 4.

FIG. 13(a) reveals computed findings when colored noise is substituted for the "ΔHbO$_2$Sat" vs "ΔtotalHb" values plotted in FIG. 6(b). Deviations from white noise included imposing the same correlation value between measured values of ΔoxyHb and ΔdeoxyHb, (−0.4), temporal mean HbO$_2$Sat value (85%), and ratios of oxyHb$_{AC}$/oxyHb$_{DC}$ and oxyHb$_{AC}$/deoxyHb$_{AC}$ as are observed in the actual breast data.

DETAILED DESCRIPTION OF THE INVENTION AND DRAWINGS

Figures 1A, 1B:
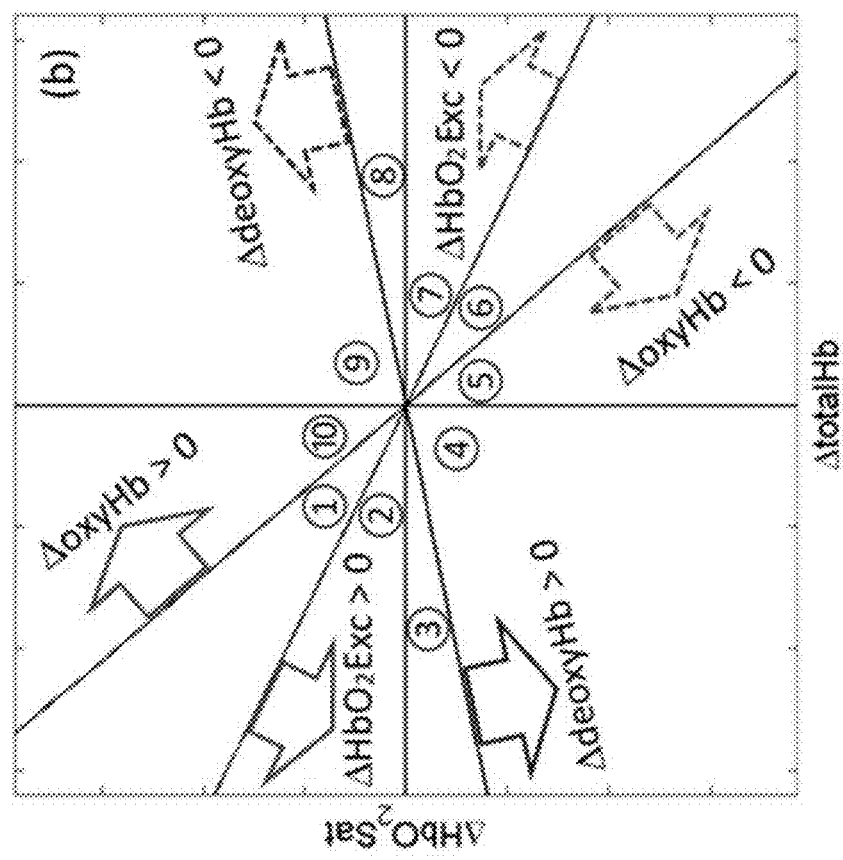
FIGS. 1(a) and 1(b) are graphical descriptions depicting regions in FIG. 1(a) (ΔdeoxyHb, ΔoxyHb) space and in FIG. 1(b) (ΔtotalHb, ΔHbO$_2$Sat) space that correspond to positive or negative values, with respect to the temporal mean, for each commonly considered component of the Hb signal, in accordance with the invention. Each Hb State is a region corresponding to one of the ten physiologically allowed permutations of algebraic signs of the five considered components of the Hb signal (see Table 1 in Ref 45 for complete description of the component algebraic sign permutations corresponding to each State).

Description will now be given with reference to the attached FIGS. 1-13. It should be understood that these figures are exemplary in nature and in no way serve to limit the scope of the invention, which is defined by the claims appearing below.

Method of Procedure for Acquiring Time-Series Measures of Hb Signal.

Step 1. Target tissue(s), which can include, but are not limited to the chest, limbs, wrist, finger, head, neck, torso, shoulders, or feet, is illuminated using either contact of non-contact methods comprising at least one source, and diffusely transmitted or back-reflected light is measured using either contact or non-contact optical sensing elements comprising at least one receiver. When using arrays of discrete sources, source encoding can be accomplished using methods that vary from full time-multiplexing to full frequency encoding methods. Illumination from a given source is achieved using at least two wavelengths of light, which can include discrete or broad-area illumination techniques. Optical (photoacoustic) detection of reemitted light is achieved using receivers operated to recognize the intensity, amplitude and phase, temporal or corresponding structured-spatial properties (e.g., as is employed in spatial frequency domain imaging) of the applied illumination. When appropriate, system gain values are adjusted to the individual to ensure acquired values are within the system's operating range.

For contact-based measures, applied sensors (emitters and receivers) can be stabilized with added mechanical supports, which can include use of flexible links or membranes to form an interconnected lattice that can be made to conform to nonuniform tissue boundaries. Alternatively, these can be introduced within a fabric cap or pad to conform to non-uniform tissue geometries. Also available are sensing arrays that can be housed within a low-profile pad whose driving electronics can be accomplished through a nearby wireless amplifier or by use of an electronic ribbon cable that serves to transmit power and timing signals. Also, light transmission and collection can be accomplished by use of optical fibers whose contact with the body is stabilized by suitable support structures. Also, the ease with which optical measures can be introduced into an endoscopic format indicates that tissues accessible by this class of techniques could also be examined.

Step 2. Data collected in (1) is performed on subjects who are either in the seated, supine or prone position, or other body orientation(s) for which the tissue(s) under investigation are substantially stabilized. Should the data-collection protocol impose perturbations, these are employed in ways that do not overtly render target tissue measures unstable.

Step 3. Data collection involves capturing a time-series of measures.

Step 4. Collected wavelength data is transformed to Hb values, by applying a modified Beer-Lambert transform to yield values of ΔoxyHb and ΔdeoxyHb, which are subsequently normalized to their respective temporal mean values. If required, these measures can be further processed to yield computed values of ΔtotalHb, ΔHbO$_2$Sat and ΔHbO$_2$Exc. Also, if desired, acquired wavelength-dependent time-series measures can be additionally transformed to form a wavelength-dependent tomographic image by applying suitable inverse transforms, followed by subsequent conversions that equate changes in Hb concentration to the product of the wavelength-dependent extinction coefficient and computed change in the position-dependent absorption coefficient.

Method of Procedure for Transforming Time-Varying Measures of Hb Signal to Yield Coefficients of Network-Dependent Features of the Hemoglobin Signal.

1. Time series of $\Delta$deoxyHb, $\Delta$HbO$_2$Exc, $\Delta$HbO$_2$Sat, $\Delta$oxyHb, and $\Delta$totalHb, computed via the steps outlined in the preceding section, are loaded into computer memory for post-processing. Prior to loading, frequency filtering of data, or not, can be applied as desired.

2. The Hb-State corresponding to each image voxel (or source-detector channel) and time frame is computed as follows:
   a. A three-dimensional temporary data-storage array is created, having the same number of rows (i.e., time frames) and columns (i.e., voxels or channels) as the data arrays loaded in Step 1, and having five layers that correspond to the five components of the Hb signal. The initial value of every array is 0.
   b. Every element of the array created in Step 2.a., is assigned a value of either −1 or +1, depending on whether the value for the Hb-signal component corresponding to the layer-index value, is less than or greater than that same component's mean value at the voxel or channel location corresponding to the column index value, during the measurement time frame corresponding to the row index value. Ten distinct permutations of '±1' values are logically possible and physiologically plausible. A lookup table, assigning each of these permutations to an integer in the 1-10 range, is generated.
   c. A two-dimensional permanent data-storage array is created, having the same number of rows and columns as the data arrays loaded in Step 1. The initial value of every array element is 0. Every element of this array is then assigned an integer value in the range of 1 to 10, by referencing the lookup table described in Step 2.b.

3. Transition-count and transition-probability information is computed as follows:
   a. A two-dimensional data-storage array is created, having ten rows and ten columns. The initial value of every array element is 0.
   b. The Hb-State array in Step 2 is scanned, starting from the first row and first column; proceeding through each succeeding row of the first column until the last row is reached; then to the first row and second column; then through each succeeding row of the second column; then to the remaining columns in turn until the last row, last column is reached.
   c. At the start of each transition-count operation, the Hb-State value at the current row-and-column position (by definition, row i and column j) is compared to the Hb-State value in row i+1, column j. The value of an element in the array created in Step 3.a, is increased by 1. The column coordinate of the selected array element is equal to the row i, column j Hb-State value, and the row coordinate is equal to the row i+1, column j Hb-State value.
   d. After the entire array of the Hb-State values is scanned, transition probabilities are computed by applying Eq. (5) of the Preferred Embodiment to the transition-count array.

4. Pre-transition dwell-time and post-transition dwell-time information is computed as follows:
   a. At the same time that the array described in Step 3.a, is created, an additional two arrays having the same dimensions and initial values of 0 in every element, are also created.
   b. After the entire array of Hb-State values is scanned, as described in Step 3.b, pre-transition dwell times and post-transition dwell times are computed by applying Eq. (6) of the Preferred Embodiment to the arrays created in Step 3.a and 4.a.

5. Pre-transition mean-value and post-transition mean-value information is computed as follows:
   a. At the same time that the array described in Step 3.a, is created, an additional ten arrays having the same dimensions and initial values of 0 in every element, are also created.
   b. Every time the value of an element of the transition-count is incremented, as described in Step 3.c, the corresponding elements of the arrays created in Step 5.a also have their values modified. The changes in the current array-element values are computed via Eq. (8) of the Preferred Embodiment.
   c. After the entire array of Hb-State values is scanned, pre-transition mean values and post-transition mean values are computed by applying Eq. (9) of the Preferred Embodiment to the arrays created in Steps 3.a and 5.a.

6. Transition-flux and transition-mass information is computed as follows:
   a. At the same time that the array described in Step 3.a, is created, an additional five arrays having the same dimensions and initial values of 0 in every element, are also created.
   b. Every time the value of an element of the transition-count is incremented, as described in Step 3.c, the corresponding elements of the arrays created in Step 6.a also have their values modified. The changes in the current array-element values are computed via Eq. (8) of the Preferred Embodiment.
   c. After the entire array of Hb-State values is scanned, transition fluxes are computed by applying Eq. (10) of the Preferred Embodiment to the arrays created in Steps 3.a and 6.a.
   d. After the entire array of Hb-State values is scanned, transition masses are computed by applying Eq. (11) of the Preferred Embodiment to the arrays created in Step 6.a.

7. After transition probabilities (Step 3), pre-transition and post-transition dwell times (Step 4), and pre-transition and post-transition mean values (Step 5) are computed, thermodynamic-parameter information is computed by applying Eq. (15) (for Boltzmann energy distributions) of the Preferred Embodiment to the arrays created in Step 3.d, Eqs. (16) and (18) (for Gibbs free energies) of the Preferred Embodiment to the arrays created in Steps 4.b and 5.c, and Eq. (19) (for network entropies) of the Preferred Embodiment to the arrays created in Steps 3.d, 4.b, 5.c and 6.c.

Effects of the Invention

Having the goal of appreciating abnormal or normal tissue states under a wide range of environmental situations and subject status conditions for which prior-art uses of perturbation methods are likely to prove impractical or even harmful, and in recognition that the physiological mechanisms that sustain oxygen homeostasis in tissue can impart features that are not observable from application of feature extraction methods to the individual components of the Hb signal, the inventive methods described herein, favorably applied under a substantially resting state condition, serve to greatly expand the environments and subject status conditions wherein noninvasive Hb time-series measures of tissues can be acquired and from which a previously unrecognized dense feature space of coefficients and associated co-dependencies can be accessed.

As is documented by the varied measures described in the Preferred and Alternative Embodiments, and applied to a representative tissue class (breast) and representative disease type (cancer), derived coefficients have the character of substantial independence across a wide range of coefficient types whose amplitudes appear strongly sensitive to the presence of disease. It is further recognized that the described methods, together with the opportunity to extend such methods to the other noted forms of time-varying physiological measures, support access to deeply hidden behaviors, some of which have been shown to exhibit enzyme-like behaviors. Also, having recognized that disturbances in oxygen homeostasis, as influenced by OS-induced inflammatory responses affects a wide range of disease types as well as tissue responses to differing classes of stimulation imposed by external stimuli, drugs, and interactions with tissue implants, the methods described here are deemed to significantly facilitate assessment of these behaviors and in doing so can support the following capabilities:

1. Improved detection of the level of OS-induced inflammation produced by acute viral syndromes, especially those targeting lung function. Such measures hold particular significance under situations of a pandemic wherein notable concerns of undesired disease spread can occur from affected individuals visiting key transportation hubs or other key infrastructure facilities. Being non-invasive and easily applied, the described invention is ideally suited for monitoring of subjects in low-resource-intensive environments and allows for longitudinal monitoring. Disease-sensitive biomarkers derived from the described methods should allow for more informed decisions regarding triage management, especially in situations wherein available care resources are overwhelmed.

2. Improved detection and monitoring of OS-induced inflammation produced by various forms of chronic disease (e.g., Type-II diabetes mellitus, atherosclerosis, obesity, cancer, autoimmune diseases, neurodegenerative diseases). Often these conditions pose limitations on how diagnostic workups can be performed, particularly in low-resource or remote locations. Offering noninvasive measures that can be applied to any tissue site, biomarkers derived from the network adjacency matrices and associated transforms can serve as a longitudinal monitoring tool that can alert caregivers to whether applied treatments are having the intended effects.

3. Improved monitoring of wound healing. Upregulation of signaling cascades, especially those related to inflammation are the vehicle by which tissue repair and wound healing occurs. Existing methods, which can employ the techniques of hyperspectral imaging, OCT, laser Doppler imaging, laser speckle imaging, spatial frequency domain imaging and digital camera imaging, all share the goal of producing information of individual features (e.g., individual Hb components, wound size and area, burn depth, burn scar perfusion, and collagen denaturation) and do not consider co-varying properties common to functional networks that modulate the bulk of physiological phenomena in living beings [49,50].

The presence of an expected inflammatory response, reduced perfusion in affected regions and neovascularization associated with wound recovery strongly indicate that the normal oxygen homeostasis supply-demands present in healthy unaffected tissues should be strongly affected. As a consequence, we anticipate that several of the identified coefficient classes listed in the Preferred Embodiment will likely be affected. As each of these constitutes a dense array of mainly independent behaviors, the discriminatory power likely accessible from these measures as a basis for clinical guidance and characterization is significantly improved compared to existing assessment tools. Also recognized is that, because several of the listed methods can be adapted to provide time-series measures of the Hb signal, it is expected that more than one class of system capabilities (e.g., photoacoustic, holographic) are likely to benefit from the inventive matter disclosed herein.

4. Improved monitoring of the progression, or the response to therapeutic interventions, of chronic pathologies that have vascular manifestations. This class would include peripheral artery disease (PAD), and diabetic vasculopathy. The methods of the invention allow for greater ability to acquire relevant data from any tissue site with minimal disruption to subjects' activities of daily living.

5. Improved monitoring of the progression, or of the response to therapeutic interventions, of pathologies that produce skin ulcers or other dermatological lesions. This class includes the mentioned cases of PAD and diabetes, and also some cases of autoimmune diseases such as lupus and psoriasis. A related class of applications is the detection of incipient bedsores in individuals who are comatose or are conscious but bedridden.

6. The methods of the invention are potentially applicable for clinical or research environments in which the target population consists of or includes individuals who are unconscious or paralyzed. The latter category would include cases of temporary (e.g., because the subject is immobilized by a cast) as well as permanent paralysis (e.g., owing to spinal-cord injury). Also recognized is the value in distinguishing and longitudinal monitoring of variable states of consciousness resulting from injury, disease, or effects of administered drugs.

7. Recording of hemodynamic data from the brain, peripheral structures, or both, during sleep studies. These applications have the potential to yield insight into the physiological stresses induced by conditions such as sleep apnea, as well as the effectiveness of interventions such as positive airway pressure.

8. Earlier and more reliable detection of inflammatory states, in tissues lying within the limits of optical penetration, whether these states are of acute (e.g., bacterial infection, medication side effects) or chronic origin (e.g., incipient arthritis, autoimmune disease, arteriosclerosis).

9. Improved ability to include infants and children and other vulnerable subject classes within the population of subjects that can be evaluated using NIRS-based technologies. These are individuals for whom some perturbation-based strategies may be physically impossible (e.g., Valsalva maneuver by neonatal subjects), while others may be deemed to pose unacceptable risk or would be likely to meet with poor compliance (e.g., 12-hr fasting for pediatric subjects).

10. Improved ability to monitor the mental alertness, or the peripheral-tissue oxygenation status, of people engaged in activities that involve low levels of physical activity, although frequently over an extended period, coupled with high levels of mental effort. Examples of applications in this area may include long-haul truck drivers, operators of commercial or military aircraft or ships or members of surgical teams, for early indications of fatigue.

11. Better performance and extended range of capabilities for brain-computer interface (BCI) applications. These are likely consequences of the invention making a set of previously unappreciated hemodynamic features available for analysis. Some of the many available feature classes may prove to correlate better, or more consistently or reliably with subject intent to effect the perturbation-based responses that are the current focus of most BCI efforts. Alternatively, in recognition that the goal of BCI is to infer information on a relatively short time scale, and in recognition that coordinated behaviors of the brain are not static, the considered measures may serve to identify which of several likely functional states are operational. It follows that applied training methods can be fine-tuned to recognize when these are present, thereby improving the interpretation of individual subject responses.

12. Improved routine heath monitoring advanced by use of wearable devices that support longitudinal monitoring of resting-state set-point measures. For NIRS-based measures, these devices can be applied to the cranium or to any of a number of peripheral tissues (e.g., breast, skeletal muscle, adipose). Information gained from such measures is expected to support the principal goals of precision medicine, either as a stand-alone tool or in combination with panomic methods.

13. Improved ability for deceit detection. Methods described herein provide the ability to notably expand the accessible feature space compared to existing NIRS-based neurosensing methods. This follows because, unlike the requirement for identifying network features from an array of sensors, the current method can yield such information for each sensor or combinations of sensors. Also, because the current method provides descriptions of both nodal and edge behaviors, the current method supports access to other feature class such as particular thermodynamic quantities (e.g., Gibbs free energy). These can be combined with canonical measures of network topology to provide for a set of measures that are easily supported by machine learning methods.

14. Expanded information access from alternative time-series measures that can serve to enhance the utility of these methods as currently applied. It is recognized that the inventive methods described herein can be applied to other forms of time-varying physiological measures such as ECG, EEG, MEG, ECoG, fMRI, dynamic forms of thermography, OCT, photoacoustic, holography, and other sensing methods easily extended to time-domain measures, either separately or in combination. Also expanding their utility is the understanding that for each type, the applied state definitions can be adjusted as noted herein. Similarly, expanded access to higher-order behaviors from exploring co-dependencies among the network adjacency matrices, as well as from access to an expanded set of thermodynamic and network topological measures, can also serve to enhance all of the considered uses described herein 15. The methods described herein can be extended to improve capabilities that explore other time-dependent processes having non-biological/medical uses. One example is the exploration of econometric time-series data. Here we expect that, similar to behaviors seen in the exemplary data considered herein, patterns identified in correspondingly derived econometric feature spaces (i.e., adjacency matrices) derived from time-series measures will similarly prove sensitive to the influence of underlying drivers. Efforts to quantify the impact of drivers has long been appreciated by this community. For instance, often considered by this field is the method of Granger Causality, which seeks to identify the forecasting influence of one time-dependent process (e.g., trends in oil production) on another (e.g., trends in airline or automobile use).

In other focuses of econometric modeling, attention is directed to network influences [51]. For instance, often explored are how prices, information, and quantities reverberate in a particular social or economic system. The key advantage offered by the methods of the current invention is the ability to better blend information from scalar measures (i.e., information, prices, quantities) that often serve as input to network measures with recognized dynamic processes (e.g., forces affecting capital markets, stock/bond prices, etc.), thus enabling enhanced network descriptions that normally would not be easily defined.

16. For the mentioned capabilities and those related as a consequence of their impacting oxygen homeostasis, it is also appreciated that the metrics outlined by Eqs. (1)-(19), and others listed in the section on Description of Alternative Embodiments and those described, but not expressly listed, including the goal to determine various "hidden" coefficients that are normally accessible from solutions to inverse problems that follow from methods suitable for exploring network problems and their associated rules (e.g., use of formal language theory, (FLT)), as well as features identified from findings listed in the included Figures, can be expressed to appreciate trends in these measures from repeat measures that, when compared to group-level measures of healthy subjects, or to themselves, can serve to indicate the presence of anomalous behaviors.

It is also recognized that these trends can be acquired from wireless wearable devices equipped to perform time-series Hb measures and linked to cloud computing environments. This arrangement can serve to identify anomalous trends that may warrant immediate attention (e.g., call to emergency services) or additional follow-up. It is further recognized that the ability to obtain the information detailed herein from a variety of tissue types and time-dependent measures supports generation of Big-Data sets, whose group-level behaviors can be mined using various machine learning methods.

As noted elsewhere in this invention, all of the above biomedical and health assessment uses can be accomplished by adoption of a variety of sensing formats (e.g., contact, non-contact, endoscopic), whose primary signal may or may not be subsequently transduced into another form as accomplished by photoacoustic or fluorescence/bioluminescence phenomena.

Method of Implementing Preferred Embodiment

1. Relationships Among Co-Varying Elements of the Hb Signal:

Covariation among state variables in a dynamical system can be appreciated by examining state-space plots. This may be accomplished in the case of Hb time series measures by plotting the time-varying changes in oxyHb against concurrent variations in deoxyHb (i.e., $\Delta$oxyHb vs. $\Delta$deoxyHb). While quasi-steady-state changes in component values are defined relative to their respective temporal means in exemplary results presented in this application, the described method is not dependent on using the temporal mean as the reference condition.

We can additionally represent relative changes in the dependent Hb-signal components (i.e., totalHb, $HbO_2Sat$, $HbO_2Exc$) within the $\Delta$Hb state-space plot, by introducing associated axes whose orientations with respect to the primary axes follows directly from their definitions. Thus, concurrent changes in totalHb levels (ΔtotalHb) can be appreciated by introducing an axis rotated by 45 degrees counterclockwise about the origin with respect to the ΔdeoxyHb axis. Appreciation of co-variations in ΔHbO$_2$Exc can be gained by introducing a fourth axis orthogonal to the ΔtotalHb axis. By adding a line demarcating (ΔdeoxyHb, ΔoxyHb) pairs that correspond to hemoglobin oxygen saturations above and below the temporal mean value, ΔHbO$_2$Sat values can also be determined from the plot.

2. Finite-State Network Representation of the Hb Signal:

Depicted in FIG. 1(a) is the coordinate system resulting from the procedure described in the preceding section. The regions of the plane corresponding to positive and negative changes for each signal component (relative to its temporal mean value) also are indicated in FIG. 1(a). The mathematical dependencies among the signal components determine the orientations of the ΔtotalHb and ΔHbO$_2$Exc axes and ΔHbO$_2$Sat demarcator relative to the ΔdeoxyHb and ΔoxyHb axes. At every measurement time frame, each image voxel was assigned a number from 1 to 10, determined by the algebraic signs of the five Hb-component values. These assignments set the stage for treating resting-state dynamics as the behavior of a network containing 10 vertices, or nodes, with pairs of nodes connected by edges that are weighted by one or more of the features listed in "Method of Procedure for Transforming Time-Varying Measures of Hb Signal to Yield Coefficients of Network-Dependent Features of the Hemoglobin Signal" (e.g., probabilities of transitions between pairs of nodes, dwell times at the pre-transition and post-transition nodes, Hb-component mean values at the pre-transition and post-transition nodes, Hb-component fluxes).

A novel aspect of the present application is the exploration of different pairings of Hb signal components as primary axes, in addition to the FIG. 1(a) coordinate system, in recognition of the possibility that physiological processes and disease dependences may trend more directly with one or more of the dependent Hb-signal components. As an illustration, FIG. 1(b) shows the ΔHbO$_2$Sat vs. ΔtotalHb coordinate system.

3. Quantification of Inter-State Transition Coefficients Comprising the Network Adjacency Matrices:

Every reconstructed image time series has the form of a $N_t \times N_v$ matrix, where $N_t$ and $N_v$ are the numbers of measurement time frames and image voxels, respectively. In turn, each voxel occupies exactly one of the ten Hb States at every time frame. Using i and j for the time and space variables, respectively, $s_{ij}$ denotes the State of the $j^{th}$ voxel in the $i^{th}$ time frame, and is the $ij^{th}$ element of the $N_t \times N_v$ matrix S.

The method described in this application for counting transitions differs from that of prior applications, in that here we compare the Hb State in each time frame to the one immediately following it. A consequence of this "synchronous" definition is that, here even the case where a voxel is in the same state at successive times frames is counted as a transition, with the result that 100 transition types are defined, in contrast to 90 in prior applications [45].

In the method of the preferred embodiment, the transition matrix T is a linear combination of two time-shifted copies of S:

$$T_{1:N_t-1,1:N_v} = 10 \cdot (S_{1:N_t-1,1:N_v} - 1) + S_{2:N_t,1:N_v}. \quad (1)$$

Thus all values in the ranges of 1-10, 11-20, ..., 91-100 correspond to transitions from State 1, 2, ..., 10 (the nomenclature we adopt is that this is the pre-transition State), while all values ending in 1, 2, ..., 9, 0 correspond to transitions into State 1, 2, ..., 9, 10 (the post-transition State). We also note that the dimensions of T are $(N_t-1) \times N_v$ (just as a n-story building has n−1 inter-story staircases), and that the interval between the $i^{th}$ and $(i+1)^{th}$ time frames constitutes the $i^{th}$ time step.

3.1. Computation of Probabilities for Transitions Between States

The absolute transition count for a given subject and the $k^{th}$ transition type, k=1-100, is obtained by first generating the matrix $U_k$, whose $ij^{th}$ element is:

$$(U_k)_{ij} = \begin{cases} 1, & T_{ij} = k \\ 0, & T_{ij} \neq k \end{cases}. \quad (2)$$

Summing $U_k$ over its spatial dimension and transposing yields $C_k$, the $1 \times (N_t-1)$ matrix of type-k transition counts, whose $i^{th}$ element is:

$$c_{ki} = \sum_{j=1}^{N_v} (U_k)_{ij}. \quad (3)$$

Performing the computation in Eq. (3) for all 100 transition types produces C, a $100 \times (N_t-1)$ matrix of transition counts, where $C_k$ is the $k^{th}$ row of C.

To reduce the information in C to a form amenable to inter-subject comparison and quantitative analysis, we first sum over the temporal dimension, to produce the 100-element transition-count vector c, whose $k^{th}$ element is:

$$c_k = \sum_{i=1}^{N_{TS}} C_{ki}, \quad (4)$$

and $N_{TS} = N_t - 1$ is the number of measurement time steps. Each ck value is directly proportional to the measurement duration. Accordingly, for inter-session or inter-subject comparisons we normalize c to the sum of all values in c:

$$P = 100 \frac{c}{\sum_{k=1}^{100} c_k}. \quad (5)$$

The $k^{th}$ element of (dimensionless) P is the probability for the $k^{th}$ transition type, in units of percent.

3.2. Computation of Pre-Transition and Post-Transition Dwell Times:

There are ten transition types that correspond to a voxel being in the same Hb state in successive time frames (using the single-number indexing defined in Eq. (1), they are types 11n−10, where n=1-10). The term we adopt to describe occurrences of these transition types is that the voxel "dwells in" State n during that time step. For each transition type k, two distinct average dwell times are extracted from transition matrix T. These are the mean number of time frames that voxels dwell in the pre-transition State ($s_1 = \lceil k/10 \rceil$ where the "ceiling function" $\lceil x \rceil$ is the smallest integer ≥x) prior to transition k, and the mean number of frames that they dwell in the post-transition State ($s_2 = k - 10(s_1 - 1)$) following it. We introduce the quantities $(n_{s_1}^k)_{ij}$ and $(n_k^{s_2})_{ij}$, to denote the pre- and post-, transition dwell times, respectively, for the $i^{th}$ time-step transition in the $j^{th}$ voxel. That is, $n_{s_1}^k$ is the number of time frames dwelt in State $s_1$ prior to a type-k (i.e., from $s_1$ to $s_2$) transition, and $n_k^{s_2}$ is the number of time frames dwelt in State $s_2$ following a type-k transition. We further introduce $\tau_k^{(1)}$ and $\tau_k^{(2)}$ to denote the mean pre- and post-transition dwell times, respectively, for type-k transitions. Thus we have:

$$\tau_k^{(1)} = \frac{1}{c_k}\sum_{j=1}^{N_v}\sum_{i=2}^{N_{TS}}(U_k)_{ij}(n_{s_1}^k)_{ij}, \tau_k^{(2)} = \frac{1}{c_k}\sum_{j=1}^{N_v}\sum_{i=1}^{N_{TS}-1}(U_k)_{ij}(n_k^{s_2})_{ij}, \quad (6)$$

where $(U_k)_{ij}$ (Eq. (2)) is 1 (0) if a type-k transition does (does not) take place in the $j^{th}$ voxel in the $i^{th}$ time step, and $c_k$ (Eq. (4)) is the total number of type-k transitions in the image time series. The two dwell times have different time-step summation limits in the index-i summations in Eq. (6), because pre (post)-transition dwell time cannot be evaluated for transitions that occur during the first (last) time step.

For the ten $s_n \rightarrow s_n$ transition types there can be two or more consecutive occurrences of the same type, and this would produce multiple values of $n_{s_1}^k$ and $n_k^{s_2}$ for a single dwell period. In these instances, only the largest values of $n_{s_1}^k$ and $n_k^{s_2}$ in each sequence of consecutive occurrences are included in the Eq. (6) summations.

Each dwell time computed via Eq. (6) is a grand-average (GA) quantity, in that averaging is performed simultaneously over the spatial and temporal dimensions. However, inspection of large numbers of measurement-channel time series and image time series led us to hypothesize that systematic variations in the dwell times can be present, in either the spatial or temporal dimension. To allow for further examination of these possibilities, we have developed two other summation schemes, to compute the spatial means of the (possibly) position-dependent temporal mean values and the temporal means of the (possibly) time-varying spatial mean values of the pre- and post-transition dwell times. However, except when otherwise stated, GA dwell-time values are considered in the exemplary results.

3.3. Quantification of Transition-Linked Hemoglobin-Component Concentration and -Saturation Changes:

The Hb states and transitions are defined in a manner that is independent of component amplitudes, and hence of distance from the axes or origin in FIG. 1. At the same time, image time series contain information on the magnitude of each Hb-signal component, which can be combined with the categorical information to compute the average levels of the five components of the Hb signal before and after each type of transition, as well as the average amounts by which those levels change during transitions.

The starting point for the concentration- and saturation-dependent quantities is fifteen matrices, three for each component of the Hb signal, which are interrelated in the following way:

$$\Delta^2 D_{1:N_t-1,1:N_v} = \Delta D_{2:N_t,1:N_v} - \Delta D_{1:N_t-1,1:N_v},$$

$$\Delta^2 E_{1:N_t-1,1:N_v} = \Delta E_{2:N_t,1:N_v} - \Delta E_{1:N_t-1,1:N_v},$$

$$\Delta^2 O_{1:N_t-1,1:N_v} = \Delta O_{2:N_t,1:N_v} - \Delta O_{1:N_t-1,1:N_v},$$

$$\Delta^2 S_{1:N_t-1,1:N_v} = \Delta S_{2:N_t,1:N_v} - \Delta S_{1:N_t-1,1:N_v},$$

$$\Delta^2 To_{1:N_t-1,1:N_v} = \Delta To_{2:N_t,1:N_v} - \Delta To_{1:N_t-1,1:N_v}, \quad (7)$$

where $\Delta D$, $\Delta E$, $\Delta O$, $\Delta S$ and $\Delta To$ denote the image time series (formatted as $N_t \times N_v$ matrices) of $\Delta$deoxyHb, $\Delta HbO_2Exc$, $\Delta oxyHb$, $\Delta HbO_2Sat$ and $\Delta totalHb$, respectively, while $\Delta^2 D$, $\Delta^2 E$, $\Delta^2 O$, $\Delta^2 S$ and $\Delta^2 To$ are the corresponding concentration and saturation changes that attend each transition.

Proceeding in parallel with the transition probability derivation, the analogue of Eq. (2) is:

$$(U_k^X)_{ij}^{(1)} = \begin{cases} \Delta X_{ij}, & T_{ij} = k \\ 0, & T_{ij} \neq k \end{cases}, \quad (8)$$

$$(U_k^X)_{ij}^{(2)} = \begin{cases} \Delta X_{(i+1)j}, & T_{(i+1)j} = k \\ 0, & T_{(i+1)j} \neq k \end{cases},$$

$$(U_k^X)_{ij}^{(3)} = \begin{cases} \Delta^2 X_{ij}, & T_{ij} = k \\ 0, & T_{ij} \neq k \end{cases},$$

where X is any of the Hb-signal components D, E, O, S or To in Eq. (7).

Thus the $U_k^X$ arrays with superscripts '(1)', '(2)' and '(3)' contain pre-transition, post-transition, and transition-associated change data, respectively. We sum the arrays defined in Eq. (8) over position and time, and account for inter-subject variations in measurement duration by normalizing to the transition count:

$$(\mu_k^X)^{(1)} = \frac{1}{c_k}\sum_{j=1}^{N_v}\sum_{i=1}^{N_{TS}}(U_k^X)_{ij}^{(1)}, (\mu_k^X)^{(2)} = \frac{1}{c_k}\sum_{j=1}^{N_v}\sum_{i=1}^{N_{TS}}(U_k^X)_{ij}^{(2)}, \text{ and} \quad (9)$$

$$\phi_k^X = \frac{1}{c_k}\sum_{j=1}^{N_v}\sum_{i=1}^{N_{TS}}(U_k^X)_{ij}^{(3)}. \quad (10)$$

The $(\mu_k^X)^{(1)}$ parameter is the mean value, per transition, of pre-transition concentration or saturation, while $(\mu_k^X)^{(2)}$ is the corresponding post-transition value. We refer to $\phi_k^X$ which is the average change in Hb component X per type-k transition, as a transition flux. A related quantity called the transition mass $(m_k^X)$, is the average change in Hb component X per unit of time, and is found by computing:

$$m_k^X = \frac{1}{N_{TS} \cdot N_v}\sum_{j=1}^{N_v}\sum_{i=1}^{N_{TS}}(U_k^X)_{ij}^{(3)}. \quad (11)$$

As in the case of pre-transition and post-transition dwell times, we have developed alternative formulations for the pre-transition and post-transition mean values, and for the transition fluxes, that allow for examination of the possibility of spatial variations in the temporal means and fluxes, or temporal fluctuations in the volumetric means and fluxes. Unless otherwise noted, exemplary results consider the GA means and fluxes defined in Eqs. (9) and (10).

3.4. Quantification of Features Derived from Thermodynamic Considerations:

3.4.1. Boltzmann Energy Distribution of Transition Types:

A plausible hypothesis for the observed differences among probabilities for the various transition types is that the probabilities reflect a transition type-dependence in the energy expenditures associated with the transitions. Then the dependence of energy on transition type k can be estimated by computing, for each value of k in turn:

$$p_k = \frac{P_k}{100} = \frac{e^{-x_k}}{\sum_{n=1}^{100} e^{-x_n}}, \qquad (12)$$

where $P_k$ is the $k^{th}$ element of the transition probability defined in Eq. (5), and the exponent $x_k$ is the dimensionless quantity $x_k = \varepsilon_k/(kT)$ [$\varepsilon_k$=energy with physical units (e.g., J, kcal), k=Boltzmann constant, T=absolute temperature]. Eq. (12) can be rearranged to:

$$p_k e^{-x_1} + \ldots + p_k e^{-x_k} + \ldots + p_k e^{-100} = e^{-x_k} \Rightarrow$$

$$-p_k e^{-x_1} - \ldots + (1-p_k) e^{-x_k} - \ldots - p_k e^{-100} = 0 \Rightarrow$$

$$-p_k - \ldots + (1-p_k) e^{x_1 - x_k} - \ldots - p_k e^{x_1 - x_{100}} = 0. \qquad (13)$$

Applying Eq. (13) to each of the k=1-99 transition types in turn (k=100 is omitted because it does not contribute independent information, since $p_{100} = 1 - \sum_{k=1}^{99} P_k$) yields a system of linear equations:

$$\begin{bmatrix} p_1 & p_1 & \cdots & p_1 & p_1 \\ 1-p_2 & -p_2 & \cdots & -p_2 & -p_2 \\ -p_3 & 1-p_3 & \cdots & -p_3 & -p_3 \\ \vdots & \vdots & \ddots & \vdots & \vdots \\ -p_{99} & -p_{99} & \cdots & 1-p_{99} & -p_{99} \end{bmatrix} \begin{bmatrix} e^{x_1-x_2} \\ e^{x_1-x_3} \\ e^{x_1-x_4} \\ \vdots \\ e^{x_1-x_{100}} \end{bmatrix} = \begin{bmatrix} 1-p_1 \\ p_2 \\ p_3 \\ \vdots \\ p_{99} \end{bmatrix}, \qquad (14)$$

from which it follows that the 99 differences between $x_1$ (and it should be noted that the transition type that we label as '1' is an arbitrary choice) and each of $x_2$ through $x_{100}$ can be obtained by computing:

$$\begin{bmatrix} x_2 - x_1 \\ x_3 - x_1 \\ x_4 - x_1 \\ \vdots \\ x_{100} - x_1 \end{bmatrix} = -\ln \left( \begin{bmatrix} p_1 & p_1 & \cdots & p_1 & p_1 \\ 1-p_2 & -p_2 & \cdots & -p_2 & -p_2 \\ -p_3 & 1-p_3 & \cdots & -p_3 & -p_3 \\ \vdots & \vdots & \ddots & \vdots & \vdots \\ -p_{99} & -p_{99} & \cdots & 1-p_{99} & -p_{99} \end{bmatrix}^{-1} \begin{bmatrix} 1-p_1 \\ p_2 \\ p_3 \\ \vdots \\ p_{99} \end{bmatrix} \right). \qquad (15)$$

3.4.2. Gibbs Free Energies for Individual Transition Types and for Pre-Transition States:

Applied here is a sequence of assumptions and inferences that parallels the reasoning that has been previously applied for analysis of protein-protein interaction (PPI) networks [52,53]. Thus we make the ensemble assumption that many copies of each Hb State are present at many locations throughout the tissue structure from which the measurement data are obtained, and that every type of transition occurs at multiple locations and time steps throughout the measurement period. Therefore, we can assume an ensemble of States and transition types, akin to an ideal gas mixture.

For the set of ten transitions having a given pre-transition State in common, the counterpart of the free energy defined for a specified protein within an interacting set (e.g., Eq. (1) in Ref 54) is:

$$G_j^X = pwa|(\mu_j^X)^{(1)}| \cdot \ln \frac{pwa|(\mu_j^X)^{(1)}|}{\sum_{i=1}^{10} |(\mu_{10(j-1)+i}^X)^{(2)}|}, \quad j = 1-10, \qquad (16)$$

where $(\mu_{10(j-1)+i}^X)^{(2)}$ post-transition mean values, for Hb component X, as defined in Eq. (9), and $pwa|(\mu_j^X)^{(1)}|$ is the probability-weighted average of absolute values of the associated pre-transition mean values (Eq. (9)); that is:

$$pwa|(\mu_j^X)^{(1)}| = \frac{\sum_{i=1}^{10} P_{10(j-1)+i} \cdot |(\mu_{10(j-1)+i}^X)^{(1)}|}{\sum_{i=1}^{10} P_{10(j-1)+i}}, \quad j = 1-10, \qquad (17)$$

where the $P_{100(j-1)+i}$ are elements of the transition probability defined in Eq. (5).

The counterpart of Eq. (16) for the case of free energies of individual transition types is simpler, in that here there is no need to compute an averaged value for the pre-transition Hb-component mean. Instead, we have:

$$G_k^X = |(\mu_k^X)^{(1)}| \cdot \ln \frac{|(\mu_k^X)^{(1)}|}{|(\mu_k^X)^{(2)}|}, \quad k = 1-100. \qquad (18)$$

We note that free energies, at either the State or transition-type level, can be computed for any quantity that has distinct pre-transition and post-transition values. For example, the transition dwell times (Eq. (6)) are appropriate inputs for computation of free energy values using either Eq. (16) or Eq. (18).

It also should be noted that here, as in the cited work on PPI networks, the quantities defined in Eqs. (16) and (18) have the same units as the considered network feature (i.e., % for $\Delta HbO_2Sat$, M for the other Hb-signal components, time steps for dwell times), rather than conventional energy units. This is not cause for concern, since the values computed using Eqs. (16) and (18) are called Gibbs free energies only by analogy to the case of ideal-gas mixtures from classical thermodynamics [https://www.tf.uni-kiel.de/matwis/amat/def_en/kap_2/advanced/t2_4_1.html]. However, evidence is presented to show there likely is a proportionality between the computed "energy" and some type of true physical energy.

3.4.3 Network Entropies for Individual Subjects and for Subject-Group Means:

Transitions are observed (although with different probabilities) from every State to every State. Equivalently, the States are nodes of a fully connected network, with an edge connecting every pair of nodes. Therefore, every node has the same topological degree (i.e., the number of other nodes to which a specified node is connected) of 9, and an explicit computation of the node-degree entropy S (e.g., Eq. (2) in Ref. 55) will always produce the trivial result S=0. However, the same mathematical formula:

$$S = -\sum_k [p(k) \cdot \log p(k)] \qquad (19)$$

still can be used to compute a meaningful entropy value, by interpreting the summation index k as denoting all possible values for a specified network edge weight, and p(k) as the probability distribution for the selected weight [56]. In contrast to Gibbs free energy, an entropy value can be computed for any kind of network weight, whether the weight values are properties of individual network nodes (e.g., Hb-component mean values, dwell times) or of transitions between pairs of nodes (e.g., transition probabilities, fluxes); a trade-off is that only a single entropy value is obtained for the network. Exemplary entropy values have been computed for each of the state-transition and Hb-component features described in sub-sections 3.1-3.3.

Experimental data used in the exemplary computations are divided into four sub-groups, corresponding to the tumor-bearing and contralateral unaffected breasts (i.e., T and U, respectively) of women with breast cancer, and the left and right breasts (L and R, respectively) of women who did not have breast cancer at the time of measurement. For a selected type of network weight (i.e., w), the entropy computation for each individual subject was performed by first summing the values of for each set of 10 transition types having the same pre-transition State (i.e., $W_j = \Sigma_{i=1}^{10} |w_{10(j-1)+i}|$), then combining the W values for both breasts into a single set and identifying the smallest (i.e., $W_{min}$) and largest (i.e., $W_{max}$) values overall. The range from $W_{min}$ to $W_{max}$ was then divided into a finite number of equally spaced bins, and the fraction of W values in each bin was evaluated, for each breast separately. (For exemplary-results computations the number of bins was 9, to mirror the number of mathematically possible network-degree values in a 10-node network; but we recognize that the bin number is an adjustable parameter.) The bin-dependent fractions are used as the p(k) values in Eq. (19), to compute a network entropy value for each breast and the selected network weight.

The approach taken to compute network entropies from group-mean network weights is similar to the individual-subject method; the difference is that here the W values for all four groups—L, R, T and U—are combined for the purpose of determining $W_{min}$ and $W_{max}$. Consequently, the group mean-based entropies are not expected to equal the inter-subject means of the individual-subject values.

3.5. Biomarker Utility Validation:

It is understood that the "Method of Implementing Preferred Embodiment" can generate multiple classes of adjacency matrices having dimensions of at least 10×10, along with a variety of other features having well-defined structures, for each set of specified State definitions and each selected class of time-dependent measures. It is further understood that, while the processing strategies employed herein consider summations over the space and time dimensions, data reduction strategies that retain spatial or temporal resolution also can be applied. Thus, it is recognized that the applied methods are capable, in the limit, of generating arbitrarily large coefficient spaces. Further, many of these features are disease sensitive, as evidenced in exemplary findings presented below.

For those skilled in the Art, it is recognized that a variety of Artificial Intelligence-Machine Learning algorithms are available for identifying which classes of coefficient measures offer useful disease detection or monitoring, or, more generally, which classes provide the most accurate and specific measures of any biological property of interest. For instance, it can be expected that multivariate data exploration/reduction/visualization tools that were originally developed to process data sets comprising two or more types of 'omics data [56 a] will be extendible to data sets that include one or more of NIRS and other forms of non-invasive measure, along with, optionally, conventional medical-test results, biopsy data, one or more types of 'omics data, etc. It is further understood that such methods can be implemented via three basic strategies; unsupervised, reinforcement or supervised learning approaches each of which can employ a variety of computational methods (e.g., support vector machine, various forms of deep learning, discriminant analysis, among others [56b]). Supporting on-demand longitudinal monitoring, the specific sensing approach employed herein offers notable practical advantages that provide for one or more targeted intact-tissue measures. Offering access to an arbitrarily large coefficient space, the noted methods are well positioned to identify optimal biomarker performance either for stand-alone non-invasive time-series measures, or in combination with varied panomic data. Identified biomarkers can be applied with the goal of discriminating the impact of lifestyle choices or for the detection or monitoring of chronic diseases. Additionally, as described by methods outlined in the Alternative Embodiments, that include evaluation of any class of physiological time-series measure for which any of a multitude of possible state-definitions can be applied, allow access to multiple representative network and thermodynamic measures, many of which are otherwise deeply hidden.

Exemplary Data for the Preferred Embodiment

Here we report group-average findings obtained from subject groups, comprising women who are and are not affected with unilateral breast cancer, that evaluate the coefficient types defined above. To assist comprehension of these data, we begin by describing subject preparation and data-collection and data-processing methods used, although these are not essential parts of the invention.

1. Diffuse Optical Tomography: Optical time series measures of the breast were acquired using a custom-made, high density tomography system [25]. Notable capabilities of this unit include the capacity to examine both breasts simultaneously while, if desired, exposing the breast to concurrent defined viscoelastic deformations. The illumination-detection scheme employed a dual-wavelength laser source (760, 830 nm) that was time-multiplexed to allow for simultaneous recording of light intensities from all elements of the sensing array with a scan rate of ~2 Hz. In all, each sensing head contains 64 dual-wavelength sources and 32 detector elements that are evenly divided within a two-stage arrangement.

2. Subject Preparation: System operation supports examination of the breast while the subject is comfortably seated. Having a hinged arrangement, the top portion of the sensing array can be adjusted to allow for controlled contact in an anatomically conforming manner. In all, sensing elements are arranged to support essentially a full circumferential measurement. Findings reported herein were derived from publicly accessible, deidentified data [57]. In all, data from 63 subjects were explored, 18 with confirmed breast cancer (6-right breast, 12-left breast, average tumor size ~2.7 cm, range 0.5-6 cm) and 45 non-cancer subjects, 23 of whom had evidence of various types of non-malignant pathologies in one breast or in both. A more detailed description of enrolled subjects is given in [4]. It is worth mentioning that findings reported here involve the same subject groups as in [4] and exploration of the same data. Different are the methodologies applied for data analysis.

3. Data Collection: Following initial setup, automated system calibration was performed to identify optimal gain settings. Subsequently, resting-state measures were acquired for a period lasting ~5-10 minutes.

4. Data Preprocessing: Data were screened for evidence of degradation of signal quality caused by excessive signal attenuation by very large breasts or by poor skin-contact for very small breasts, using methods previously described [4]. To avoid introducing bilateral signal bias, channels excluded from one breast were also excluded from the other, resulting in symmetric data sets. Also, to avoid under-sampling biases, only measures from women that included at least 60% of all data channels were considered. Experience showed that operating limits are breasts having cup sizes varying from B to DD.

5. 3D Image Reconstruction: Tomographic reconstructions were achieved by first normalizing measured signal intensities to the respective temporal mean values of each data channel, then solving a system of linear equations using a modified perturbation formulation based on solutions to the diffusion equation [58,59]. Computed wavelength-dependent absorption coefficient values were subsequently transformed to yield spatial maps of the time-varying components of the hemoglobin signal. This produced five sets of maps for each breast, corresponding to spatiotemporal variations in the independent and dependent Hb components.

6. Evaluation of inter-breast differences for subjects with unilateral breast cancer: Here we use the generic symbol $Y_{ij}$ to denote any of the node-weight or edge-weight network features. For any transition type, each study subject has distinct values of $Y_{ij}$ for the left and right breast (i.e., $Y_{ij}{}^l$ and $Y_{ij}$r, respectively). To generate group-mean metrics and test statistics for the beast-cancer subjects (e.g., FIG. 8), it is likewise necessary to specify tumor-breast and unaffected-breast values for the subjects in the breast cancer group. This is straightforward for the women having left-breast tumors, for whom we define:

$$Y_{ij}{}^t(q)=Y_{ij}{}^l(q), Y_{ij}{}^u(q)=Y_{ij}{}^r(q), \quad (20)$$

where $Y_{ij}{}^t$ and $Y_{ij}{}^u$ are the feature values for the tumor-bearing and unaffected breast, respectively, and q is the subject index. For subjects having right-breast tumors, however, we cannot simply equate $Y_{ij}{}^t$ to $Y_{ij}{}^r$ and $Y_{ij}{}^u$ to $Y_{ij}{}^l$, as that would confound tumor effects with any intrinsic left-right asymmetries that may be present. Instead, we compute:

$$Y_{ij}{}^t(q)=Y_{ij}{}^r(q)+\overline{Y_{ij}{}^l}_{NC}-\overline{Y_{ij}{}^r}_{NC}, Y_{ij}{}^u(q)=Y_{ij}{}^l(q)-\overline{Y_{ij}{}^l}_{NC}+\overline{Y_{ij}{}^r}_{NC}, \quad (21)$$

where $\overline{Y_{ij}{}^l}_{NC}$ and $\overline{Y_{ij}{}^r}_{NC}$ denote quantities averaged over all subjects in the non-cancer group. The linear adjustment operations in Eq. (21) have the effect of correcting the difference between parameter values in the tumor-bearing and unaffected breasts for left-right biases that are not related to the presence of disease. They are based on a plausible assumption that, to first order, the net inter-breast difference is the linear sum of background-asymmetry and tumor-related contributions, and that the magnitude of the former is not itself strongly disease-dependent.

7. Hb Feature Sensitivity to Short Time-Scale Behaviors: One of the criteria for the preferred data collection strategy is to apply a data sampling rate on a time scale at least comparable to those for homeostatic control mechanisms in the first (i.e., fastest) level of the three-level hierarchy (e.g., 1-2 sec), which are sensitive to prevailing oxygen levels. If this criterion is met, then evidence of controlled blood oxygenation, and of the expected disease-dependence of that control should be observable in the measured hemoglobin signal.

Figure 2A:
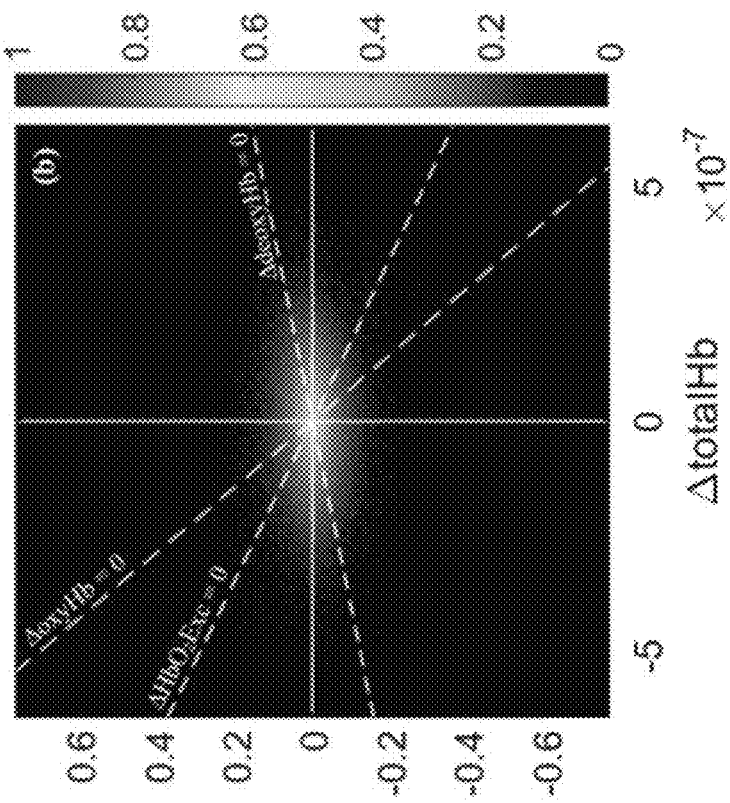
FIGS. 2(a) and 2(b) are plots of temporally coincident resting-state ΔHbO$_2$Sat and ΔtotalHb values obtained from time-series tomographic images, for FIG. 2(a) cancerous and FIG. 2(b) contralateral unaffected breast of a representative clinical-study subject (50 y/o, BMI=44, C size breast, with a 4 cm left-breast intraductal carcinoma), respectively, in accordance with the invention. This representation of information from the Hb-image time series reveals magnitude (i.e., distances of plotted points from the origin) and probability of occurrence [i.e., color-axis values are percentage of all (ΔtotalHb, ΔHbO$_2$Sat) pairs, on a nonlinear (i.e., $7^{th}$ root) scale] of resting-state image values, while at the same time the spatial and temporal-sequence information are disregarded. Each dashed white line, as denoted in FIG. 2b, is the locus of (ΔtotalHb, ΔHbO$_2$Sat) points at which one of the three other Hb-signal components is equal to its baseline mean value (e.g., ΔdeoxyHb=0 on the positively sloped contour).
Figure 2B:
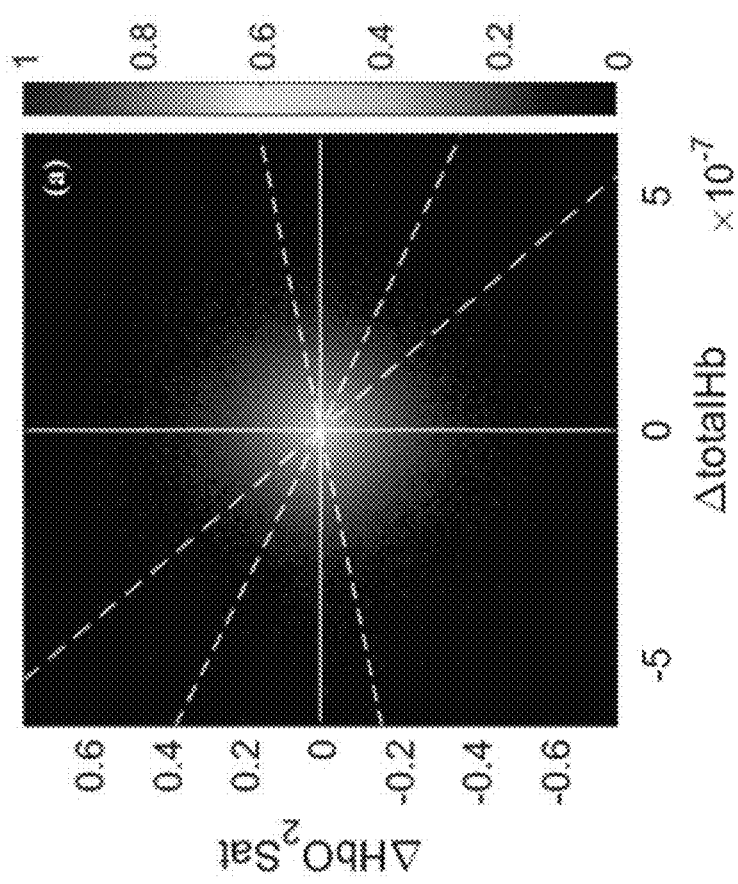
Figure 3B:
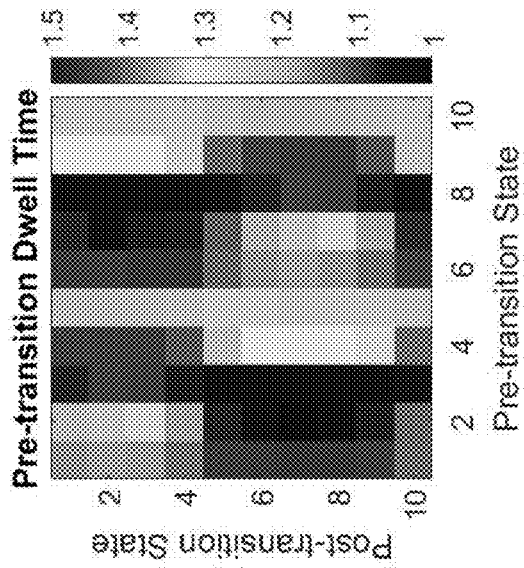
FIGS. 3(a)-3(d) are graphical representations of the following.
Figure 3D:
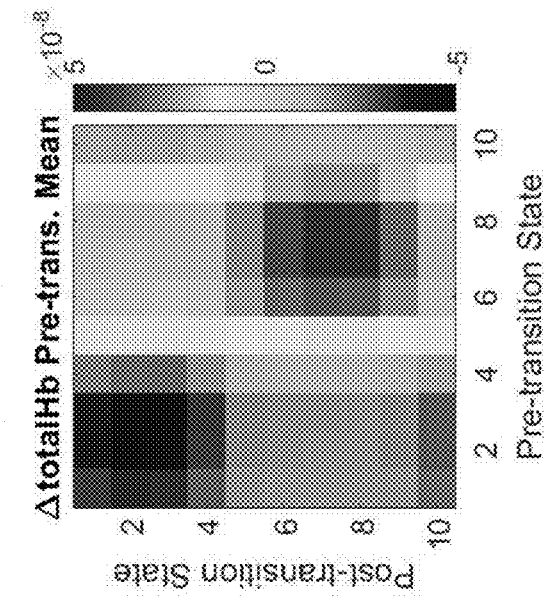
Figure 3A:
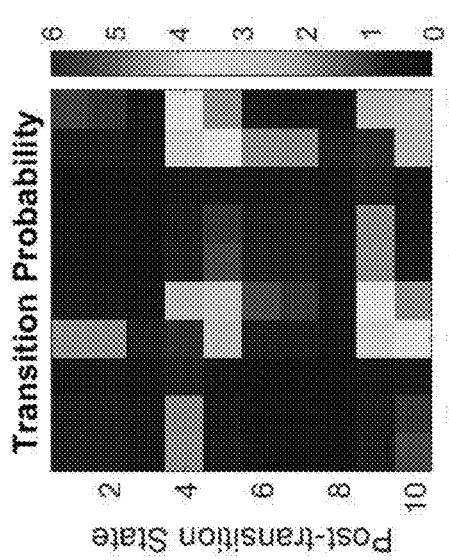
Figure 3C:
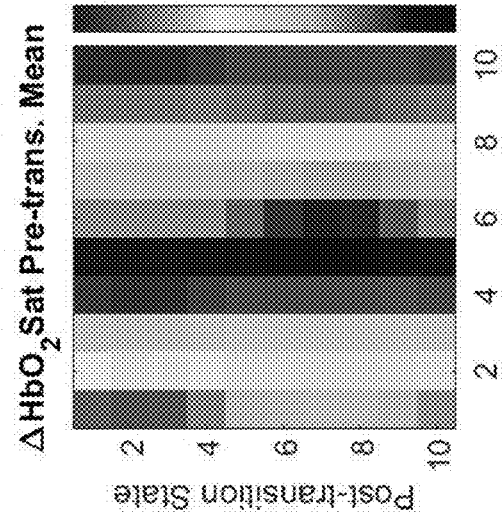

Shown in FIG. 2 are representative plots of the scatter of the simultaneously paired relative amplitude values of $\Delta HbO_2Sat$ and $\Delta totalHb$ observed from whole-breast measures acquired in the resting state, for a representative individual. Seen are values for an affected (FIG. 2(a)) and unaffected (FIG. 2(b)) breast acquired concurrently. Inspection reveals a distinct bias favoring larger amplitude variations in oxygen saturation relative to changes in total Hb levels for affected compared to unaffected breast, which is the expected response given known loss of feedback control arising from the tumor-associated disorganized vascular bed.

8. Information Pertaining to Homeostatic Control Mechanisms in Network Weights:

Apart from the notably different aspect ratios in the FIG. 2, the initial impression is that these plots are featureless clouds of points. However, as shown in the following sections, the methods described herein reveal various forms of hidden structures that are not discernible from applications of canonical time- or frequency-based analyses.

a. Background; Review of Relevant Previously Reported Findings:

An informative way of displaying network-weight data for a selected individual feature is in the form of an adjacency matrix; in this format, the column index (i.e., numbers displayed along the horizontal axis) for each transition type is its pre-transition State, the row index (i.e., numbers displayed along the vertical axis) is the post-transition State, and the feature values (i.e., numbers displayed along the color bar) are indicated by the colors applied to the 100 small squares in the 10×10 array [45].

Figure 4:
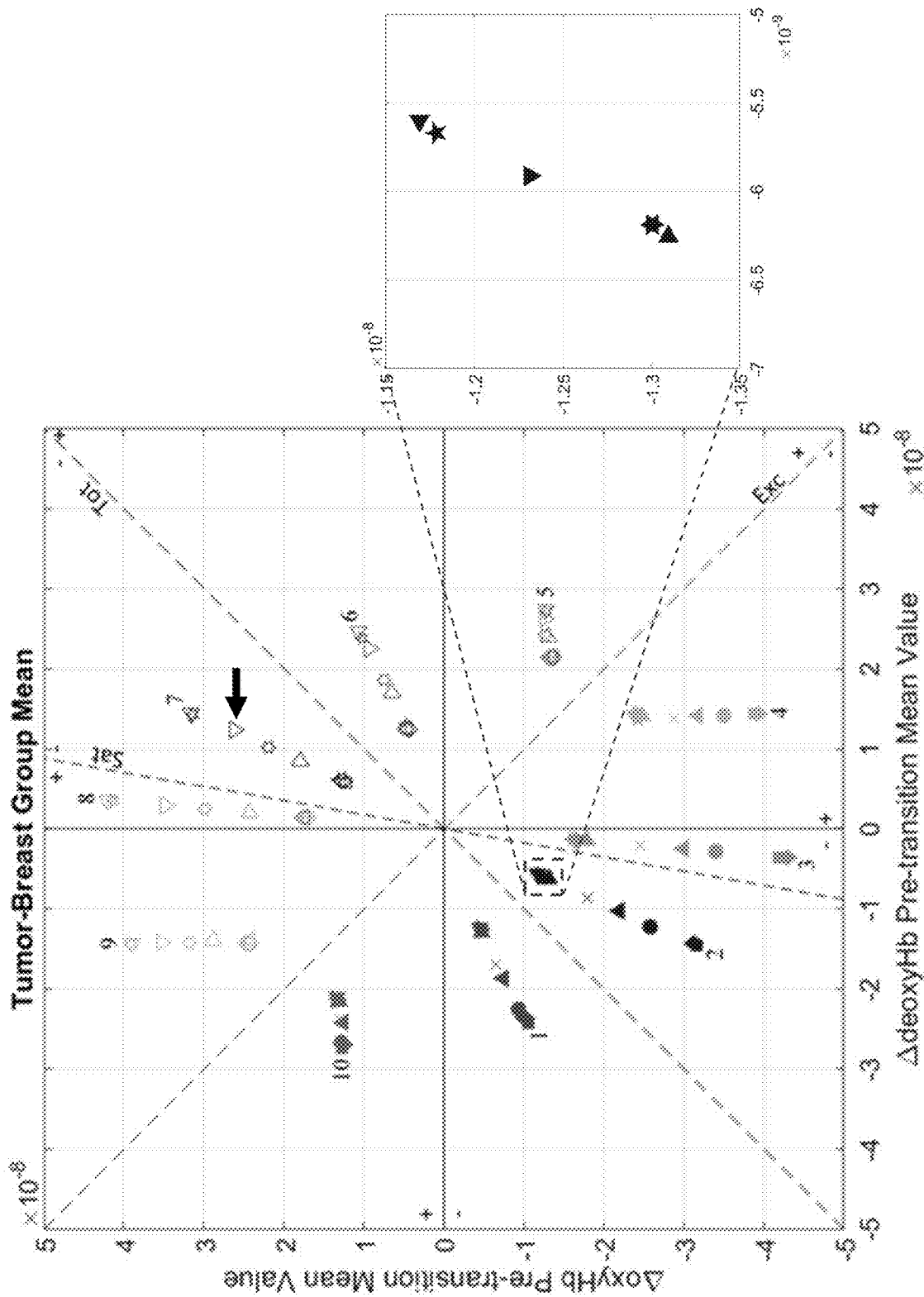
FIG. 4 is a plot of ΔoxyHb pre-transition mean values vs. ΔdeoxyHb pre-transition mean values (units, M), for the tumor-bearing breast of subjects with unilateral breast cancer, in accordance with the invention. Each distinct symbol shape denotes a different one of the 10 post-transition States (●,○=state 1; ■,□=state 2; ◆, ◇=state 3; ▲,△=state 4; ▶, ▷=state 5; ▼, ▽=state 6; ◀, ◁=state 7; ★, ☆=state 8; ✱, ✻=state 9; x,+=state 10). Each combination of symbol color (Red: states 1,6; Blue: states 2,7; Green: states 3,8; Cyan: states 4,9; Magenta: States, states 5,10) and open-or-filled symbol denotes a different one of the 10 pre-transition States, as labeled in the plot. Arrow identifies an exemplary transition; from State 7 into State 6. Dotted lines identify additional Hb-component axes identified in FIG. 2(a). Identified by the inset is an expanded view of points that otherwise appear coincident.

Adjacency matrices for a variety of network weights are shown in FIG. 3. While the examples shown are group-mean values for the tumor breast group (T), qualitatively similar results are obtained for the contralateral unaffected breasts from the same group (U), and for the left (L) and right (R) breast groups from unaffected controls (but with different feature-value ranges that are similar to each other but have statistically significant differences from the T results). The transition probability matrix is highly symmetric, while vertical striping is noticeable in the Hb-component pre-transition mean values and dwell-time matrices. This distinction reflects the fact, noted in "Method of Implementing Preferred Embodiment," that transition probabilities inherently are properties of the network edges, while the dwell times and Hb-component means are properties of the nodes. For each nodal feature, the corresponding post-transition adjacency matrix is nearly equal to the transpose of the pre-transition matrix. A casual inspection reveals that the patterns for the different adjacency matrices are weakly correlated.

b. Demonstration of Non-obvious Co-dependences Between Pairs of Network Features:

Inspection of adjacency matrices, even when they are displayed side by side as in FIG. 3, does not immediately suggest the possibility of functional relationships between the network-weight values for a selected pairing of features. The existence of identifiable relationships becomes apparent when the values in two adjacency matrices are plotted as the x- and y-coordinates of 100 points, as in the example shown in FIG. 4. We have determined that a plot qualitatively similar to that in FIG. 4 is obtained for any of the 10 unique pairings of Hb-component pre-transition means, or for any of the 10 unique pairings of post-transition means; here we have selected a pairing that emphasizes the finding that cyan-colored points (i.e., transitions with pre-transition States 4 and 9) lie on lines parallel to the $\Delta oxyHb$ axis, while magenta-colored points (i.e., transitions with pre-transition States 5 and 10) lie on lines parallel to the $\Delta deoxyHb$ axis. In contrast, the sets of data points for the remaining six Hb States have a nearly radial orientation. Thus it is found that there are clear qualitative differences in the co-dependent behavior for different State-dependent transition types. Further inspection of the figure yields additional evidence of hidden structure.

c. Sequence of Data Points is the Same in All States: Interpretation:

Closer inspection of FIG. 4 reveals that the 10 points in each co-linear set can be separated into two 5-point subsets: the five nearest the origin (and substantially coincident (see inset of representative expanded view)) represent transitions in which the algebraic sign of the ΔtotalHb signal reverses (e.g., from a value above the temporal mean (positive) to one below it (negative)), while the five farther from the origin (and more widely separated from each other) correspond to transitions in which the sign of ΔtotalHb does not change. (The typical trend seen, proceeding from farthest to nearest the origin, for any given co-linear set is: States 2, 3, 1, 4, 10, 5, 9, 6, 8, 7 for points having negative ΔdeoxyHb values, with the latter five being mainly coincident. A similar, but reflected, trend is seen for points having positive ΔdeoxyHb values). This observation suggests an important role that adjustments in the totalHb signal have in determining patterns within the various adjacency matrices. We have further explored this phenomenon by comparing the probabilities for sign-reversing and sign-preserving transitions, as shown in FIG. 5.

The values plotted here are the ratio of the original transition probability matrix (for the T, U and L group means) to a copy of the same matrix in which rows 6-10 are interchanged with rows 1-5. The consequence of the row exchange is that every value plotted in FIG. 5 compares the probabilities for a sign-preserving transition and a sign-changing transition, and in every case the sign-preserving probability is notably larger. This indicates that transitions that have smaller adjustments in the ΔtotalHb signal (i.e., sign-preserving) to maintain the steady-state are favored over those requiring larger adjustments. Supporting this observation is the finding that, when the probabilities of sign-preserving and sign-changing transitions are compared (Mann-Whitney U test), we find statistically highly significant differences between their median values, with p-values of $2.5 \times 10^{-5}$ (T), $3.4 \times 10^{-8}$ (U), $1.2 \times 10^{-6}$ (L), $2.6 \times 10^{-8}$ (R). To the best of our knowledge, this hidden feature, reflecting trends in tissue oxygen extraction and delivery, has not previously been identified from a resting-state measure.

Figure 5C:
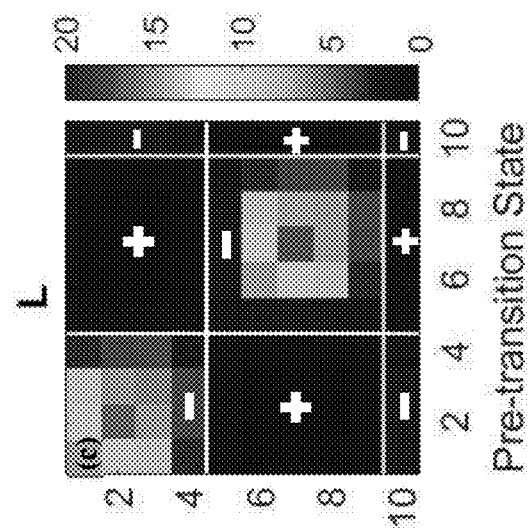
FIGS. 5(a)-5(c) are plots revealing dependence of transition probability on the algebraic sign of ΔtotalHb. Plotted is the original probability matrix divided by a transformed matrix wherein rows 6-10 are interchanged with rows 1-5.
Figure 5B:
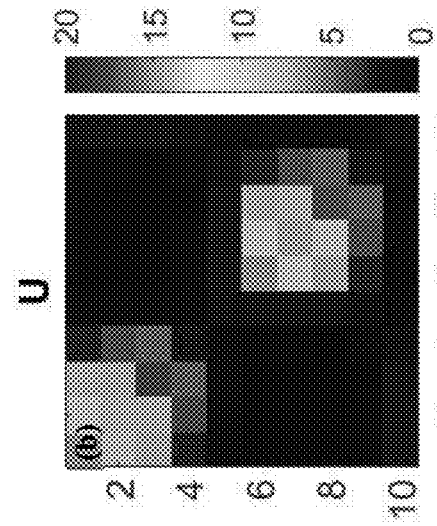
Figure 5A:
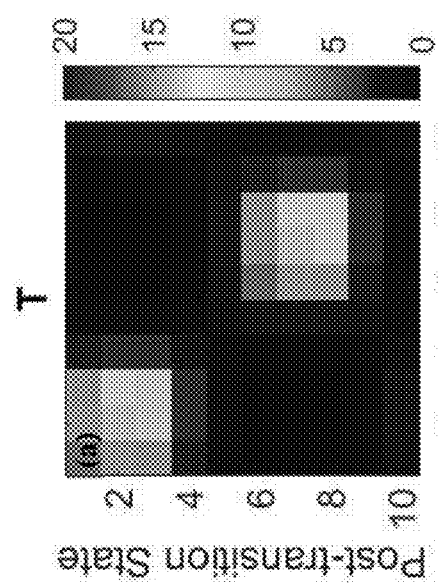

Also revealed by the ratios plotted in FIG. 5 is a disease dependence, in that the ratios of sign-preserving to sign-reversing probabilities are smaller for the T group than for either U or L. To quantify the observed bias, for each subject (18 with breast cancer, 45 without) we first computed the sum of probabilities for all 50 sign-reversing transition types, separately for each breast. Student t-tests (unequal variance) were then performed to evaluate the differences between the sets of individual-subject transition probability sums, for every pairing of subject-breast groups (T vs. U, T vs. L, U vs. L, etc.). Thus it was found that sign-reversing transitions are significantly less probable in the T group than in U, L or R (p=0.0021-0.0497), and that all three comparisons of non-cancer breast groups do not reach significance (p=0.08-0.97).

d. Nonlinear Functional Forms Identifiable in Transition-Spanning Co-dependences:

The sort of co-dependency analysis depicted in FIG. 4 evaluates the interactions between two features (and, as recognized among the alternative embodiments, larger numbers of features can be simultaneously considered) at the same "end" of a transition (i.e., pre-transition component-1 vs. pre-transition component-2, or post-transition component-1 vs. post-transition component-2). It is straightforward to examine in the same way the co-dependency between a pre-transition feature and a post-transition one, to demonstrate the influence (if any) of the former value on the latter.

Figure 6A:
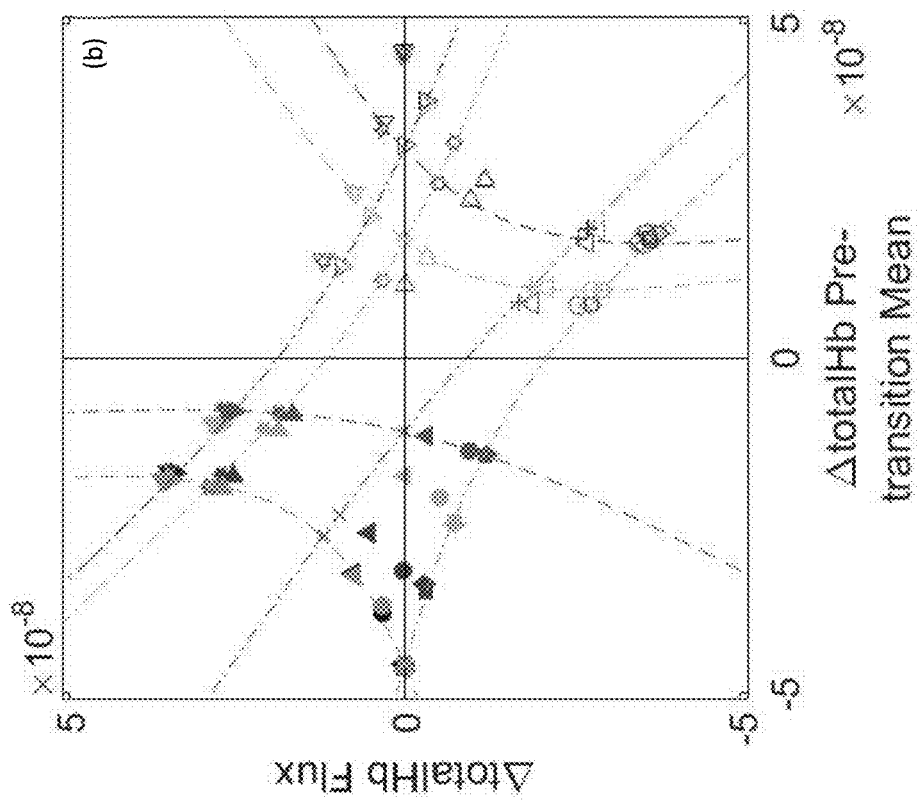
FIGS. 6(a) and 6(b) are nonlinear co-dependency plots shown to closely fit computed hyperbolic functions.

An example of the type of co-dependent influence that can be revealed is shown in FIG. 6(a), where pre-transition ΔHbO$_2$Sat is plotted vs. post-transition ΔtotalHb (T-group mean values, for both parameters). In the ΔHbO$_2$Sat-vs.-ΔtotalHb counterpart of FIG. 4, each set of ten points falls on a line segment lying entirely on one side of ΔtotalHb=0; here, in contrast, they are stretched out into a curve that straddles 0. Analysis of the functional form of the curves shows an excellent fit to a hyperbola for each one, consistent with the suggestion that pre-transition ΔtotalHb determines post-transition ΔHbO$_2$Sat, via one or more mechanisms that involve saturable processes.

Our initial examinations of co-dependencies considered all possible (n=133) pairings of the transition probability, dwell time (i.e., state-transition properties), flux and pre- and post-transition mean value features (i.e., Hb-component properties) described in "Method of Implementing Preferred Embodiment." Inspection revealed that in most cases the distribution of points did not reveal evidence of distinctive structure, while others had dependences with complex forms. In the minority of cases where hyperbolic relationships similar to those in FIG. 6 are observed, none involved pairings with a State measure (i.e., transition probability, dwell time). Cases where such dependence was observed are limited to pairings in which the quantity plotted on one axis is ΔtotalHb pre-or-post-transition mean value, while on the other axis is either the post-or-pre-transition mean value, or the flux, for any of the five Hb signal components. Of the 19 pairings that show this dependence, elimination of symmetric patterns, arising from the substitution of a set of post-transition mean value for the same component's pre-transition mean values, reduces the number of unique pairings to 10.

Evidence of symmetry also is present in the plot for any of the reduced set of 10 pairings showing hyperbolic dependences. In particular, inspection of FIG. 6 (as well as the other hyperbola-revealing pairings not shown) reveals a 180° rotational symmetry element about the coordinate-system origin. Consequently, the number of unique hyperbolas falls by a factor of 2, from 10 to 5 in FIG. 6(a) and from 20 to 10 in FIG. 6(b).

Depending on the specific pairing of features considered, it may be possible to fit a hyperbola to each set of points having the same color-and-fill (i.e., the same pre-transition State), as in FIG. 6(a), or to each set of points having the same shape (i.e., the same post-transition State), as would be the case if pre-transition mean ΔtotalHb values were substituted for post-transition values (and simultaneously post-transition ΔHbO$_2$Sat for pre-transition ΔHbO$_2$Sat) in FIG. 6(a). The pairings that have 10 distinct hyperbolic dependences are: ΔtotalHb flux vs. pre-transition mean ΔtotalHb, which is plotted in FIG. 6(b), ΔtotalHb flux vs. post-transition mean ΔtotalHb, and pre-transition mean ΔtotalHb vs. post transition mean ΔtotalHb. Thus identified from the sweep of inter-feature pairings are four key findings, identifiable from evaluation of the network coefficient classes, that would otherwise remain hidden: (1) an identifiable co-dependency form, which is suggestive of the action of saturable processes, is seen for a minority of pairs; (2) this form is seen only among pairings between Hb-component features; (3) ΔtotalHb must be at least one of the features that are paired; and (4) that the pairings may be either two sets of Hb-component mean values or one mean value and a flux. These finding reinforce those identified in FIGS. 4 and 5 showing specific forms of co-dependent behaviors that are linked to adjustments in the ΔtotalHb level and are disease sensitive.

e. Reduction of Hyperbolic Co-dependences to (Disease-Sensitive) Setpoints:

Once it is known that a given set of points lie on a hyperbola, all of the information in that function can be extracted from a small number of parameters. For example, a complete hyperbola can be constructed from just a knowledge of the coordinates of the vertices and foci. That is, plots such as those in FIG. 6 can be replaced with a more condensed representation, showing only the vertex and focus, without losing any information. Accordingly, we treat the vertices and foci for a given hyperbola as a setpoint that drives or constrains the response in one co-dependent feature to changes in the other. In addition, the reduced representation simplifies the demonstration of function properties that may not be as obvious in the entire-curve representation, and it gives us a straightforward method for demonstrating disease dependence for a particular chronic disease. For example, FIG. 7(a) shows the vertex (circles) and focus (diamonds) coordinates for the ten mean pre-transition $\Delta HbO_2Sat$ vs. mean post-transition ΔtotalHb hyperbolas plotted in FIG. 6(a). Evident in this secondary plot is the division into two distinct subsets of hyperbolas constituting two distinct linear trends, one consisting of pre-transition States 3, 8, 4 and 9 (green and cyan points), and the other States 1, 6, 2, 7, 5 and 10 (red, blue and magenta points). In retrospect, close inspection of the hyperbolas in FIG. 6(a) can also reveal this division; however, the extent to which each hyperbola is rotated with respect to the coordinate axes is difficult to judge by eye in that plot. In contrast, the rotations can be precisely determined from the FIG. 7(a) plot (the line that passes through the vertices and foci for a selected hyperbola is that hyperbola's transverse axis). It follows that, while every set of transition types having the same pre-transition State has a hyperbolic dependence of one plotted feature upon the other, there are pre-transition State-dependent differences in the precise manner in which one influences the other.

Plotted in FIGS. 7(b) and 7(c) are the inter-breast differences in the vertex and focus coordinates, for the women who have breast cancer in FIG. 7(b) and for those who do not in FIG. 7(c). Deliberate use of the same axis ranges in FIGS. 7(b) and 7(c) serves to highlight the disease sensitivity in the co-dependency data; since the L-R difference is substantially smaller than T-U, the magnitude of the latter difference can be attributed to the presence of a tumor in one breast. That is, one of the effects of a tumor on the affected breast is the occurrence of shifts in the hemodynamic response setpoints.

Figure 6B:
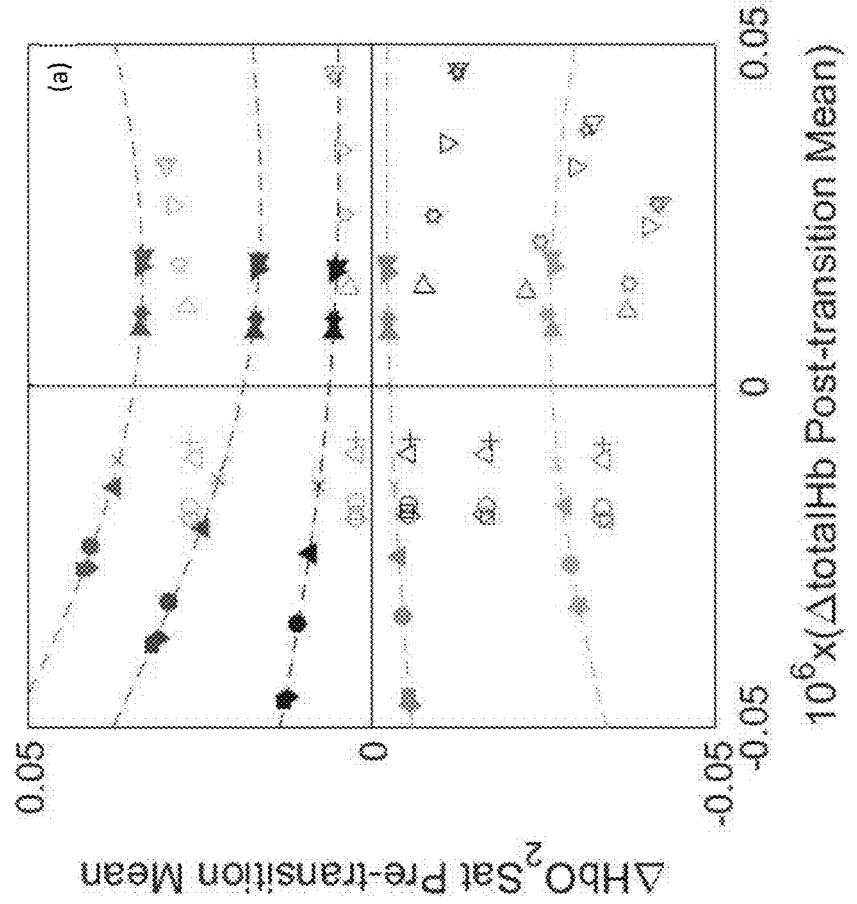
Figure 7D:
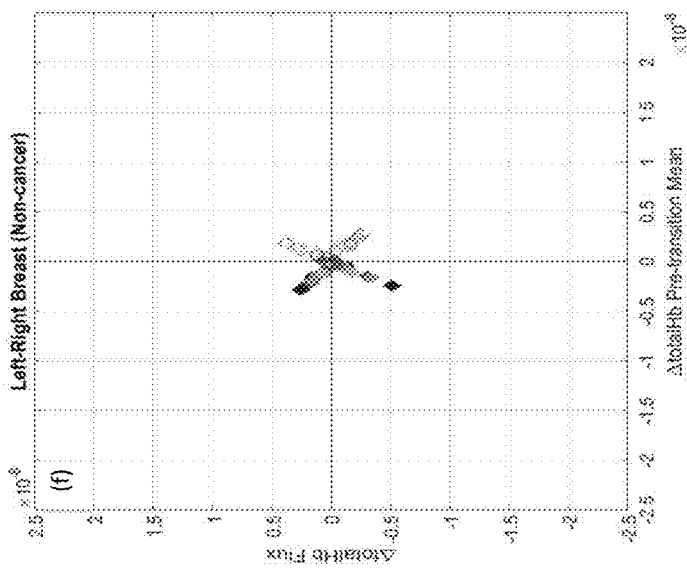
Figure 7E:
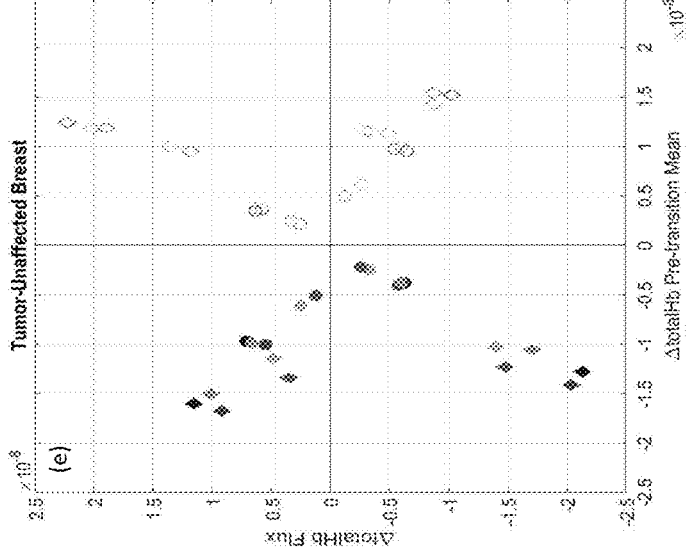
Figure 7F:
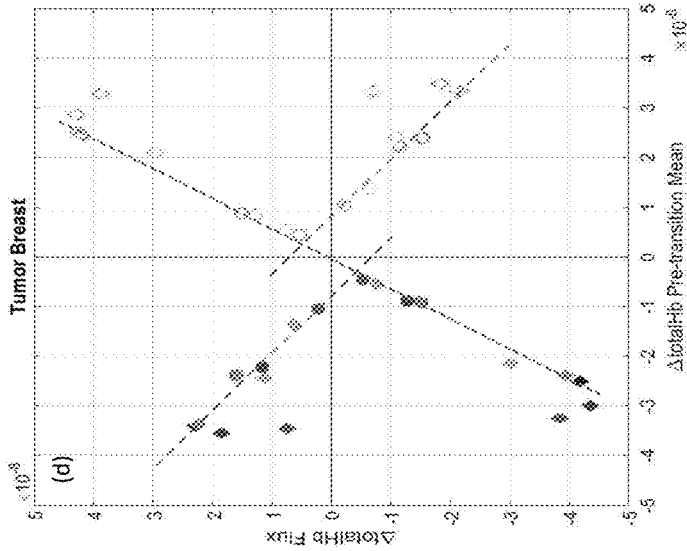

Shown in FIGS. 7(d)-7(f) are the counterparts of FIGS. 7(a)-7(c) for the ΔtotalHb flux vs. mean pre-transition ΔtotalHb hyperbolas plotted in FIG. 6(b). Consistent with the fact that the number of unique hyperbolas is larger by a factor of two in this case, twice as many points are plotted in FIGS. 7(d)-7(f) as in FIGS. 7(a)-7(c). The quadrants in which the vertices and foci lie reflect the ~90° rotation between the curves defined by points having the same symbol shape, and the curves defined by points having the same symbol color-and-fill. Tumor-associated inter-breast differences (i.e., setpoint shifts) are observed for this intra-component comparison, just as in the preceding inter-component case. Comparison of FIGS. 7(a)-(c) with FIGS. 7(d)-(f) reveal that while lines through the points plotted in the former appear to intersect the origin, in the latter it is only the QI, III values that exhibit this behavior.

Whereas setpoints are commonly identified in clinical practice, and are considered a consequence of network behaviors, the details of such networks are almost always hidden. In contrast, the methods described herein allow access to at least a portion of the network details associated with such behaviors. It is further identified, that such details can have distinctive structure that is shown to vary across different feature classes. A separate noted advantage gained from identifying the described setpoint behavior is its significant data-reduction effect. Here we demonstrate that an entire 3D time series measure can be reduced to a just few pairs of coefficients, of which whose amplitudes are disease sensitive.

f. Utility of Thermodynamic Parameters Computed from Hemodynamic-Network Features:

In this section we explore thermodynamic features accessible from the network descriptions. Being theoretically grounded, the character of this approach differs from the preceding data-driven analyses. To render the theoretical formalism more concrete, we begin with a brief consideration of its theoretical underpinnings.

Among the noteworthy findings from our examination of the various network-feature pairings (here, let X and Y denote the adjacency matrices for a selected feature pair) is that in some cases the sum, over all rows i and columns j, of products $X_{ij}*Y_{ij}$ is nearly zero. This orthogonality property suggests that (i.e., is a necessary condition for) the network dynamics may be governed by Tellegen's theorem [46,47]. However, it is necessary to rule out the possibility that the orthogonality is an incidental consequence of the fact, which becomes apparent on inspection of adjacency matrices such as those in FIG. 3, that some features (e.g., transition probability) are symmetric (i.e., $m_{ij}=m_{ji}$, where $m_{ij}$ denotes the matrix element in row i and column j), while others (e.g., transition fluxes) are antisymmetric (i.e., $m_{ij}=-m_{ji}$). A further requirement for applicability of Tellegen's theorem is that one of X and Y satisfy Kirchhoff's current law (KCL), while the other satisfies Kirchhoff's voltage law (KVL) [46,47]. The transition probability is among the network features that are found to satisfy the KCL, while the transition fluxes satisfy the KVL. It would therefore be possible to construct electrical networks equivalent to the hemodynamic finite-state network from which thermodynamic properties can be derived by applying methods described in [46,47]. The applicability of network thermodynamics to the hemodynamic network considered here argues for the position that, in fact, there could be a true correspondence between above-described thermodynamic network features as outlined in Methods, and a set of thermodynamic properties of the underlying biological system.

A finding that demonstrates the potential for clinical utility in computed thermodynamic features, which does not depend on the validity of the preceding understanding, is the patterns of individual transition-type Gibbs free energies shown in FIG. 8. The patterns seen in the first column are group-mean values of ΔG for the $\Delta HbO_2Sat$ and ΔtotalHb components of the tumor-bearing breast, while the second column shows the corresponding inter-breast differences. It is worth noting that the patterns obtained are different from those previously reported for individual network features (FIG. 3, and [45]), indicating that the information conveyed by ΔG is not redundant. Results shown in the third and fourth columns identify the p-value patterns for computed differences of T-U and L-R, as determined by Student's t-tests. A notably greater number of transition types are statistically different for $\Delta HbO_2Sat$ difference values than for $\Delta totalHb$, while there are few to no significant differences among the control group.

Examination of computed network entropies (S) gave disease sensitivity and specificity findings qualitatively similar to those from $\Delta G$. (It will be recalled, however, that a single value for $\Delta S$ is computed for each breast. Each scalar S value thus is a composite of information for all transition types, whether individually disease sensitive or not.) Of the 18 network parameters evaluated (i.e., 1 transition probability, 2 dwell times, 5 Hb-component fluxes, and 10 Hb-component pre- or post-transition mean values), the majority (11; median t-test p-value $3.0 \times 10^{-4}$) yield significant inter-breast differences for the breast-cancer group, which were notably larger than the corresponding values for the non-cancer control group (7; median p-value 0.023).

Returning to the consideration of FIG. 8, it is seen that the third-column p-value pattern for the $\Delta HbO_2Sat$ component consists of alternating bands of significant and non-significant transition types, and that the bands are oriented parallel to the main diagonal of the matrix. While the corresponding results for the other Hb-signal components are not shown, we can report that the diagonal banding is equally prominent in the $\Delta deoxyHb$ p-value pattern, and to a lesser degree (because the overall numbers of significant transition types are smaller) in those for $\Delta HbO_2Exc$ and $\Delta oxyHb$. These observations motivated us to re-visit previously generated co-dependency plots, and to apply a different labeling scheme to the data points, which would serve to group the transitions according to their distances from the main diagonal.

Figure 9:
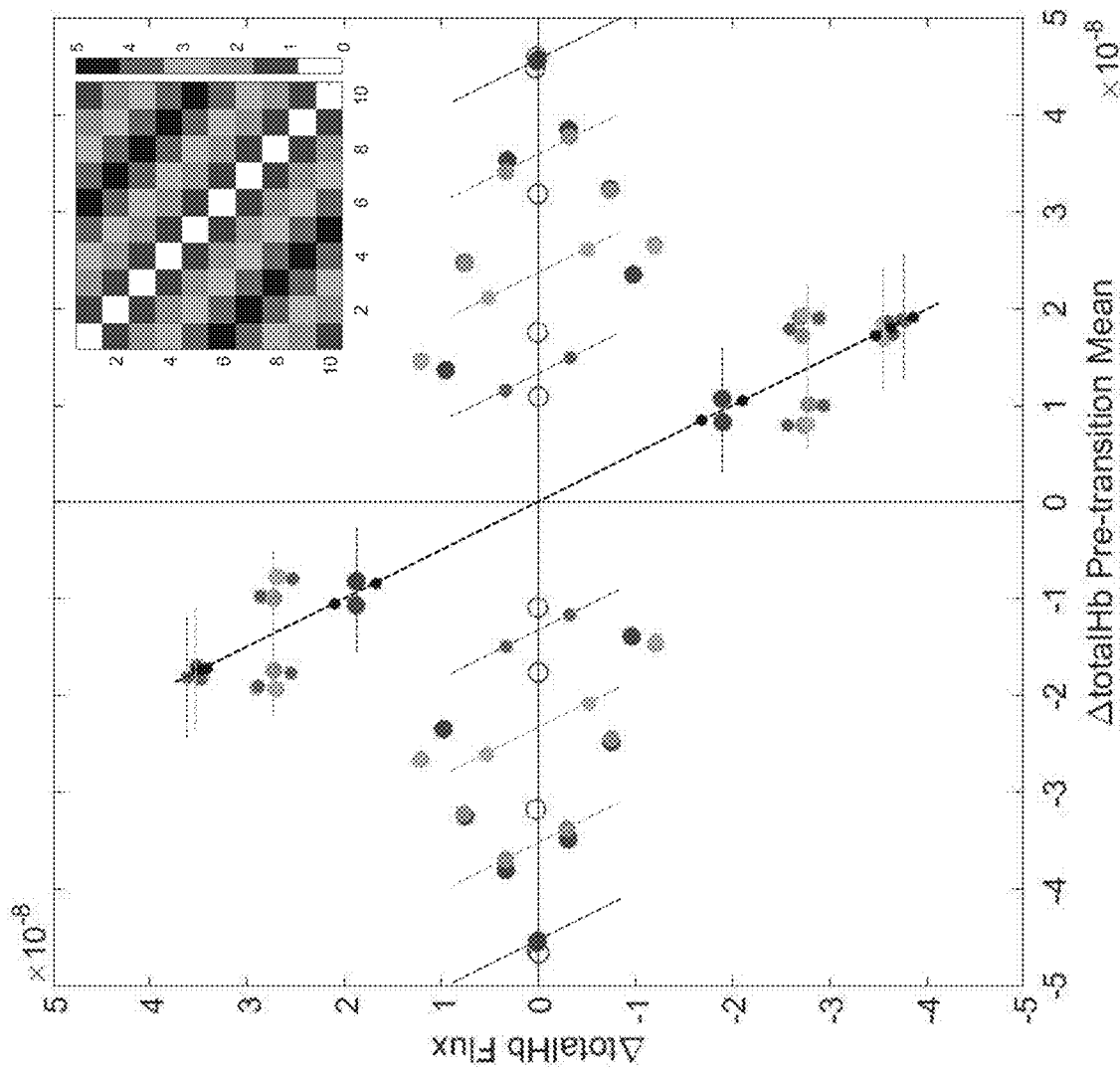
FIG. 9 is a reproduction of the FIG. 6(b) co-dependency plot (i.e., ΔtotalHb flux vs. ΔtotalHb pre-transition mean value (units, M)), with symbols colored to indicate the transition Class rather than the transition type, in accordance with the invention. Dotted color lines correspond to the horizontal and vertical limits of a given transition class. Seen is compression along the former and with expansion along the latter axes with increasing Class number. Inset nomogram shows which transition types constitute each Class, and the correspondence between Classes and symbol colors.

An example of the considered re-labeling is shown in FIG. 9, which is a copy of FIG. 6(b) wherein the white, red, green, cyan, magenta, and blue colors denote transitions that are in Class 0, 1, 2, 3, 4 and 5, respectively, and the Class of a transition is an index of the number of States by which the pre- and post-transition States are separated. For example, transitions from State 1 to either 2 or 10 are in Class 1, transitions from State 1 to either 3 or 9 are in Class 2, and transitions from State 1 to either 4 or 8 are in Class 3, etc.

Referring back to the adjacency matrices shown in FIG. 3, each column and row contains data values for a fixed pre-transition State or post-transition State, respectively. The transition-Class counterpart is that diagonals of an adjacency matrix hold the data values for the different Classes, as indicated in the color-coded nomogram inset in FIG. 9. The biological understanding that motivates this method of grouping the transition types is that the separation (in number of States) between the pre-transition and post-transition States effectively places limits on the magnitudes of the transition-associated changes in Hb-component values, and larger changes in component values would be expected to have higher energy costs. A distinctive Class dependence, not evident by casual inspection of FIG. 6(b), is revealed by the patterns of symbol colors in FIG. 9, where it can be seen that the maximal pre-transition mean $\Delta totalHb$ value decreases as a function of increasing Class number, while the maximal $\Delta totalHb$ flux simultaneously increases, reaching a limit wherein all points for Class-5 transitions lie on a straight line (blue). Thus, it appears that associated with the hyperbolic trends in this set of data values (and FIG. 6(b)) is additional organized structure that is transition Class-dependent.

When prior examinations of co-dependences between the 133 pairs of network weights were extended to include the thermodynamic features, observed in all but two instances were complex functional forms, both in the complete set of 100 transition types, and in subsets corresponding to individual pre-transition States, post-transition States, or transition Classes. One exception is the plot of individual-transition $\Delta G(\Delta totalHb)$ vs. $\Delta G(\Delta HbO_2Sat)$ shown in FIG. 10. The points corresponding to each pre-transition State fall on a curve with a hyperbolic functional form, in qualitative agreement with the behavior seen in FIG. 6(a). The notable difference is that in FIG. 10 the hyperbolas for the individual States all cluster about a single, also hyperbolic, curve. Similar to how setpoint measures were identified from the data in FIG. 6, equivalent determinations can also be performed on the FIG. 10 data, and were identified as being disease sensitive.

Figure 10A:
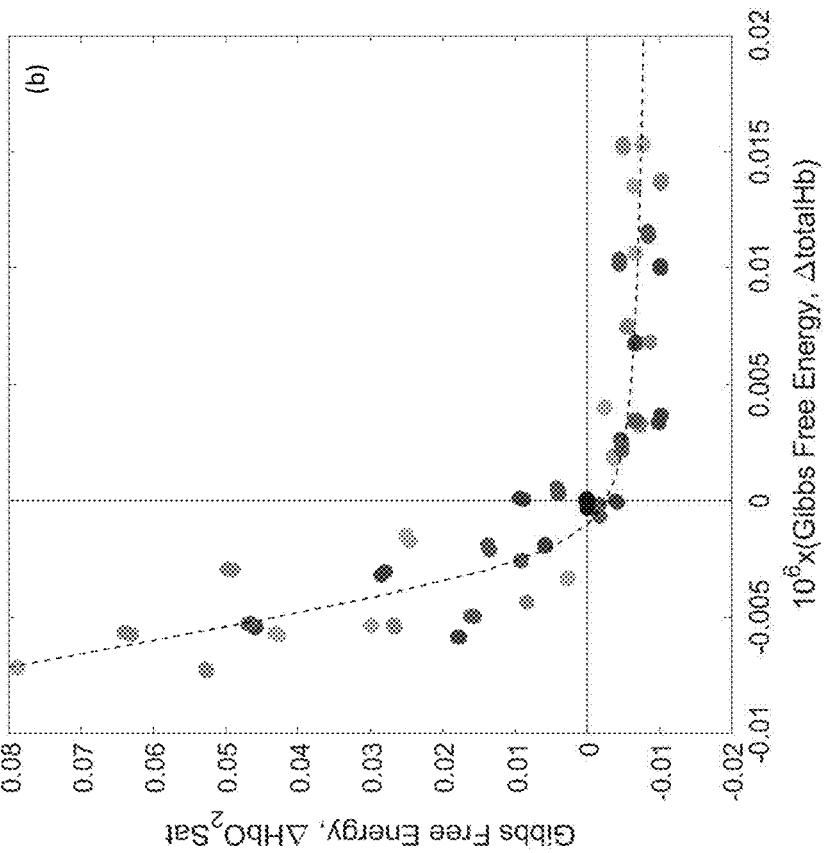
FIGS. 10(a) and 10(b) are nonlinear co-dependency plots, obtained by plotting ΔtotalHb Gibbs free energy (ΔG) values (units, M) vs. ΔHbO$_2$Sat ΔG values (%), for the tumor-bearing breast of subjects with unilateral breast cancer, all in accordance with the invention.
Figure 10B:
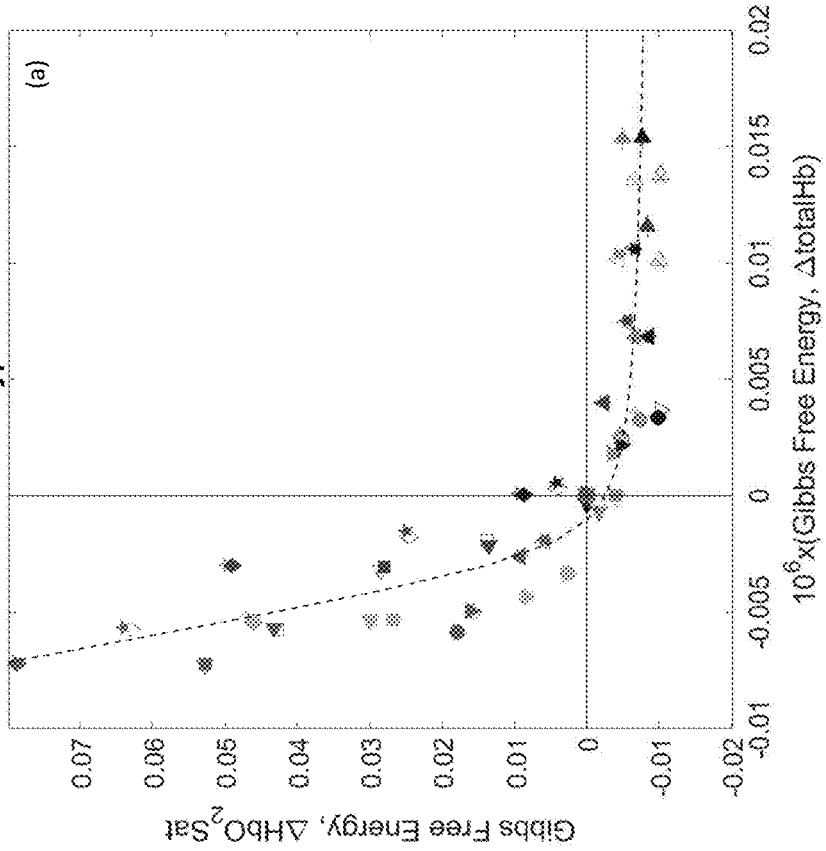

A closer inspection of FIG. 10 reveals that points corresponding to different States are in most cases restricted to one "arm" of the 100-point curve: with most of the State-2,3,7,8 points lying in Quadrant II, the majority of State-4, 5,9,10 points in Quadrant IV, and only State-1,6 points having an approximately uniform distribution along the length of the curve. Shown in FIG. 10(b) is the complementary aspect of the data-value distribution obtained by labeling the points by transition Class. A qualitative distinction between data for Class-5 transitions (blue) and all the others is evident, with the former tightly clustered about the origin and the latter having approximately uniform distributions along the hyperbolic curve. The finding that Class-5 transitions have the lowest $\Delta G$ values is consistent with the fact that these are the transitions in which all five Hb-signal components undergo changes of algebraic sign; as a consequence, the values of $\Delta G$ in the pre- and post-transition States are nearly the same. One interpretation of this behavior is that these points can be taken as acting as a thermodynamic fulcrum, whereas all others, while able to assume a range of values, are nevertheless constrained to a behavior indicative of a saturable process.

We also note, with more than passing interest, that among the 10 feature Class pairings of $\Delta G$ measures, it is only the pairing between changes in blood volume ($\Delta totalHb$) and Hb oxygen saturation that was found to exhibit a well-defined, in fact hyperbolic, behavior when explored as a thermodynamic quantity, in contrast to the multiple sets of hyperbolic behaviors seen in pairings of $\Delta totalHb$ and the other Hb forms when considered as native chemical species (FIG. 6). This suggests that a fundamental driver of tissue oxygen supply-demand balance, in addition to the recognized feedback actions that are enzymatically driven (e.g., NO mediated actions on vascular smooth muscle), is constraints arising from a thermodynamic system.

Figure 11:
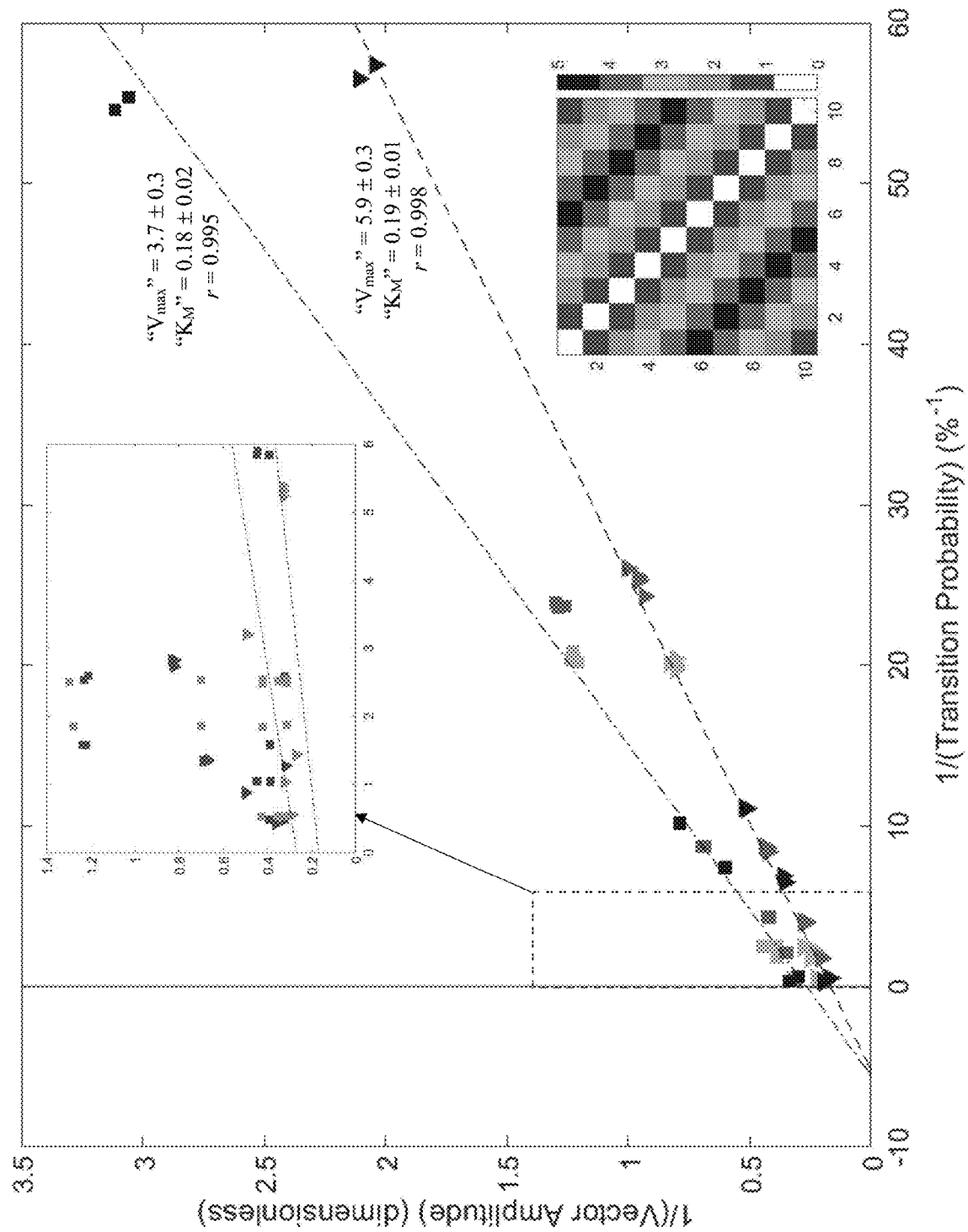
FIG. 11 is a plot of a Lineweaver-Burk representation of the dependence of vector amplitude, ($[(\Delta totalHb\ flux)^2 + (\Delta HbO_2Sat\ flux)^2 + (\Delta(dwell\ time))^2]^{1/2}$) on transition probability, in accordance with the invention for values corresponding to transition Classes 3-5. Triangular symbols: result for subjects with breast cancer, tumor-bearing breast (N=18). Square symbols: subjects without breast cancer, left breast (N=45). To accommodate the different units for the features that constitute the vector amplitude, each was converted to a dimensionless t'-score: t'=(x−m)/s, where x=individual data value, m=mean, s=standard deviation. To preserve inter-breast disparities that may be present in the original data, individual data values for each breast were referenced to the mean and standard deviation for the contralateral breast (e.g., t'(T)=(x(T)−m(U))/s(U); T=tumor-bearing breast of subjects with unilateral breast cancer, U=unaffected breast of subjects with unilateral breast cancer). Upper inset shows plot of values for transition Classes 1 and 2, revealing mainly independent behavior compared to the Classes 3-5 regression line; lower right inset nomogram identifies the transition Classes.

The preceding two examples offer evidence that Class-labeled co-dependences reveal distinctive structure that is qualitatively different from the hyperbolic dependences seen in their transition type-labeled counterparts. Accordingly, these findings have motivated a more systematic search of Class-dependent representations involving co-dependent behaviors among the various adjacency matrices which, as shown in the next section, identifies an example wherein clear evidence of hyperbolic behavior is observed. However, in contrast to the character of hyperbolic behavior involving only Hb components, we show such behavior arises in a composite metric that combines information from both Hb-component and Hb-State network features.

g. Evidence for Processes Exhibiting Michaelis-Menten Kinetics:

As noted, the presence of a hyperbolic functional form in co-dependency results suggests that enzyme-like behavior underlie the observed macroscopic relationships. Consequently, we re-examined the co-dependences between transition probability, which can be regarded as an analogue for substrate concentration (i.e., there are high and low abundances of transition types that have large and small probabilities, respectively), and the fluxes for all Hb components, which can be analogized to reaction velocities. In addition, we considered a sixth type of "flux," defined as the difference between the post- and pre-transition dwell times (just as the flux for a given Hb component is the difference between its post- and pre-transition mean values (Eqs. (7)-(10))). While none of the univariate cases reveals more than a suggestion of a hyperbolic form in the plots of flux (or |flux|) vs. probability, a hyperbolic relationship becomes apparent when the quantity plotted on the y-axis is the amplitude of a vector formed from at least two fluxes. An example, in which the considered vector is formed from the $\Delta HbO_2Sat$ flux, $\Delta totalHb$ flux, and dwell-time-difference, is shown in FIG. 11.

To strengthen the argument that the amplitude-vs.-probability trend is a hyperbola of the type that is most frequently found to describe the relationship between enzyme velocity and substrate concentration (i.e., Michaelis-Menten kinetics), we have plotted 1/(vector amplitude) vs. 1/(transition probability), because this transform (i.e., Lineweaver-Burk (LB) plot) produces a linear trend. We further note a transition-class dependence to the strength of the hyperbolic relationship: the Class 3 (cyan), 4 (magenta), and 5 (blue) data points all have the same enzyme-like dependence, while the Class 2, 1 (shown in inset) and 0 points (not shown) progressively deviate from it.

The striking linearity observed (r>0.99) is made even more remarkable by the recognition that the plotted data values are composites taken from subjects having large ranges in age (CA 53.8±11.1; non-CA 49.8±11.2) and BMI values (CA 32.3±7.9; non-CA 32.2±5.6), indicating that the observed trends are determined by strongly conserved biological phenomena.

The most prominent quantitative difference between the LB plots for the cancer and non-cancer subjects is that the apparent-$V_{max}$ is notably higher for the former group, with little change in the apparent-$K_M$ parameter. We note that this difference is consistent with well-known aspects of tumor physiology, wherein NO levels are elevated, and this factor is known to increase the $V_{max}$ of soluble guanyl cyclase, which serves to drive vasomotion in vascular smooth muscle and can be expected to impact observed macroscopic measures. Thus we find that similar to the derived setpoint behaviors accessible from determinations of the previously considered vertex and focus measures, here we gain access to yet another form of setpoint behavior, but whose particulars and trends are distinct.

Even with the presented evidence, it is natural to question how a macroscopic sensing approach could be capable of identifying data trends that are suggestive of enzyme-like behaviors. Our attention is directed to two principal elements of the considered methodology: data sampling rate, and signal averaging. For the former, we employed a sampling rate (2 Hz) that is at least as fast as needed to appreciate the Nyquist limit of the highest frequency signal (cardiac signal) and avoid notable signal aliasing. In practice, we recognize that faster sampling rates are routinely available from most NIRS-based sensing systems.

At these sampling rates, signal classification in accordance with a State definition has the effect of sampling elements of a temporal derivative. Normally, individual measures of this feature could be expected to vary notably, given physiological background behaviors. However, and because our attention is directed to State behaviors, these fluctuations can be expected to be extensively damped as a consequence of spatiotemporal averaging, wherein the number of occurrences of a given transition type often exceeds 50K. Accordingly, one advantage of a methodology aimed at characterizing State behaviors is the enormous statistical power that can be gained in determining systematic trends in the behavior of the temporal derivative. Of course, such averaging assumes that information content of the signal being averaged is substantially similar throughout the measurement period, which we hold as correct given that our measures are made under the resting state.

We further argue that a relationship between precise measures of elements of the temporal derivative of a physiological signal and underlying enzymatic behaviors that serve to generate the macroscopic behavior is also expected. Even so, this raises the question of why it should be possible to observe well defined enzyme-like behaviors.

Here our attention is directed to the many transition types that we take as reflecting the varied microenvironments of a bulk tissue. As noted above, and with some liberty, we apply a first-order biological interpretation to the adjacency matrices for State transition probability as being proportional to "substrate concentrations," and to flux measures as representing a "composite of enzyme-like behaviors." While the latter analogy seems plausible, the former, on first glance, seems less evident given that the more obvious candidate to assume the role of a "substrate concentration" would be the mean values of the Hb-components themselves. However, we note that because the State transition behavior itself is almost certainly a consequence of enzyme action, it seems reasonable that the likelihood of a transition occurring at all should in some way be proportional to an associated prevailing substrate level.

We further note that evidence of enzyme-like behavior among the Hb-component pairings that include $\Delta totalHb$ as one element of the pair (FIG. 6)—and recall that we argue that $\Delta totalHb$ is likely sensitive to actions of NO on vascular smooth muscle—also is reasonable, given the known dependence on NO (and similar effectors). A similarly reasonable expectation is that microenvironment-sensitive adjustments to oxygen demand will impact the amplitude of, e.g., $\Delta HbO_2Sat$, which suggests that ongoing resting-state functional hyperemic adjustments in blood volume ($\Delta totalHb$) will yield a saturable dependence on adjustments in $\Delta HbO_2Sat$ and related Hb-components. Accordingly, a key feature of the applied methodology is our ability to estimate microenvironment-dependent effects on macroscopic phenomena that are made possible because our applied State definitions support a description of a large number of such environments with precision.

It is this understanding that we argue logically supports extension of the methods detailed herein to other forms of physiological time-series measures. In the case of bioelectric phenomena, it is known that the signal amplitude is proportional to voltage-dependent ion-channel activity. Finer details that include the frequency dependence of such behaviors, which in the case of brain activity is strongly affected by prevailing connectivity patterns, among other factors, suggest that State definitions that recognize the primary frequency components of this signal, along with the expectation that each of these will vary about a temporal mean value in the steady state, indicates that, similar to the varied transition probability patterns seen for the hemodynamic measures, analogous phenomena are likely to occur with bioelectric measures. Different here, however, is the number of assignable states.

Unlike the more limited number of plausible states arising from the five recognized components of the Hb signal, the same number of states for bioelectric phenomena will yield 32 states ($2^5$) along with corresponding adjacency matrices having dimensions of at least 32×32. Apart from this, all other assignable phenomena such as pre- and post-transition dwell times, similar pre- and post-transition mean amplitude of the frequency components, along with the associated flux and mass measures, directly follow.

The suggestion that co-dependent phenomena among the various adjacency matrices may prove highly structured (e.g., hyperbolic, and hence yield setpoint measures), we argue also follows for the same reasons offered to account for such behaviors in the case of Hb-signal measures: i.e., the applied State definitions reflect a large range of tissue microenvironments, and hence corresponding adjustments in the "substrate levels" should influence composite enzyme-driven reactions that ultimately impact macroscopically observable behaviors.

The reverse argument, which considers the myriad of enzymatic reactions occurring in cells and conclude that this multiplicity should serve to significantly limit any reasonable assignment derivable from structured macroscopic behaviors, overlooks the fact that while the number of enzyme types in tissue is truly large, the number that can be expected to have a notable impact on specific forms of observable phenomena is much smaller. For instance, it has long been recognized that force generated by muscle contraction is directly proportional to the number of actin-myosin bridges formed, coupled with the hydrolysis of ATP by myosin-ATPase.

FIGS. 4, 6-11) that may have the added benefit of easily define setpoints (e.g., FIGS. 7, 11). In cases where the structured co-dependency is more complex, available are a variety of classification methods (e.g., k-nearest neighbors algorithm, support vector machine, etc.) that can serve to distinguish the presence of disease or impact of lifestyle choices.

h. Internal Validation of Thermodynamics-Based Features

Figure 12B:
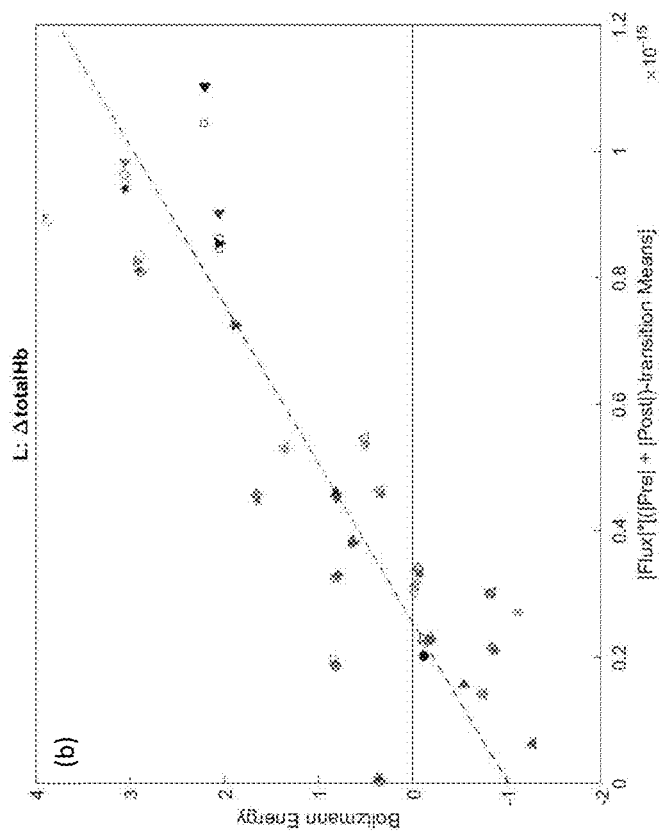
FIG. 12(b) is a plot of individual transition-type Boltzmann energies vs. the product |ΔtotalHb flux|*(|pre-transition mean ΔtotalHb|+|post-transition mean ΔtotalHb|), in accordance with the invention. Points for 90 transition types are plotted; "transitions" from each State to itself are omitted.
Figure 12A:
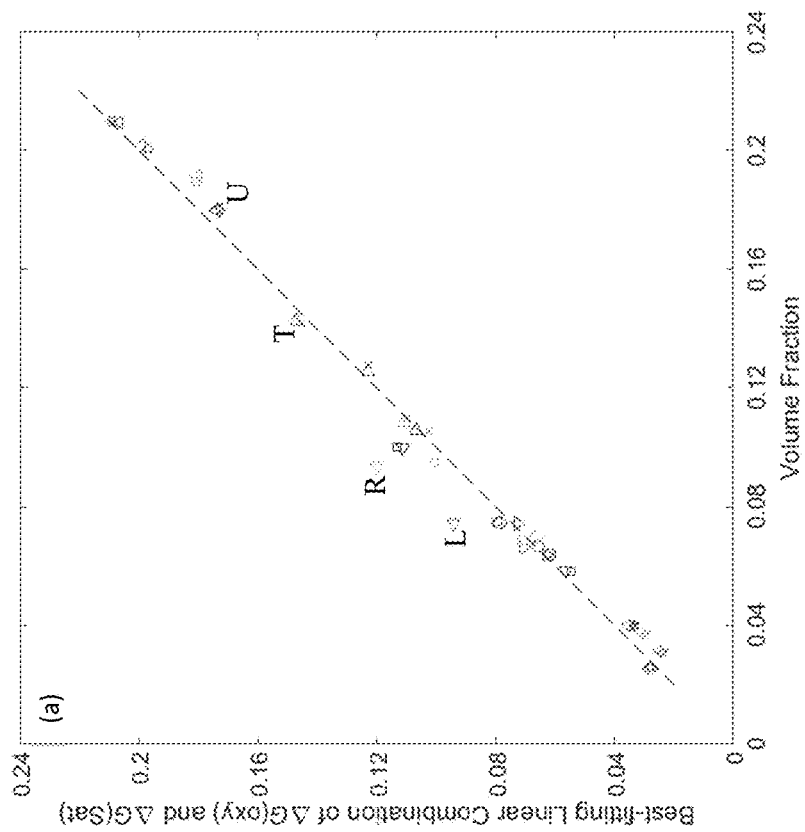
FIG. 12(a), (b). Evidence supporting validation of applied thermodynamic measures.

A question that particularly arises with regard to computed thermodynamic features is whether the underlying assumptions—e.g., the postulated analogies between ensembles of States and transition types, and mixtures of ideal gases—can be internally validated. (Although it is recognized that the features that are here referred to as "Gibbs free energy," "network entropy" and "Boltzmann energy distribution" may prove to have practical utility regardless of any theoretical validation.) One approach we took, by analogy to the classical thermodynamic relationship between Gibbs free energies ($\Delta G$) and equilibrium constants, was to determine if the pre-transition State $\Delta G$s (Eq. (16)) are correlated with the time-averaged tissue-volume fractions in those States. Findings summarized in Table 1 show that $\Delta G(\Delta HbO_2Sat)$ and $\Delta G(\Delta totalHb)$, singly or in combination, have low-to-moderate correlations with the State volume fraction (V). In contrast, the combination of $\Delta HbO_2Sat$ and $\Delta oxyHb$ (which singly has near-zero correlation with V) produces a strikingly positive correlation, for each of the four subject-breast categories. Plots of volume fraction vs. the best-fitting linear combination of $\Delta HbO_2Sat$ and $\Delta oxyHb$, for all four groups, are shown in FIG. 12($a$), and demonstrate a strong correspondence between computed thermodynamic features and a well-defined macroscale phenomenon.

TABLE 1

Correlations between pre-transition State volume fraction and pre-transition State Gibbs free energy ($\Delta G$), for selected univariate and bivariate combinations of Hb-components.

| | Pearson Correlation Coefficient and 95% CL | | | | | |
|---|---|---|---|---|---|---|
| Group | $\Delta HbO_2Sat$ | $\Delta totalHb$ | $\Delta HbO_2Sat$ & $\Delta totalHb$ | $\Delta oxyHb$ | $\Delta oxyHb$ & $\Delta totalHb$ | $\Delta oxyHb$ & $\Delta HbO_2Sat$ |
| T | 0.75 | 0.83 | 0.83 | 0.01 | 0.89 | 0.9993 |
| | [0.22 0.94] | [0.42 0.96] | [0.42 0.96] | [−0.62 0.64] | [0.58 0.97] | [0.9969 0.9998] |
| U | 0.56 | 0.54 | 0.58 | 0.07 | 0.68 | 0.989 |
| | [−0.11 0.88] | [−0.14 0.87] | [−0.08 0.89] | [−0.58 0.67] | [0.09 0.92] | [0.950 0.997] |
| L | 0.68 | 0.73 | 0.74 | 0.10 | 0.83 | 0.992 |
| | [0.08 0.92] | [0.18 0.93] | [0.20 0.93] | [−0.57 0.69] | [0.41 0.96] | [0.966 0.998] |
| R | 0.58 | 0.57 | 0.60 | 0.04 | 0.72 | 0.980 |
| | [−0.07 0.89] | [−0.10 0.88] | [−0.04 0.89] | [−0.60 0.66] | [0.16 0.93] | [0.915 0.995] |

This recognition calls attention to factors affecting states of health and chronic disease, and to expected actions of OS, which is a known driver for changes in genetic and, more commonly, epigenetic expression. Accordingly, a key thrust of this invention is to build on the wealth of experience gained from understandings derived from panomic measures. As such, we believe that the wealth of biomarkers accessible from the applied methods are well positioned to complement existing precision-medicine objectives, and that they potentially can serve to accomplish meaningful guidance as a stand-alone technique.

As documented herein, examination of trends among pairing of coefficients involving two or more adjacency matrices, in some instances were demonstrated as representative of having a highly structured co-dependency (e.g., Additional validation computations were performed to evaluate dependences between the Boltzmann energy distribution of the transition types on linear, bilinear, and quadratic functions of the fluxes and pre- and post-transition means for the different Hb components, in the expectation that if the computed energy levels in fact do correspond to physical energies between different microscopic configurations, then there will be at least one macroscopic amplitude-dependent parameter whose values are (at least approximately) determined by those energy levels. One example of a significant relationship is shown in FIG. 12($b$), where Boltzmann energies are plotted against the product of $\Delta totalHb$ |flux| and the sum of the pre- and post-transition |mean values| for $\Delta totalHb$. For the L-group data in FIG. 12($b$) (which includes 90 data points, with the "transitions"

from each State to itself omitted), the correlation coefficient is 0.86 (95% confidence interval=0.79-0.90). Correlations for the three other breast groups are similar [T: 0.80 (0.71-0.87), U: 0.78 (0.68-0.85), R: 0.84 (0.76-0.89)], while the slope of the best fit line for T [2.6 (2.2-3.0)] is significantly lower than those for U [4.8 (4.0-5.7)], L [4.0 (3.5-4.5)] or R [3.9 (3.4-4.5)], while the differences among the latter three slopes are not significant.

i. Contrast Between Network-Feature Findings for Functional Imaging Data and for Random-Number Data:

In recognition that many of the quantities presented in the above figures are obtained by application of an extensive sequence of data transforms (e.g., 3D-tomography, modified Beer-Lambert, computation of network adjacency matrices, thermodynamic measures), in this section we have undertaken additional control measures to explore whether such transforms, per se, can explain some of the features seen.

Figure 13A:
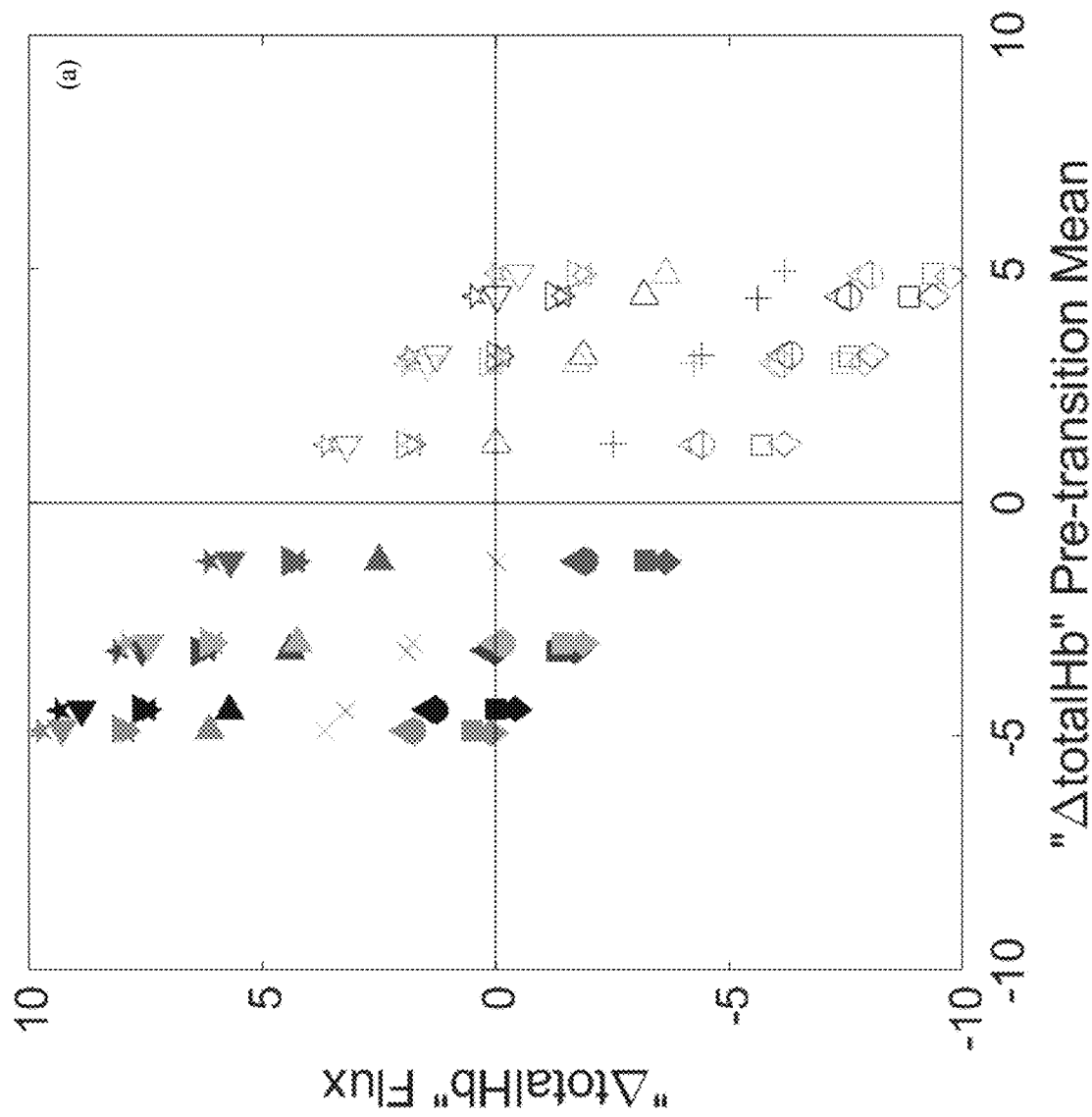
FIG. 13(a), (b). Evidence supporting validation that observed hyperbolic dependencies are not a simple consequence of applied computational methods.
Figure 13B:
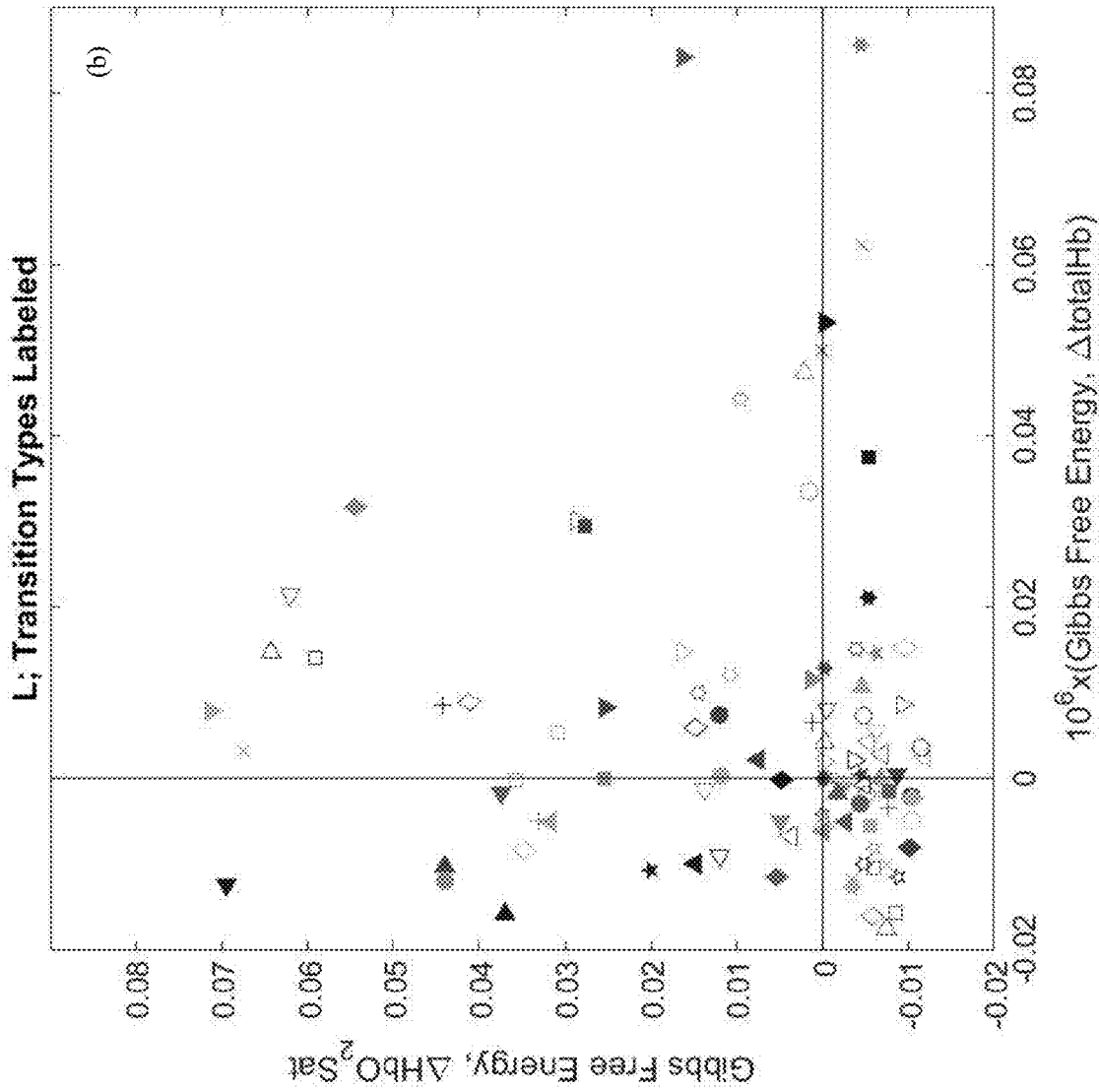
FIG. 13(b) reveals impact of randomly permuting the quantities comprising the adjacency matrix values for ΔHbO$_2$Sat and ΔtotalHb mean values that are used as input to the Gibbs free energy computation. This has the effect of randomizing the impact of the biological drivers that generate the coefficient patterns seen in these matrices, while not affecting the noise characteristics of the measured data. Both panels reveal complete loss of hyperbolic patterns.

A common approach for evaluating questions of this type is to substitute "noise" measures for experimental data. As shown in FIG. 13($a$), we have substituted "colored" noise for measures shown to yield the hyperbolic trends seen FIG. 6. The particular form of coloring used involved imposing onto the noise "time series" the same correlation value between measured values of $\Delta$oxyHb and $\Delta$deoxyHb, (−0.4), temporal mean HbO$_2$Sat value (85%), and ratios of oxyHb$_{AC}$/oxyHb$_{DC}$ and oxyHb$_{AC}$/deoxyHb$_{AC}$ as are observed in the actual breast data. Thus, our substituted measures were intentionally biased to mirror primary features of real data. As shown in FIG. 13($a$), whereas some gross features of overall trends are preserved, any hint of a hyperbolic dependence is lost, strongly indicating that this behavior is a consequence of specific biological features.

A second control study was conducted to determine whether evidence of hyperbolic features depend on subsequent data transforms to those used to generate the adjacency matrices. Here our attention is drawn to the data transforms employed to determine Gibbs free energy relationship between two Hb-components, and the LB plot which, should the trend be hyperbolic, will appear as a linear function in a double-reciprocal plot.

Because both plots describe similar functional forms, should these arise from the data transform per se, then a random permuting of the input data values should not significantly alter the observed behavior. Shown in FIG. 13($b$) is a representative plot of permuted input values for data plotted in FIG. 10. Similar to findings in FIG. 13($a$), any evidence of a hyperbolic trend is lost. Not shown are similar control measures applied to data shown in FIG. 11, which also demonstrate loss of the hyperbolic trend. Thus we conclude that the hidden trends observed are intrinsic to the action of some composite of tissue drivers which, being well-defined, indicate that observed behaviors, while disease sensitive, are strongly conserved.

To summarize, the findings presented herein document access to deeply hidden, highly structured behaviors arising from network descriptions of time-dependent measures of the Hb signal, several of which are strongly suggestive of enzyme-like behaviors even though the applied measures are decidedly macroscopic. These behaviors give evidence to a previously unrecognized level of quantifiable homeostatic control in living tissue that is accessible from resting state measures and is disease sensitive and hence influenced by disturbances in the prevailing genomic-epigenetic landscape.

As documented by findings from a representative measurement, tissue type and form of chronic disease, and the knowledge that the considered methods are easily translated to nearly all tissue classes, are favorably applied in a wide range of settings and readily support longitudinal monitoring, the described methods, with their demonstrated ability to yield varied forms of mainly independent network weights and structured behaviors providing access to set-point measures, collectively are well positioned to advance the goals of personalized medicine. Also understood is that the methods considered herein can be generalized to other forms of time-dependent physiological measures for which we anticipate that qualitatively similar forms of structured, yet hidden, behaviors can be described. As outlined subsequently, we also recognize that the above-described methods can be extended in various ways that support the previously identified medical and non-medical applications.

DESCRIPTION OF ALTERNATIVE EMBODIMENTS

A. Extensions and Generalizations of Specific Preferred-Embodiment Features

The invention is not dependent on the specific values assigned to any of the parameters, and can be modified in any of the following ways, which can be expected to enhance its generalizability and to support its potential for advancing personalized health evaluation.

1. The number of Hb-States defined can be either less than or greater than 10, and a state corresponding to any specifiable angular sector of the space depicted in FIG. 2 can be defined (e.g., State A is defined as the set of all points lying between rays inclined at angles of B degrees and C degrees with respect to the horizontal axis).

2. The definition of a Hb-State can take distances of points from the coordinate-system origin into account, in one or more coordinate directions, in addition to the angular information (e.g., State A is defined as the set of all points lying between rays inclined at angles of B degrees and C degrees with respect to the horizontal axis, with values for $\Delta$deoxyHb of at least D mol-L$^{-1}$ and at most E mol-L$^{-1}$, and with values for $\Delta$oxyHb of at least F mol-L$^{-1}$ and at most G mol-L$^{-1}$).

3. A reference point other than the resting-state temporal mean value can be used for defining temporal fluctuation values (e.g., $\Delta$totalHb), i.e., for defining the origin of the coordinate system. Different reference points may be chosen for different components of the Hb signal.

4. Transition counts may be based on the Hb-State of the $v^{th}$ voxel in the $t^{th}$ time frame and at a subsequent fixed number n of time frames, with n>1. In this case the time interval n$\Delta$t may be taken as an additional control parameter, and a count-vs.-n function generated [60].

5. The transition counts for each post-transition Hb-State can take into account not only the current time frame but also the one before that. Generalizing, for any positive number k, k=1, 2, 3, . . . , the k time steps prior to the current one may be considered. As an example, instead of a single count of all transitions from State 1 into State 2, an alternative embodiment could perform ten separate counts, corresponding to the ten states that may have preceded State 1: 1→1→2, 2→1→2, 3→1→2, 4→1→2, etc.

6. The method used to count transitions can be based, not on a fixed number of time frames, but on the variable number that elapses between each change from one (pre-transition) Hb-State to a distinct other (i.e., post-transition) Hb-State, in which case the number of possible transition types decreases from 100 to 90 [61].

7. Transition counts need not be evaluated at the level of individual voxels, but may consider 2 or more voxels defining a region on either an anatomical (e.g., physically contiguous) or functional basis (e.g., all have initial values of ΔtotalHb and ΔHbO$_2$Exc within specified ranges). As multiple voxels need not all be in the same Hb-State, rules would be specified for determining which pre- and post-transition States to count (e.g., the median State-value for all voxels in the defined cluster) and for when to count them (e.g., after one or more fixed values of n, or after a majority of voxels in the cluster have undergone a single transition from their initial State to a distinct other State).

8. The spatial unit over which States and transitions are defined need not be voxel-based, and none of the mathematical operations described herein pre-suppose or require reconstruction of volumetric images from the measurement data. All mathematical steps may be performed directly on data for a single measurement channel defined by one light source and one detector, or for multiple measurement channels or, alternatively, one or more data channels from a bioelectric measure.

9. In the multiple measurement-channel case mentioned in 8, the channels can be considered separately, or in combinations of two or more as mentioned in 7.

10. As mentioned in 7-9, the number of defined spatial volume units may be different from the voxel count $N_v$ defined in "Method of Implementing Preferred Embodiment". In general, the value of $N_v$ will be determined by the choice between image-based or measurement channel-based analysis, and on the choice between considering individual voxels or channels, or composites of voxels as mentioned in 7 or composites of channels as mentioned in 9.

11. In the place of constant increments, the increment added to the current value of a transition-count array element (Eq. (3)) can be a function of the current value. For example, incrementing by an amount directly proportional to the current value would be the temporal analogue of the procedure that produces "scale-free nets" [62] when it is used to assign links between new network nodes and currently existing ones. (In contrast, assigning links with a probability that is independent of the current link number, which is the analogue of the preferred-embodiment procedure, generates "exponential nets" [63]). Use of non-constant increments may be contraindicated when analysis of resting-state measurements is considered, if the start time for data collection is arbitrary. However, it could prove informative in, for example, the analysis of evolution to the steady state following an experimental perturbation.

12. The number of dimensions for the transition-count, dwell-time, mean-value, flux, etc., arrays may be increased beyond 2, in order to allow for simultaneous consideration of more than one scheme for defining the accumulation increments as mentioned in 11.

13. Multiple transition-count, dwell-time, mean-value, flux, etc., arrays may be employed, to enable separate counts of transitions occurring in different segments of the measurement time period (i.e., history-dependent measures) instead of a single integration over all time. This ability could be important for studies not performed under resting-state conditions. Even in the case of resting-state studies, it would allow, for example, for the evaluation of the hypothesis that the tissue under study passed through a sequence of physiological steady states during the measurement time course.

14. Multiple transition-count, dwell-time, mean-value, flux, etc., arrays may be employed, to enable separate counts of transitions occurring in different regions of the measured tissue volume instead of a single integration over the entire volume. This ability could be important for studies involving tissue structure known to have or suspected of having spatially heterogeneous hemodynamics. Even in the case of (presumably) homogeneous tissues, it would allow, for example, for the evaluation of the hypothesis of directed flows of information among them.

15. A capability afforded by the transition-count arrays described for the Preferred Embodiment, but not explicitly mentioned above, is that they allow for computation of transition joint-probabilities (e.g., the probability that a voxel transitions first from State 2 to State 3, and then to State 5), as desired.

16. The rules for accumulating changes in Hb-signal component levels are tied to the rule adopted for counting transitions, in the sense that the latter determines which time frames are used for evaluating increments of concentration (or percent change in saturation). However, the mathematical form of the component-value accumulation procedure is the same in all cases.

17. If a transition-counting method is adopted based on spatial regions containing more than a single voxel (for example, the approach outlined in 7), then a corresponding modification would be made to the method used to compute the concentration and percent change increments. As an example, suppose a counting method mentioned in 7 is implemented: a transition is counted when a majority of voxels in the region have undergone a single direct transition, and the regional median Hb-State-values are taken as the pre-transition and post-transition States. Then the pre-transition and post-transition concentrations (or percent saturations) would be averaged over the same subsets of voxels that determined the identities of the pre-transition and post-transition States. Other potentially useful information could be obtained by simultaneously accumulating [in a second set of arrays maintained in parallel with those defined in Eqs. (7)-(10)] the complementary changes averaged over the subsets of voxels that were in States different from those determined by the regional medians.

18. As mentioned, in addition to the grand-average (GA) formulations described in detail in "Method of Implementing Preferred Embodiment," two summation schemes have been developed for integrating Hb-signal information over tissue location and over time. These alternatives are known as "temporal mean of the spatial mean" (TMSM) and "spatial mean of the temporal mean" (SMTM). TMSM is appropriate for situations where substantial temporal variations (e.g., large-amplitude oscillations) in the measured signals are known or suspected to occur during the measurement period, and SMTM for situations where substantial spatial heterogeneities are or may be present. Taking transition flux as an illustrative example, where the GA formula (obtained by substituting Eqs. (3) and (4) into Eq. (10)) is:

$$\phi_k^X = \frac{\sum_{j=1}^{N_V} \sum_{i=1}^{N_{TS}} (U_k^X)_{ij}^{(3)}}{\sum_{j=1}^{N_V} \sum_{i=1}^{N_{TS}} (U_k)_{ij}}, \quad (22)$$

and the corresponding SMTM and TMSM formulas are:

$$\phi^X_{kSMTM} = \frac{1}{N_v} \sum_{j=1}^{N_v} \left[ \frac{\sum_{i=1}^{N_{TS}} (U_k^X)_{ij}^{(3)}}{\sum_{i=1}^{N_{TS}} (U_k)_{ij}} \right], \phi^X_{kTMSM} = \frac{1}{N_{TS}} \sum_{i=1}^{N_{TS}} \left[ \frac{\sum_{j=1}^{N_v} (U_k^X)_{ij}^{(3)}}{\sum_{j=1}^{N_v} (U_k)_{ij}} \right]. \quad (23)$$

We note that the SMTM flux is approximately equal to the GA flux if $\Sigma_{i=1}^{N_{TS}}(U_k)_{ij}$ has a small coefficient of variation (COV) across the spatial dimension j, and the TMSM flux is approximately equal to the GA flux if $\Sigma_{j=1}^{N_v}(U_k)_{ij}$ has a small COV across the temporal dimension i.

The dwell time and pre- and post-transition mean value features have TMSM and SMTM formulations, which differ from their GA counterparts in the same manner as do the flux variants. (And as a consequence, the computed values for features such as Gibbs free energy vary according to which mean-value formulations is used to generate the input, although the formulas used to compute said features are the same in every case.) In contrast, values of the transition probability and transition mass features are independent of the summation scheme used.

19. While three methods of grouping transition types are explicitly mentioned in preceding sections (i.e., all types lying in the same adjacency matrix row, column, or strip parallel to the main diagonal of), none of the mathematical operations or methods of analysis is restricted to those ways of defining transition-type categories. Any other rule, however motivated, for assigning two or more transition types to a group also can be applied, and the numbers of transition types per group may be either equal (e.g., the 'same pre-transition State' and 'same post-transition State' groupings) or unequal (e.g., the 'same diagonal' groupings).

20. The number of network features considered in a co-dependency analysis is not limited to two. Any number of features may be incorporated, comprising any permutation of Hb-signal components, features that are and are not functions of Hb-signal component levels (e.g., transition flux and transition probability, respectively), edge-based and node-based features (e.g., flux and post-transition dwell time, respectively), and pre- and post-transition values.

21. The weighted-network entropy feature described in "Method of Implementing Preferred Embodiment" is based on the treatment found in [56] and is a straightforward extension of the conventional node entropy of an unweighted network [56]. However, the methods herein presented are not restricted to that weighted-network entropy formulation, but also could employ any of the available weighted-network entropy metrics [64].

22. The described methods for analysis of time-series data are not limited to the fNIRS measurement data employed for exemplary purposes, or to the tissue types or structures that were considered, or to hemodynamic information encoded in the measurements, but can be applied to biological time-varying signals measured from any tissue, encoded in any form of energy, and obtained using any suitable measurement technology. Thus, for example: acoustic energy (e.g., ultrasound) time series, instead of or in addition to light or other electromagnetic (EM) signals, can be the input data; the information of interest can reside in an internally generated signal (e.g., thermography, bioelectric), as opposed to one that is impressed upon an exogenous carrier (e.g., fNIRS, fMRI, acoustic imaging, OCT); EM-based techniques may make use of any suitable frequencies (e.g., fMRI, electrical impedance tomography); and, for tissues that generate time-varying EM fields (e.g., brain, heart), the data on which the various embodiments described operate may be measured by ECG, EEG, MCG or MEG time series or combinations of these and the indicated methods. Common to all of these alternative physiological measures is the understanding of a close correspondence between temporal features in the data and well-described physiological behaviors (e.g., canonical elements of the ECG waveform and cardiac function, dynamic thermographic measures that reflect time-varying features of blood flow, etc.). As noted elsewhere herein, the methods described here offer the ability to transform such measures into a set of network adjacency matrices, from which measures of co-dependent behaviors can be defined that serve to identify physiological or pathological setpoints.

23. For all of the above considered alternative embodiments (Eqs. (1)-(23)), it is understood that the native signal can be preprocessed to isolate/exclude frequency bands of interest. For instance, low-pass filtering of the represented NIRS measures could serve to remove contributions from, e.g., detectable cardiac signals.

24. It is recognized that, in contrast to multi-wavelength measurements of hemodynamic signals, other types of time-series physiological measurement generate data for which it may not be evident how that data could be resolved into two or more "components" that will then be used to define "States." However, each type of signal possesses characteristic features that can be made to serve as the basis for a State definition. As an example, EEG signals have a well-known frequency-band structure [65], and the temporally co-varying amplitudes for multiple bands can be taken as the counterparts of the co-varying values of the Hb-signal components. In the case of fMRI, which does produce hemodynamic time-series data but is sensitive to only the deoxyHb signal component [66], in many cases components can be extracted from the peak-amplitude, time-to-peak, and full-width-at-half-maximum parameters typically used to characterize hemodynamic response functions [67]. Also, similar to the EEG case, frequency-domain approaches can be used to define fMRI components, especially in the case of resting-state measurements [68].

B. Additional Alternative-Embodiment Considerations

1. Applicability of Formal Language Theory

Discrete-valued information such as sequences of Hb-State or, equivalent definitions considered above, can be formally regarded as arbitrary-length "words" in a language having a 10-"letter" alphabet (Hb-components having (+/−) values relative to temporal mean). The structures and constraints that may be concealed in these sequences are unknown a priori, and it is prudent to adopt analysis strategies that can handle arbitrary degrees and types of complexity. Work in other fields has shown that formal language theory (FLT) is well-suited for the type of situations presented by such information [69]. As an example of a goal that is conceptually straightforward, one might seek to use FLT to characterize the level in the Chomsky hierarchy that corresponds to a State- or transition-derived language, to determine a set of grammatical rules from which the sequences can be derived [70]. Such information could then be used for evaluating a research goal such as whether the hierarchy level, or the number of, or specific content of, grammatical rules differs among different subject groups. Examples of criteria that may be used to differentiate these groups include: the presence of absence of pathology, different levels of distraction (brain studies), or fatigue or stress in cases where the aim is to appreciate factors affecting overall performance in high stress environments.

2. Electrical Network Analogies

While the noted understandings from FLT constitute a particular alternative approach to increasing the type and quantity of information that could be extracted from fNIRS time-series data, methods for expressing features in terms of other quantities that have biological relevance but are not directly observable are also available. Thus we acknowledge the potential to extend the network representation considered here into one where the goal is to derive coefficients from a hidden network of coefficients that reflect features corresponding to details of feedback mechanisms. In particular, we consider the framework of a DC electrical network [71], in recognition of the analogies that can be drawn between $P_k$ (or $P_k \phi_k^X = m_k^X$) and $\tau_k^{(1)}$ to the electrical current and resistance represented in Ohm's Law. We note that the analogies drawn here between various network features and DC circuit elements are in addition to the ones that motivated the idea of treating the hemodynamic State-transition network as a thermodynamic system.

Connection to the physiological processes underlying observed patterns of state transition coefficients comes from an understanding that real-world electric-circuit networks are typically based on a distribution of power sources required to drive various specialized functionalities. As our finite-state network representation considers behaviors that originate on a macroscopic scale within an inhomogeneous underlying tissue architecture, it seems likely that the factors that modulate the Hb signal will also influence features of the State-transition network in a distributed manner. Consequently, our attention has been on devising a scheme that allows for derivation of coefficients that correspond to such distributions.

The definitions of $\tau_k^{(1)}$, $P_k$ and $\phi_k^X$ suggest a correspondence between $\tau_k^{(1)}$ and electrical resistance, and likewise between either $P_k$ or $P_k \phi_k^X$ and current. (The $P_k$ values are "transition currents" if transitions are analogized to a type of particle, while $P_k \phi_k^X$ values are concentration-change currents or saturation-change currents.) The different network States can be likened to nodes in an electrical network, and $\tau_k^{(1)}$ to the value of a resistor that conducts current from the pre-transition node to the post-transition node (more strictly, a resistor in series with an ideal diode, to allow for $\tau_{10(j-1)+i}^{(1)} \neq \tau_{10(i-1)+j}^{(1)}$). These correspondences bring to mind at least two additional analogies to properties of electrical circuits.

a) A new quantity corresponding to voltage, $V_k$ or $V_k^X$, can be defined, by applying an analogue of Ohm's law to the transition-probability and rate values:

$$V_k = \tau_k^{(1)} P_k, V_k^X = \tau_k^{(1)} P_k \phi_k^X, \quad (24)$$

where X is any of the Hb-signal components D, E, O, S or To in Eq. (7).

b) In the typical framing of electrical-network analysis problems [72], the resistances and applied electromotive forces (EMFs) are known quantities and the voltages and currents are the unknowns that are solved for. A different, inverse, version of the problem is suggested here, in that the currents and resistances are known quantities, and what must be found is an EMF or combination of EMFs that would produce the known currents, given the known structural (connectivity and resistances) and dynamic (currents) properties of the network. Assuming these quantities can be identified with a degree of confidence, then the considered approach would seem capable of amplifying our understanding of the actions of feedback mechanisms whose influences can be directly observed but whose details remain hidden.

3. Applicability of Hb-State Concepts to Enhancing Capabilities of Other fNIRS Analysis Strategies The potential to express properties of the States in terms of their sensitivities to more primitive behaviors (e.g., frequency-dependent amplitudes of time-varying signal levels, spatial heterogeneity of the amplitudes, spatial heterogeneity of the phases) is one that we have previously recognized. Here we refer to a methodology described by our group, which demonstrated that cross-domain moments (i.e., mean, variance) of spatiotemporal behaviors can be distinguished in terms of their sensitivity to these primitive behaviors [4]. While here our emphasis is on exploration of data features associated with specific transition types or Classes, we also recognize that the section of the FIG. 2 point cloud corresponding to each State can be represented as a time series. In fact, because each State is a composite of the five elements of the Hb signal, five time series can be defined for each State. For each of these it can be shown that there are fourteen nontrivial cross-domain (i.e., involving both space and time) moments that can be defined (i.e., the eight that are considered in [4] plus an additional six, five of which would be trivial (because always exactly zero) should the Hb signal not be separated into States). Our interest in these quantities is motivated by the expectation that as the underlying drivers of tissue-vascular coupling vary (e.g., as they are influenced by actions of disease), they can imprint different spatiotemporal behaviors that are sensitive to the indicated primitives. Thus we acknowledge that in addition to the above-described transition-dependent network properties, representations of bulk features of the network may add to the differential information that is accessible.

4. Extension to Other Conceptual Domains in Graph Theory

As a separate avenue for potential future developments, we note that the range of network indices herein described spans a subset of the broader field of graph theory (which is, in turn, a subset of the even broader field of discrete mathematics). In particular, strong analogies can be drawn between the network features emphasized in the preferred embodiment (e.g., transition probabilities, dwell times, pre- and post-transition mean values, fluxes) and graph-theory methods developed for analysis of substrate concentrations and fluxes (i.e., rates of substrate production and consumption) as determined by the actions of enzymes linked together in functional networks (i.e., for metabolomics) [73,54]. Consequently, these parallels bring the expectation that algorithms used to analyze the functioning of networks into elementary flux modes [74] can also be applied to the network of Hb-flux states, to determine whether pathway preferences exist and, if so, if there are informative differences between the dominant pathways for different subject populations, or among individuals within a population.

Further, the preceding can be extended by recognizing that the mathematically defined network of states that is subjected to the analysis may include other nodes in addition to the hemodynamic States. For example, a goal of the analysis may be to evaluate one or more hypotheses regarding the role of known biochemical or physiological processes in determining the observed transition probabilities, fluxes, etc. Typically these processes are the entities of ultimate scientific interest, but they are not directly observable, at least not under the same experimental or clinical conditions as the hemodynamic signal. Thus the Hb States constitute the "visible units" of the enlarged network, while states of the physiological processes (e.g., levels of specific metabolites, presence/absence of induced isoenzymes, levels of regulatory species) are the "hidden units" [75]. Connecting the network nodes would be two types of "edges": those that, on the basis of either observation or fundamental biological understandings, are known to exist between pairs of visible or pairs of hidden nodes; and those that are hypothesized to exist between a hidden node and a visible one. One goal of the analysis considered here could be to determine—for each hypothetical pattern of edges connecting a visible node and a hidden one—edge-weight values that would allow the hidden fluxes to drive the observed ones while maintaining hidden fluxes that are plausible physically (i.e., all irreversible reactions proceed in the correct direction) and biologically (i.e., all flux magnitudes fall between established lower and upper limits) [76, 77]. A related goal could be to select among different hypotheses, based on the sensitivities of network fluxes to perturbations of the computed edge weights. The latter application is conceptually similar to established strategies used to analyze fMRI and fNIRS data for the purpose of selecting among models of effective connectivity between brain regions [78].

Also understood is the availability of other, complementary set of indices for characterizing networks—e.g., average path length, diameter, average clustering coefficient, centralization, various centrality measures (degree, closeness, betweenness, eigenvector, and subgraph centrality), matching index [79]. The preferred embodiment does not explicitly consider these, for the reason that the network of Hb-signal States constitutes a complete graph, which is to say that every element in its adjacency matrix is equal to 1 [79]. As such, none of the mentioned network indices would have nontrivial values. However, meaningful network-index values can be obtained by substituting weighted adjacency matrices [76] for the more commonly considered type in which each element simply indicates the presence (1) or absence (0) of a direct connection. The preferred embodiment generates a set of quantities that can be taken as adjacency weight values: transition probability, dwell times, pre- and post-transition mean values, fluxes, masses, Gibbs free energies. Index values thus generated could be interpreted as features of the underlying networks, and then evaluated to test for the presence of informative differences between subject populations, or among individuals within a population.

The preceding discussion has used the concept of networks in a qualitatively different manner from that which is considered in the field of machine learning using artificial neural networks [80,81]. We are aware that some of the data analysis efforts suggested by the above enlarged networks can become computationally challenging. It is of course plausible to use network-based (in the machine-learning sense) techniques to search for plausible, or even optimal, solutions to problems such as the previously described analysis of connectivity between the visible and hidden parts of a composite functional network.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

REFERENCES TO NEW PATENT

[1] F. B. Hu, et al., "Diet, lifestyle, and the risk of type 2 diabetes mellitus in women", N Engl J Med., 345, 790-797 (2001).

[2] M. J. Stampfer et al, "Primary prevention of coronary heart disease in women through diet and lifestyle" N Engl J Med, 343, 16-22 (2000).

[3] S. S. Segal, "Regulation of Blood Flow in the Microcirculation", Microcirc. 12, 33-45, 2005).

[4] H. L. Graber, et al. "Enhanced resting-state dynamics of the hemoglobin signal as a novel biomarker for detection of breast cancer", Medical Physics 42, 6406-6424 (2015).

[5] K. G. Moulakakis et al. "Hyperperfusion syndrome after carotid revascularization", J. Vascular Surg., 49, 1060-1068 (2009).

[6] X. Zhan, and R. Yu, "A window into the brain: Advances in psychiatric MilI," BioMed Research International Article 542567, (2015).

[7] M. Beauregard, "Functional neuroimaging studies of the effects of psychotherapy", Dialogues in Clinical Neuroscience, 16, 75-81 (2014).

[8] L. A. Barquero, et al., "Neuroimaging of reading intervention: A systemic review and activation likelihood estimate meta-analysis", PLoS One, 9, Article e83668 (2014).

[9] S. Calderoni et al., "Rehabilitative interventions and brain plasticity in autism spectrum disorders: Focus on MRI-based studies", Frontiers in Neurosci. 10, Article 139, (2016).

[10] J. Saliba, et al., "Functional near-infrared spectroscopy for neuroimaging in cochlear implant recipients", Hearing Research 338, 64-75 (2016).

[11] R. Sitaram et al. "Closed-loop brain training: The science of neurofeedback", Nature Reviews: Neuroscience 18, 86-100 (2017).

[12] A. Curtin et al., "Evaluation of evoked responses to pulsed-matched high frequency and intermittent theta burst transcranial magnetic stimulation using simultaneous functional near-infrared spectroscopy", Neurophotonics 4, Article 041405 (2017).

[13] J. J. Vaquero and P. Kinahan, "Positron emission tomography: Current challenges and opportunities for technological advances in clinical and preclinical imaging systems," *Ann Rev Biomed Eng* 17, 385-414 (2015).

[14] R. Ahmad and P. Kuppusamy, "Theory, instrumentation, and applications of EPR oximetry," *Chemical Reviews* 110, 3212-3236 (2010).

[15] Y. Wang, et al., "Electrochemical sensors for clinic analysis," Sensors 8, 2043-2081 (2008).

[16] T. Yoshihara, et al. "Oxygen imaging of living cells and tissue using luminescent molecular probes," J. *Photochem and Photobiol C: Photochem Rev.* 30, 71-95 (2017).

[17] L. V. Wang and H. Hu, "Photoacoustic tomography: In vivo imaging from organelles to organs," Science 335, 1458-1462 (2012).

[18] Y. Yamada et al., "Time-Domain Near-Infared Spectroscopy and Imaging: A Review", Appl. Sci., 9, 1127, (2019).

[19] M L Jepsen, U.S. Pat. No. 9,730,649B1, Optical Imaging of Diffuse Medium (2016).

[20] S. Schuh, et al., "Imaging blood vessel morphology in skin: Dynamic optical coherence tomography as a novel potential diagnostic tool in dermatology", *Dermatologic Therapy*, 7187-202 (2017).

[21] S. Belanger et al., "Real time diffuse optical tomography based on structured illumination," *J Biomed Opt* 15, Article 016006 (2010).

[22] M. Jayachandran et al., "Critical review of noninvasive optical technologies for wound imaging," *Adv Wound Care* 5, 349-359 (2016).

[23] S. K. Piper et al., "A wearable multi-channel fNIRS system for brain imaging in freely moving subjects," Neuroimage 85, 64-71 (2014).

[24] J. B. Balardin et al., "Imaging brain function with functional near-infrared spectroscopy in unconstrained environments," *Frontiers in Human Neuroscience* 11, Article 258 (2017).

[25] Al abdi et al., "Optomechanical imaging system for breast cancer detection," *J Opt Soc Am A*, 28, 2473-2493 (2011).

[26] A. Mazhar, et al., "Structured illumination enhances resolution and contrast in thick fluorescence imaging," *J Biomed Opt.*, 15 Article 0150506 (2010)]. Non-contact, broad-area illumination methods can also be applied with the aim of employing holographic techniques [U.S. Pat. No. 9,730,649B1].

[27] D. R. Busch, et al. "Towards non-invasive characterization of breast cancer and cancer metabolism with diffuse optics," *PET Clinics* 8, 345-365 (2013).

[28] P. Taroni, et al. "Non-invasive optical estimate of tissue composition to differentiate malignant from benign breast lesions: A pilot study," *Scientific Reports* 7, Article 40683 (2017).

[29] B. J. Tromberg, et al., "Predicting responses to neoadjuvant chemotherapy in breast cancer: ACRIN 6691 trial of diffuse optical spectroscopic imaging," *Cancer Res* 76, 5933-5944 (2016).

[30] C. H. Schmitz et al. "Design and implementation of dynamic near-infrared optical tomographic imaging instrumentation for simultaneous dual-breast measurements," *Applied Optics* 44, 2140-2153, (2005).

[31] S. Amalakanti et al. "Pulse Oximetry Overestimates Oxygen Saturation in COPD", Respiratory Care, 61, 423-427 (2016).

[32] J. Steppan et al., "Cerebral and tissue oximetry", Best Practice Res. Clin. Anaesthes. 28, 429-439 (2014).

[33] S. Fantini, "Dynamic model for the tissue concentration and oxygen saturation of hemoglobin in relation to blood volume, flow velocity, and oxygen consumption: Implications for functional neuroimaging and coherent hemodynamics spectroscopy (CHS)," Neuroimage 85, 202-221 (2014).

[34] C. H. Schilling and B. O. Palsson, "The underlying pathway structure of biochemical reaction networks," Proc. Natl. Acad. Sci., 95, 4193-4198 (1998).

[35] P. R. Somvanshi and K. V. Venkatesh, "A conceptual review on systems biology in health and diseases: From biological networks to modern therapeutics," Systems and Synthetic Biology 8, 99-116 (2014).

[36] K. B. et al., "Neuronal firing rate homeostasis is inhibited by sleep and promoted by wake", Cell 165, 180-191 (2016).

[37] A. E. Pereda et al., "Gap junction-mediated electrical transmission: Regulatory mechanisms and plasticity," Biochim. Biophys. Acta 1828, 134-146 (2013).

[38] S. S. Segal "Integration and Modulation of Intercellular Signaling Underlying Blood Flow Control", J. Vasc. Res., 52, 136-157 (2015).

[39] G. W. Wylie, et al., "Using co-variations in the Hb signal to detect visual activation: A near infrared spectroscopic imaging study," NeuroImage, Vol. 47, 473-481 (2009).

[40] H. J. Forman, "Redox-signaling: an evolution from free radicals to aging", Free Radic Biol Med., 97, 398-407 (2016).

[41] D. J. Kominsky et al., "Metabolic Shifts in Immunity and Inflammation", J Immunol. 184, 4062-4068 (2010).

[42] D. D. Thomas "Breathing new life into nitric oxide signaling: A brief review of the interplay between oxygen and nitric oxide", Redox Biol., 5, 225-233 (2015).

[43] I. F. Tannock and J. A. Hickman, "Limits to Personalized Cancer Medicine", N Engl J Med 375, 1289-1294, (2016).

[44] (C. M. Delude, "Deep phenotyping: The details of disease", Nature, 527 S14-S15 (2015).

[45] R. L. Barbour et al., "Method for representations of network-dependent features of the hemoglobin signal in living tissues for detection of breast cancer and other applications", U.S. Pat. No. 10,105,090B2 (2018).

[46] G. Oster, "Network Thermodynamics", Nature 234, 393-399, (1971).

[47] G. F. Oster, "Tellegen's Theorem and Thermodynamic Inequalities", J. Theor. Biol, 32, 219-241 (1971).

[48] A. Fornito et al., "Fundamentals of Brain Network Analysis", Academic Press, (2016).

[49], J. Lei, et al., "Assessing the Healing of Venous Leg Ulcers Using a Noncontact Near-Infrared Optical Imaging Approach", Adv Wound Care, 7, 134-143, (2018).

[50], R. Kwasinski et al., "Tissue Oxygenation Changes to Assess Healing in Venous Leg Ulcers Using Near-Infrared Optical Imaging", Adv Wound Care, 8, 565-597, (2019).

[51]. A. de Paula, "Econometrics of Network Models", in Advances in Economics and Econometrics", pp 268-323, (2017), Cambridge University Press, DOI: https://doi.org/10.1017/9781108227162.008 [52] S. M. Golas et al., "Gibbs free energy of protein-protein interactions correlates with ATP production in cancer cells", J. Biol. Phys., 45, 423-430 (2019).

[53] E. A. Rietman et al., "Thermodynamic measures of cancer: Gibbs free energy and entropy of protein-protein interactions", J. Biol Phys., DOI 10.1007/s10867-016-9410-y, (2016)

[54] E. A. Rietman, J. G. Scott, J. A. Tuszynski, and G. L. Klement, "Personalized anticancer therapy selection using molecular landscape topology and thermodynamics," Oncotarget 8, 18735-18745 (2017).

[55] Breitkreutz et al., "Molecular signaling network complexity is correlated with cancer patient survivability," PNAS, 109, 9209-9212, (2012).

[56] R. Kazemi, "Entropy of weighted graphs with the degree-based topological indices as weights," MATCH Commun. Math. Comput. Chem. 76, 69-80 (2016).

[56a] F. Rohart, B. Gautier, A. Singh, and K.-A. Lê Cao, "mixOmics: An R package for 'omics feature selection and multiple data integration," PLoS Computational Biology 13: e1005752 (2017).[56b] Z. Ahmed, "Practicing precision medicine with intelligently integrated clinical and multi-omics data analysis", Human Genetics, 14:35 (2020).[57] Open Science Framework: "Resting-State Simultaneous Dual-Breast Imaging." OSF Resting-State Simultaneous Dual-Breast Imaging (https://osf.io/4cr3z/)

[58] H. L. Graber, Y. Pei, and R. L. Barbour, "Imaging of spatiotemporal coincident states by DC optical tomography," *IEEE Transactions on Medical Imaging* 21, 852-866 (2002).

[59] Y. Pei, H. L. Graber, and R. L. Barbour, "Influence of systematic errors in reference states on image quality and on stability of derived information for DC optical imaging," *Applied Optics* 40, 5755-5769 (2001).

[60] R. L. Barbour and H. L. Graber, "Characterization of hemoglobin dynamics as a co-varying system in the resting state: Evidence of functional bias of preferred states and sensitivity to disease," Poster #220 at 2016

Biennial Meeting of The Society for Functional Near Infrared Spectroscopy (Paris, Oct. 13-16, 2016)).
[61] R. L. Barbour, et al., PLoS One 13, e0198210.https://doi.org/10.1371/journal.pone.0198210, (2018).
[62] A.-L. Barabási and R. Albert, "Emergence of scaling in random networks," *Science* 286, 509-512 (1999).
[63] R. Albert, H. Jeong, and A.-L. Barabási, "Error and attack tolerance of complex networks," Nature 406, 378-382 (2000).
[64] Y. M. Omar and P. Plapper, "A survey of information entropy metrics for complex networks," Entropy 22, doi:10.3390/e22121417 (2020).
[65] R. M. Mehmood and H. J. Lee, "Exploration of prominent frequency wave in EEG signals from brain sensors network," Int. J. Distributed Sensor Networks 2015, Article ID 386057 (2015).
[66] R. B. Buxton, "The physics of functional magnetic resonance imaging (fMRI)," Reports on Progress in Physics 76, 096601 (2013).
[67] M. A. Lindquist, J. M. Loh, L. Y. Atlas, and T. D. Wager, "Modeling the hemodynamic response function in fMRI: Efficiency, bias and mis-modeling," NeuroImage 45, S187-S198 (2009).
[68] N. H. Yuen, N. Osachoff, and J. J. Chen, "Intrinsic frequencies of the resting-state fMRI signal: The frequency dependence of functional connectivity and the effect of mode mixing," Frontiers Neurosci. 13, 900 (2019).
[69] M. Gheorghe and V. Mitrana, "A formal language-based approach in biology", Compoarative and Functional Genomics 5, 91-94 (2004).
[70] W. T. Fitch and A. D. Friederici, "Artificial grammar learning meets formal language theory: An overview", Phil. Trans. R. Soc. B 367, 1933-1955 (2012).
[71] K. S. Suresh Kumar, *Electrical Circuits and Networks*. Pearson Education Canada (2009). ISBN 978-8131713907. [72] TR. Kuphaldt, "DC Network Analysis," Chapter 10 in *Lessons in Electrical Circuits, Volume I—DC*, 5$^{th}$ Ed. Open Book Project (2006). Available online at https://www.allaboutcircuits.com/textbook/direct-current/),
[73] C H. Schilling and B. O. Palsson, "The underlying pathway structure of biochemical reaction networks," Proc. Natl. Acad. Sci. 95, 4193-4198 (1998).
[74] S Schuster, T. Dandekar, and D. A. Fell, "Detection of elementary flux modes in biochemical networks: A promising tool for pathway analysis and metabolic engineering," Trends in Biotechnology 17, 53-60 (1999).
[75] L. R. Rabiner, "A tutorial on hidden Markov models and selected applications in speech recognition," *Proceedings of the IEEE* 77, 257-286 (1989).
[76] S. Umeyama, "An eigendecomposition approach to weighted graph matching problems," *IEEE Transactions on Pattern Analysis and Machine Intelligence* 10, 695-703 (1988).
[77] C. H. Schilling, D. Letscher, and B. O. Palsson, "Theory for the systemic definition of metabolic pathways and their use in interpreting metabolic function from a pathway-oriented perspective," *J. Theoretical Biology* 203, 229-248 (2000).
[78] K. E. Stephan, W. D. Penny, J. Daunizeau, R. J. Moran, and K. J. Friston, "Bayesian model selection for group studies," NeuroImage 46, 1004-1017 (2009).
[79] G. A. Pavlopoulos, M. Secrier, C. N. Moschopoulos, T. G. Soldatos, S. Kossida, J. Aerts, R. Schneider, and P. G. Bagos, "Using graph theory to analyze biological networks," BioData Mining 4 (2011).
[80] A. K. Jain, J. Mao, and K. M. Mohiuddin, "Artificial neural networks: A tutorial," *IEEE Computer Magazine*, March 1996, 31-44. [81] L. J. Lancashire, C. Lemetre, and G. R. Bal, "An introduction to artificial neural networks in bioinformatics—application to complex microarray and mass spectrometry datasets in cancer studies," *Briefings in Bioinformatics* 10, 315-329 (2009).

What is claimed is:

1. A method of identifying at least one biomarker in a subject, the method comprising:
   a) acquiring a physiological time-series measure from a set of sensors in communication with a body region of the subject while the subject is in a substantially resting state;
   b) converting the physiological time-series measure to a set of network adjacency matrices; and
   c) identifying at least one biomarker in the subject that exhibits structured co-dependent behaviors based on the set of network adjacency matrices.

2. The method of claim 1, wherein the set of sensors detects a near infrared spectroscopic signal.

3. The method of claim 1, wherein the set of sensors detects a hemoglobin-related signal in the subject, wherein the set of network adjacency matrices are based on measures of a temporal mean of the hemoglobin-related signal.

4. The method of claim 1, wherein an applied state definition is used in the converting of the physiological time-series measure to the set of network adjacency matrices.

5. The method of claim 1, wherein the structured co-dependent behaviors in the set of network adjacency matrices fit to a hyperbolic function from which a setpoint behavior can be identified.

6. The method of claim 1, wherein the time-series measure involves a measurement from a source exogeneous to the subject's body.

7. The method of claim 1, wherein the time-series measure involves a measurement from a source endogenous to the subject's body.

8. The method of claim 1, wherein the set of sensors is in contact with the subject.

9. The method of claim 1, wherein the physiological time-series measure involves a measurement from a bio-electric source.

10. The method of claim 1, wherein the physiological time-series measure is obtained from an acoustic source.

11. The method of claim 1, wherein the physiological time-series measure is obtained from a photoacoustic source.

12. The method of claim 1, further comprising performing a longitudinal measure of at least one biology-influenced signal, wherein the longitudinal measure determines changes over time in at least one of either detected signal amplitudes, network adjacency-matrix values, patterns of values within individual adjacency matrices, or co-dependencies between values in at least two adjacency matrices.

13. The method of claim 1, further comprising comparing the at least one identified biomarker in the subject to an identified biomarker obtained from a healthy subject, wherein the subject has a disease.

14. The method of claim 1, further comprising comparing the at least one identified biomarker in the subject to an identified biomarker obtained from a disease subject, wherein the subject is healthy.

15. The method of claim 1, wherein the set of sensors uses at least two sensing methods.

16. The method of claim 3, wherein the hemoglobin-related signal is oxygenated hemoglobin (oxyHb); deoxygenated hemoglobin (deoxyHb); tissue-Hb oxygen exchange (HbO2Exc), wherein Hb oxygen exchanged is defined as HbO2Exc=deoxyHb−oxyHb; total hemoglobin (Hb), wherein total Hb is defined as totalHb=deoxyHb+oxyHb; or Hb oxygen saturation, wherein Hb oxygen saturation is defined as HbO2Sat=(oxygenated Hb/total Hb)×100.

17. The method of claim 1, wherein the subject is healthy.

18. The method of claim 1, wherein the subject has a disease or cancer.

19. The method of claim 1, wherein the body region is a breast of the subject, the brain of the subject, the torso of the subject, a limb of the subject, or the skin of the subject.

* * * * *